(12) United States Patent
Yoo et al.

(10) Patent No.: US 11,970,534 B2
(45) Date of Patent: Apr. 30, 2024

(54) ANTIBODIES AND MOLECULES THAT IMMUNOSPECIFICALLY BIND TO BTN1A1 AND THE THERAPEUTIC USES THEREOF

(71) Applicants: STCUBE & CO., INC., Seoul (KR); Board of Regents, The University of Texas System, Austin, TX (US)

(72) Inventors: Stephen Sunghan Yoo, Centreville, VA (US); Michael Joseph Surace, Germantown, MD (US); Steven Hsesheng Lin, Pearland, TX (US); Amrish Sharma, Houston, TX (US)

(73) Assignees: STCUBE & CO., INC., Seoul (KR); Board of Regents, The University of Texas System, Austin, TX (US)

( * ) Notice: Subject to any disclaimer, the term of this patent is extended or adjusted under 35 U.S.C. 154(b) by 595 days.

(21) Appl. No.: 17/103,308

(22) Filed: Nov. 24, 2020

(65) Prior Publication Data

US 2021/0147537 A1 May 20, 2021

Related U.S. Application Data

(62) Division of application No. 15/781,071, filed as application No. PCT/US2016/064436 on Dec. 1, 2016, now Pat. No. 10,875,920.

(60) Provisional application No. 62/262,309, filed on Dec. 2, 2015.

(51) Int. Cl.
*C07K 16/28* (2006.01)
*A61K 39/395* (2006.01)

(52) U.S. Cl.
CPC ........ *C07K 16/2803* (2013.01); *A61K 39/395* (2013.01); *C07K 2317/34* (2013.01); *C07K 2317/73* (2013.01); *C07K 2317/77* (2013.01); *C07K 2317/92* (2013.01)

(58) Field of Classification Search
CPC ............ C07K 16/2803; C07K 2317/34; C07K 2317/73; C07K 2317/77; C07K 2317/92; C07K 2317/56; C07K 2317/565; A61P 35/00; A61K 39/395; A61K 2035/505
See application file for complete search history.

(56) References Cited

FOREIGN PATENT DOCUMENTS

WO  WO-2009030884 A2 *  3/2009  ....... C07K 14/70503
WO  WO 2011/156520 A2   12/2011
WO  WO-2015015003 A1 *  2/2015  ............ A61K 45/06

OTHER PUBLICATIONS

Baxevanis, Expert Opinion: Drug Discovery, vol. 3, No. 4, p. 441-452. (Year: 2008).*
Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Murphy et al. (Journal of Immunological Methods, vol. 463, p. 127-133, 2018.*
Arnett et al., "Immune modulation by butyrophilins," Nat. Rev. Immunol., 14(8):559-569 (2014).
Banghart et al., "Butyrophilin is expressed in mammary epithelial cells from a single-sized messenger RNA as a Type I membrane glycoprotein," J. Biol. Chem., 273(7):4171-4179 (1998).
Cheung et al., "Scanning N-glycosylation mutagenesis of membrane proteins," Methods, 41(4):451-459 (2007).
Dolcetti et al., "Measurement of myeloid cell immune suppressive activity," Curr. Protoc. Immunol., 14.17.1-14.17.25 (2010).
Foote et al., "Antibody framework residues affecting the conformation of the hypervariable loops," J. Mol. Biol., 224:487-499 (1992).
Helenius et al., "Intracellular functions of N-linked glycans," Science, 291(5512):2364-2369 (2001).
Katoh et al., "MAFFT: a novel method for rapid multiple sequence alignment based on fast Fourier transform," Nucleic Acids Res., 30(14):3059-3066 (2002).
Larocca et al., "Akt1 is essential for postnatal mammary gland development, function, and the expression of Btn1al," PLOS one, 6(9):e24432 (2011).
Lefranc et al., "IMGT, the international ImMunoGeneTics database," Nucleic Acids Res., 27(1):209-212 (1999).
Marchler-Bauer et al., "CDD: a conserved domain database for the functional annotation of proteins," Nucleic Acids Res., 39:D225-D229 (2011).
Ogg et al., "Expression of butyrophilin (Btn1a1) in lactating mammary gland is essential for the regulated secretion of milk-lipid droplets," Proc. Natl. Acad. Sci. USA, 101(27):10084-10089 (2004).
Schwarz et al., "Mechanisms and principles of N-linked protein glycosylation," Curr. Opin. Struct. Biol., 21(5):576-582 (2011).
Smith et al., "BTN1A1, the mammary gland butyrophilin, and BTN2A2 are both inhibitors of T cell activation," J. Immunol., 184(7):3514-3525 (2010).
Søreide, "Receiver-operating characteristic curve analysis in diagnostic, prognostic and predictive biomarker research," J. Clin. Pathol., 62(1):1-5 (2009).

(Continued)

Primary Examiner — Hong Sang
(74) Attorney, Agent, or Firm — Jones Day

(57) ABSTRACT

Provided herein are molecules having an antigen binding fragment that immunospecifically binds to BTN1A1, such as anti-BTN1A1 antibodies. These molecules include those having an antigen binding fragment that immunospecifically binds to glycosylated BTN1A1, such as anti-glycosylated BTN1A1 antibodies. Methods of making and using these molecules are also provided, including methods of using them in cancer therapies, or as cancer diagnostics.

13 Claims, 23 Drawing Sheets

Figure 1:
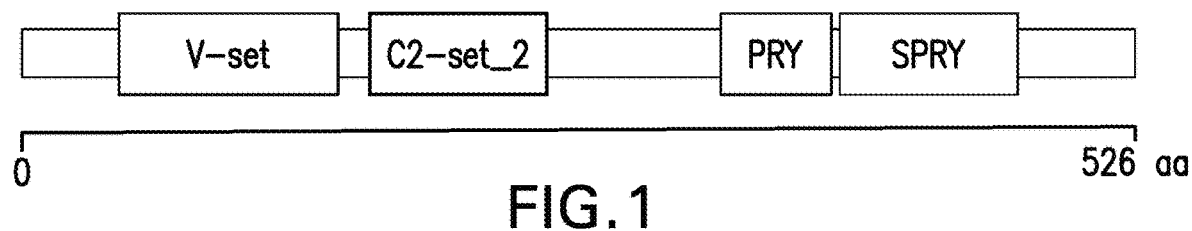

Specification includes a Sequence Listing.

(56) References Cited

OTHER PUBLICATIONS

Steffer et al., "Butyrophilin, a milk protein, modulates the encephalitogenic T cell response to myelin oligodendrocyte glycoprotein in experimental autoimmune encephalomyelitis," *J. Immunol.*, 165(5):2859-2865 (2000).

Taylor et al., "Cloning and sequence analysis of human butyrophilin reveals a potential receptor function," *Biochim. Biophys. Acta.*, 1306(1):1-4 (1996).

\* cited by examiner

MAVFPSSGLPRCLLTLILLQLPKLDSAPFDVIGPPEPILAVVGE
DAELPCRLSP NAS AEHLELRWFRKKVSPAVLVHRDGREQEAEQMPEYRGRATLVQDGI
AKGRVALRIRGVRVSDDGEYTCFFREDGSYEEALVHLKVAALGSDPHISMQVQENGEI
CLECTSVGWYPEPQVQWRTSKGEKFPSTSESRNPDEEGLFTVAASVIIRDTSTK NVS C
YIQNLLLGQEKKVEISIPASSLPRLTPWIVAVAVILMVLGLLTIGSIFFTWRLYNERP
RERRNEFSSKERLLEELKWKKATLHAVDVTLDPDTAHPHLFLYEDSKSVRLEDSRQKL
PEKTERFDSWPCVLGRETFTSGRHYWEVEVGDRTDWAIGVCRENVMKKGFDPMTPENG
FWAVELYGNGYWALTPLRTPLPLAGPPRRVGIFLDYESGDISFYNMNDGSDIYTFS NV
T FSGPLRPFFCLWSSGKKPLTICPIADGPERVTVIANAQDLSKEIPLSPMGEESAPRD
ADTLHSKLIPTQPSQGAP

FIG.5

RLSPNASAEH (N55) (*Homo sapiens*)
GFSPNASSEY (N56) (*Mus musculus*)
RLSPNVSAKG (N55) (*Bos taurus*)

TSAKNVSCYI (N215) (*Homo sapiens*)
SSIKNMSCCI (N216) (*Mus musculus*)
SSMKNVSCCI (N215) (*Bos taurus*)

FIG.6

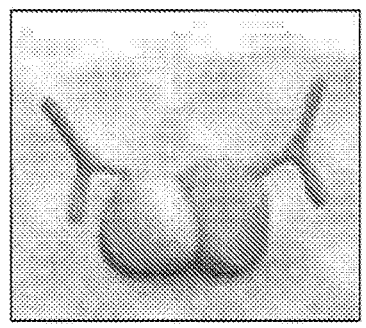 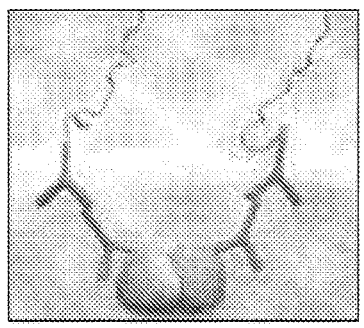 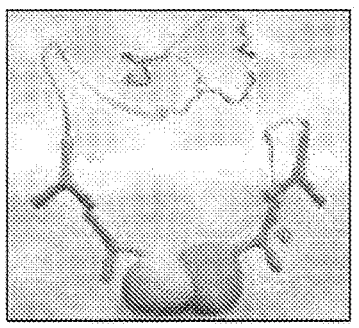
1. Incubate with target primary antibodies
2. Add PLA probes PLUS and MINUS
3. Hybridize connector oligos
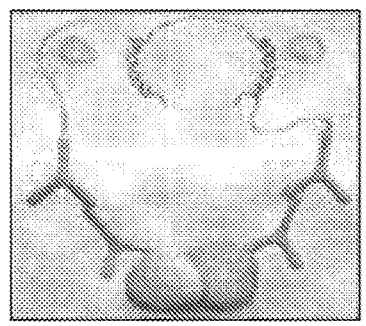 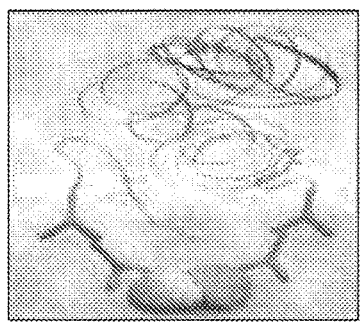 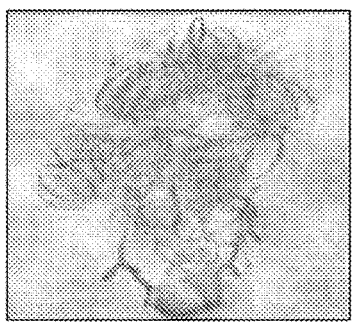
4. Ligation to form a complete DNA circle
5. Rolling circle amplification
6. Add fluorescent probes to reveal interaction
FIG. 19

SEQUENCE LISTING

```
<160> NUMBER OF SEQ ID NOS: 55

<210> SEQ ID NO 1
<211> LENGTH: 526
<212> TYPE: PRT
<213> ORGANISM: Homo sapiens

<400> SEQUENCE: 1

Met Ala Val Phe Pro Ser Ser Gly Leu Pro Arg Cys Leu Leu Thr Leu
1               5                   10                  15

Ile Leu Leu Gln Leu Pro Lys Leu Asp Ser Ala Pro Phe Asp Val Ile
            20                  25                  30

Gly Pro Pro Glu Pro Ile Leu Ala Val Val Gly Glu Asp Ala Lys Leu
        35                  40                  45

Pro Cys Arg Leu Ser Pro Asn Ala Ser Ala Glu His Leu Glu Leu Arg
    50                  55                  60

Trp Phe Arg Lys Lys Val Ser Pro Ala Val Leu Val His Arg Asp Gly
65                  70                  75                  80

Arg Glu Gln Glu Ala Glu Gln Met Pro Glu Tyr Arg Gly Arg Ala Thr
                85                  90                  95

Leu Val Gln Asp Gly Ile Ala Lys Gly Arg Val Ala Leu Arg Ile Arg
            100                 105                 110

Gly Val Arg Val Ser Asp Asp Gly Glu Tyr Thr Cys Phe Phe Arg Glu
        115                 120                 125

Asp Gly Ser Tyr Glu Glu Ala Leu Val His Leu Lys Val Ala Ala Leu
    130                 135                 140

Gly Ser Asp Pro His Ile Ser Met Gln Val Gln Glu Asn Gly Glu Ile
145                 150                 155                 160

Cys Leu Glu Cys Thr Ser Val Gly Trp Tyr Pro Glu Pro Gln Val Gln
                165                 170                 175

Trp Arg Thr Ser Lys Gly Glu Lys Phe Pro Ser Thr Ser Glu Ser Arg
            180                 185                 190

Asn Pro Asp Glu Glu Gly Leu Phe Thr Val Ala Ala Ser Val Ile Ile
        195                 200                 205

Arg Asp Thr Ser Ala Lys Asn Val Ser Cys Tyr Ile Gln Asn Leu Leu
    210                 215                 220

Leu Gly Gln Glu Lys Lys Val Glu Ile Ser Ile Pro Ala Ser Ser Leu
```

|  |  |  | 225 |  |  |  | 230 |  |  |  | 235 |  |  |  | 240 |
|---|---|---|---|---|---|---|---|---|---|---|---|---|---|---|---|

Pro Arg Leu Thr Pro Trp Ile Val Ala Val Ala Val Ile Leu Met Val
            245                 250                 255

Leu Gly Leu Leu Thr Ile Gly Ser Ile Phe Phe Thr Trp Arg Leu Tyr
            260                 265                 270

Asn Glu Arg Pro Arg Glu Arg Asn Glu Phe Ser Ser Lys Glu Arg
            275                 280             285

Leu Leu Glu Glu Leu Lys Trp Lys Lys Ala Thr Leu His Ala Val Asp
            290                 295                 300

Val Thr Leu Asp Pro Asp Thr Ala His Pro His Leu Phe Leu Tyr Glu
305                 310                 315                 320

Asp Ser Lys Ser Val Arg Leu Glu Asp Ser Arg Gln Lys Leu Pro Glu
            325                 330                 335

Lys Thr Glu Arg Phe Asp Ser Trp Pro Cys Val Leu Gly Arg Glu Thr
            340                 345                 350

Phe Thr Ser Gly Arg His Tyr Trp Glu Val Glu Val Gly Asp Arg Thr
            355                 360                 365

Asp Trp Ala Ile Gly Val Cys Arg Glu Asn Val Met Lys Lys Gly Phe
370                 375                 380

Asp Pro Met Thr Pro Glu Asn Gly Phe Trp Ala Val Glu Leu Tyr Gly
385                 390                 395                 400

Asn Gly Tyr Trp Ala Leu Thr Pro Leu Arg Thr Pro Leu Pro Leu Ala
            405                 410                 415

Gly Pro Pro Arg Arg Val Gly Ile Phe Leu Asp Tyr Glu Ser Gly Asp
            420                 425                 430

Ile Ser Phe Tyr Asn Met Asn Asp Gly Ser Asp Ile Tyr Thr Phe Ser
            435                 440                 445

Asn Val Thr Phe Ser Gly Pro Leu Arg Pro Phe Phe Cys Leu Trp Ser
            450                 455                 460

Ser Gly Lys Lys Pro Leu Thr Ile Cys Pro Ile Ala Asp Gly Pro Glu
465                 470                 475                 480

Arg Val Thr Val Ile Ala Asn Ala Gln Asp Leu Ser Lys Glu Ile Pro
            485                 490                 495

Leu Ser Pro Met Gly Glu Asp Ser Ala Pro Arg Asp Ala Asp Thr Leu
            500                 505                 510

His Ser Lys Leu Ile Pro Thr Gln Pro Ser Gln Gly Ala Pro
            515                 520                 525

<210> SEQ ID NO 2
<211> LENGTH: 1581
<212> TYPE: DNA
<213> ORGANISM: Homo sapiens

<400> SEQUENCE: 2

| atggcagttt | tcccaagctc | cggtctcccc | agatgtctgc | tcaccctcat | tctcctccag | 60 |
| ctgcccaaac | tggattcagc | tccctttgac | gtgattggac | ccccggagcc | catcctggcc | 120 |
| gttgtgggtg | aggacgccaa | gctgccctgt | cgcctgtctc | gaacgcgag | cgccgagcac | 180 |
| ttggagctac | gctggttccg | aaagaaggtt | tcgccggccg | tgctggtgca | tagggacggg | 240 |
| cgcgagcagg | aagccgagca | gatgcccgag | taccgcgggc | gggcgacgct | ggtccaggac | 300 |
| ggcatcgcca | aggggcgcgt | ggccttgagg | atccgtggcg | tcagagtctc | tgacgacggg | 360 |
| gagtacacgt | gcttttttcag | ggaggatgga | agctacgaag | aagccctggt | gcatctgaag | 420 |
| gtggctgctc | tgggctctga | ccctcacatc | agtatgcaag | ttcaagagaa | tggagaaatc | 480 |

-continued

```
tgtctggagt gcacctcagt gggatggtac ccagagcccc aggtgcagtg gagaacttcc    540
aagggagaga agtttccatc tacatcagag tccaggaatc ctgatgaaga aggtttgttc    600
actgtggctg cttcagtgat catcagagac acttctgcga aaaatgtgtc ctgctacatc    660
cagaatctcc ttcttggcca ggagaagaaa gtagaaatat ccataccagc ttcctccctc    720
ccaaggctga ctccctggat agtggctgtg gctgtcatcc tgatggttct aggacttctc    780
accattgggt ccatattttt cacttggaga ctatacaacg aaagacccag agagaggagg    840
aatgaattca gctctaaaga gagactcctg gaagaactca atggaaaaa ggctaccttg    900 catgcagttg atgtgactct ggacccagac acagctcatc cccacctctt tctttatgag    960
gattcaaaat ctgttcgact ggaagattca cgtcagaaac tgcctgagaa aacagagaga   1020
tttgactcct ggccctgtgt gttgggccgt gagaccttca cctcaggaag cattactgg    1080 gaggtggagg tgggagacag gactgactgg gcaatcggcg tgtgtaggga gaatgtgatg   1140
aagaaaggat ttgaccccat gactcctgag aatgggttct gggctgtaga gttgtatgga   1200
aatgggtact gggccctcac tcctctccgg accctctcc cattggcagg ccccacgc     1260 cgggttggga ttttcctaga ctatgaatca ggagacatct ccttctacaa catgaatgat   1320
ggatctgata tctatacttt ctccaatgtc actttctctg gcccctccg gcccttcttt   1380 tgcctatggt ctagcggtaa aaagcccctg accatctgcc caattgctga tgggcctgag   1440
agggtcacag tcattgctaa tgcccaggac ctttctaagg agatcccatt gtcccccatg   1500
ggggaggact ctgcccctag ggatgcagac actctccatt ctaagctaat ccctaccccaa  1560 cccagccaag gggcaccta a                                              1581
```

<210> SEQ ID NO 3
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr His Tyr
            20                  25                  30

Asn Met Asp Trp Val Lys Gln Ser His Gly Lys Ser Leu Glu Trp Ile
        35                  40                  45

Gly Tyr Ile Tyr Pro Ser Asn Gly Gly Thr Gly Tyr Asn Gln Lys Phe
    50                  55                  60

Lys Ser Arg Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Gly Ala Tyr His Tyr Gly Ser Ser Tyr Ala Tyr Trp Tyr Phe
            100                 105                 110

Asp Val Trp Gly Ala Gly Thr Thr Val Thr Val Ser Ser
        115                 120                 125
```

<210> SEQ ID NO 4
<211> LENGTH: 375
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
gaggtccagc tgcagcagtc tggacctgag ctggtgaagc ctggggcttc agtgaagata      60
tcctgcaagg cttctggata cacattcact cactacaaca tggactgggt gaagcagagc     120
catggaaaga gccttgaatg gattggatat atttatcctt ccaatggtgg tactggctac     180
aaccagaaat tcaagagcag ggccacattg actgtagaca gtcctccag cacagcctac      240 atggaactcc acagcctgac atctgaggac tctgcagtct attactgtgc aagaggggcc     300
tatcactacg gtagttccta cgcctactgg tacttcgatg tctggggcgc agggaccacg     360
gtcaccgtct cctca                                                      375

<210> SEQ ID NO 5
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Ser Asn Tyr
            20                  25                  30

Leu Asn Trp Tyr Gln Gln Lys Pro Asp Glu Thr Val Lys Leu Leu Ile
        35                  40                  45

Ser Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Ala Pro
65                  70                  75                  80

Glu Asp Ile Ala Thr Tyr Tyr Cys Gln Gln Ser Ser Lys Leu Pro Phe
                85                  90                  95

Thr Phe Gly Ser Gly Thr Glu Leu Glu Ile Lys Arg Ala
            100                 105

<210> SEQ ID NO 6
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
gatatccaga tgacacagac tacatcctcc ctgtctgcct ctctgggaga cagagtcacc      60
atcagttgca gtgcaagtca ggacattagc aattatttaa actggtatca gcagaaacca    120
gatgaaactg ttaaactcct gatctcttac acatcaagtt tacactcagg agtcccatca    180
agattcagtg gcagtgggtc tgggacagat tattctctca ccatcagcaa cctggcacct    240
gaagatattg ccacttacta ttgtcagcag tctagtaagc ttccattcac gttcggctcg    300
gggacagagt tggaaataaa acgggct                                         327
```

```
<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Tyr Thr Phe Thr His Tyr
1               5

<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Tyr Pro Ser Asn Gly Gly
1               5

<210> SEQ ID NO 9
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Ala Tyr His Tyr Gly Ser Ser Tyr Ala Tyr Trp Tyr Phe Asp Val
1               5                   10                  15

<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Tyr Thr Phe Thr His Tyr Asn Met Asp
1               5                   10

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Tyr Ile Tyr Pro Ser Asn Gly Gly Thr Gly
1               5                   10

<210> SEQ ID NO 12
<211> LENGTH: 16
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Ala Tyr His Tyr Gly Ser Ser Tyr Ala Tyr Trp Tyr Phe Asp Val
1               5                   10                  15

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

His Tyr Asn Met Asp
1               5

<210> SEQ ID NO 14
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Tyr Ile Tyr Pro Ser Asn Gly Gly Thr Gly Tyr Asn Gln Lys Phe Lys
1               5                   10                  15

Ser

<210> SEQ ID NO 15
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Ala Tyr His Tyr Gly Ser Ser Tyr Ala Tyr Trp Tyr Phe Asp Val
1               5                   10                  15

<210> SEQ ID NO 16
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Thr His Tyr Asn Met Asp
1               5

<210> SEQ ID NO 17
<211> LENGTH: 13
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 17

Trp Ile Gly Tyr Ile Tyr Pro Ser Asn Gly Gly Thr Gly
1               5                   10

<210> SEQ ID NO 18
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ala Arg Gly Ala Tyr His Tyr Gly Ser Ser Tyr Ala Tyr Trp Tyr Phe
1               5                   10                  15

Asp

<210> SEQ ID NO 19
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Ala Ser Gln Asp Ile Ser Asn Tyr Leu Asn
1               5                   10

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Tyr Thr Ser Ser Leu His Ser
1               5

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln Gln Ser Ser Lys Leu Pro Phe Thr
1               5

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 22

Ser Ala Ser Gln Asp Ile Ser Asn Tyr Leu Asn
1               5                   10

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Tyr Thr Ser Ser Leu His Ser
1               5

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gln Gln Ser Ser Lys Leu Pro Phe Thr
1               5

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ser Ala Ser Gln Asp Ile Ser Asn Tyr Leu Asn
1               5                   10

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Tyr Thr Ser Ser Leu His Ser
1               5

<210> SEQ ID NO 27
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

```
Gln Gln Ser Ser Lys Leu Pro Phe Thr
1               5
```

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

```
Ser Asn Tyr Leu Asn Trp Tyr
1               5
```

<210> SEQ ID NO 29
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

```
Leu Leu Ile Ser Tyr Thr Ser Ser Leu His
1               5                   10
```

<210> SEQ ID NO 30
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

```
Gln Gln Ser Ser Lys Leu Pro Phe
1               5
```

<210> SEQ ID NO 31
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

```
Arg Lys Lys Val Ser Pro Ala Val Leu
1               5
```

<210> SEQ ID NO 32
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

```
Thr Val Ala Ala Ser Val Ile Ile Arg Asp Thr Ser Ala Lys Asn Val
1               5                   10                  15

Ser Cys Tyr
```

```
<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ile Arg Asp Thr Ser Ala Lys Asn
1               5

<210> SEQ ID NO 34
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Leu Glu Leu Arg Trp Phe Arg Lys Lys Val Ser Pro Ala
1               5                   10

<210> SEQ ID NO 35
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Glu Glu Gly Leu Phe Thr Val Ala Ala Ser Val Ile Ile Arg Asp Thr
1               5                   10                  15

Ser Ala Lys Asn Val
            20

<210> SEQ ID NO 36
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ala Thr Leu Val Gln Asp Gly Ile Ala Lys Gly Arg
1               5                   10

<210> SEQ ID NO 37
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Asn Pro Asp Glu Glu Gly Leu Phe Thr Val Ala Ala Ser Val Ile Ile
1               5                   10                  15
```

```
Arg Asp Thr Ser Ala Lys
            20

<210> SEQ ID NO 38
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Thr Val Ala Ala Ser Val Ile Ile Arg Asp Thr Ser Ala Lys Asn Val
1               5                   10                  15

Ser Cys Tyr

<210> SEQ ID NO 39
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any amino acid

<400> SEQUENCE: 39

Ala Glu Gln Xaa Pro Glu Tyr Arg Gly Arg Ala Thr
1               5                   10

<210> SEQ ID NO 40
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gly Arg Ala Thr Leu Val Gln Asp Gly Ile Ala Lys Gly Arg Val
1               5                   10                  15

<210> SEQ ID NO 41
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Glu Glu Gly Leu Phe Thr Val Ala Ala Ser Val Ile Ile Arg Asp Thr
1               5                   10                  15

Ser Ala Lys Asn Val
            20

<210> SEQ ID NO 42
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 42

Tyr Cys Ala Arg Gly Ala Tyr
1               5

<210> SEQ ID NO 43
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Thr Phe Thr His Tyr
1               5

<210> SEQ ID NO 44
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Phe Thr Phe Gly Ser Gly Thr Glu
1               5

<210> SEQ ID NO 45
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ser Leu Glu Trp Ile Gly Tyr Ile Tyr Pro Ser Asn Gly Gly Thr Gly
1               5                   10                  15

Tyr Asn Gln Lys Phe Lys Ser Arg
            20

<210> SEQ ID NO 46
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Leu Leu Ile Ser Tyr Thr Ser Ser Leu His Ser Gly Val Pro Ser Arg
1               5                   10                  15

<210> SEQ ID NO 47
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
```

```
         Synthetic peptide"

<400> SEQUENCE: 47

Thr Phe Thr His Tyr
1               5

<210> SEQ ID NO 48
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Leu His Ser Gly Val Pro Ser Arg
1               5

<210> SEQ ID NO 49
<211> LENGTH: 10
<212> TYPE: PRT
<213> ORGANISM: Homo sapiens

<400> SEQUENCE: 49

Arg Leu Ser Pro Asn Ala Ser Ala Glu His
1               5                  10

<210> SEQ ID NO 50
<211> LENGTH: 10
<212> TYPE: PRT
<213> ORGANISM: Mus musculus

<400> SEQUENCE: 50

Gly Phe Ser Pro Asn Ala Ser Ser Glu Tyr
1               5                  10

<210> SEQ ID NO 51
<211> LENGTH: 10
<212> TYPE: PRT
<213> ORGANISM: Bos taurus

<400> SEQUENCE: 51

Arg Leu Ser Pro Asn Val Ser Ala Lys Gly
1               5                  10

<210> SEQ ID NO 52
<211> LENGTH: 10
<212> TYPE: PRT
<213> ORGANISM: Homo sapiens

<400> SEQUENCE: 52

Thr Ser Ala Lys Asn Val Ser Cys Tyr Ile
1               5                  10

<210> SEQ ID NO 53
<211> LENGTH: 10
<212> TYPE: PRT
<213> ORGANISM: Mus musculus

<400> SEQUENCE: 53

Ser Ser Ile Lys Asn Met Ser Cys Cys Ile
1               5                  10

<210> SEQ ID NO 54
```

```
<211> LENGTH: 10
<212> TYPE: PRT
<213> ORGANISM: Bos taurus

<400> SEQUENCE: 54

Ser Ser Met Lys Asn Val Ser Cys Cys Ile
1               5                   10

<210> SEQ ID NO 55
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 55

His His His His His His
1               5
```

ANTIBODIES AND MOLECULES THAT IMMUNOSPECIFICALLY BIND TO BTN1A1 AND THE THERAPEUTIC USES THEREOF

CROSS REFERENCE TO RELATED APPLICATIONS

This Application is a divisional of U.S. application Ser. No. 15/781,071, filed Jun. 1, 2018, which is the U.S. national stage application of the International Application No. PCT/US2016/064436, filed Dec. 1, 2016, which claims the benefit of priority to U.S. Provisional Application No. 62/262,309, filed on Dec. 2, 2015, the content of each of which are incorporated by reference in their entirety.

1. FIELD

The present invention relates in general to the field of cancer immunology and molecular biology. Provided herein are anti-BTN1A1 antibodies or other molecules having an antigen binding fragment that immunospecifically bind to BTN1A1, as well as the therapeutic uses thereof.

2. BACKGROUND

The immune system of humans and other mammals protects them against infections and diseases. A number of stimulatory and inhibitory ligands and receptors provide a tight control system to maximize immune response against infection while limiting self-immunity. Recently, therapeutics that modulate immune response, such as anti-PD1 or anti-PDL1 antibodies, were found to be effective in some cancer treatments. However, development of new therapeutics that safely and effectively treat diseases by modulating the immune system remain an urgent need, especially for metastatic cancers. The compositions and methods described herein meet these needs and provide other related advantages.

3. SUMMARY

Provided herein are molecules having an antigen binding fragment that immunospecifically binds to BTN1A1. In some embodiments, the molecules are anti-BTN1A1 antibodies.

In some embodiments, the molecules have an antigen binding fragment that immunospecifically binds to glycosylated BTN1A1. In some aspects, the antigen binding fragments immunospecifically bind to BTN1A1 glycosylated at positions N55, N215, and/or N449. In some aspects, the antigen binding fragments immunospecifically bind to BTN1A1 glycosylated at position N55. In some aspects, the antigen binding fragments immunospecifically bind to BTN1A1 glycosylated at position N215. In some aspects, the antigen binding fragments immunospecifically bind to BTN1A1 glycosylated at position N449. In some aspects, the antigen binding fragments immunospecifically bind to one or more glycosylation motifs. In some aspects, the antigen binding fragments immunospecifically bind to BTN1A1 glycosylated at positions N55 and N215. In some aspects, the antigen binding fragments immunospecifically bind to BTN1A1 glycosylated at positions N215 and N449. In some aspects, the antigen binding fragments immunospecifically bind to BTN1A1 glycosylated at positions N55 and N449. In some aspects, the antigen binding fragments immunospecifically bind to BTN1A1 glycosylated at positions N55, N215 and N449.

In some embodiments, the molecules have an antigen binding fragment that immunospecifically binds to glycosylated BTN1A1, wherein the antigen binding fragment preferentially binds to glycosylated BTN1A1 over non-glycosylated BTN1A1. In some aspects, the antigen binding fragments preferentially bind to BTN1A1 glycosylated at positions N55, N215, and/or N449 over non-glycosylated BTN1A1. In some aspects, the antigen binding fragments preferentially bind to BTN1A1 glycosylated at position N55 over non-glycosylated BTN1A1. In some aspects, the antigen binding fragments preferentially bind to BTN1A1 glycosylated at position N215 over non-glycosylated BTN1A1. In some aspects, the antigen binding fragments preferentially bind to BTN1A1 glycosylated at position N449 over non-glycosylated BTN1A1. In some aspects, the antigen binding fragments preferentially bind to one or more glycosylation motifs. In some aspects, the antigen binding fragments preferentially bind to BTN1A1 glycosylated at positions N55 and N215 over non-glycosylated BTN1A1. In some aspects, the antigen binding fragments preferentially bind to BTN1A1 glycosylated at positions N215 and N449 over non-glycosylated BTN1A1. In some aspects, the antigen binding fragments preferentially bind to BTN1A1 glycosylated at positions N55 and N449 over non-glycosylated BTN1A1. In some aspects, the antigen binding fragments preferentially bind to BTN1A1 glycosylated at positions N55, N215 and N449 over non-glycosylated BTN1A1.

In some embodiments, the antigen binding fragment binds to glycosylated BTN1A1 with Kd less than half of the Kd exhibited relative to unglycosylated BTN1A1. In some embodiments, the antigen binding fragment binds to glycosylated BTN1A1 with Kd at least 10 times less than the Kd exhibited relative to unglycosylated BTN1A1.

In some embodiments, the antigen binding fragment binds to glycosylated BTN1A1 with a fluorescence intensity (MFI) that is at least twice as high as the MFI as exhibited relative to unglycosylated BTN1A1. In some embodiments, the antigen binding fragment binds to glycosylated BTN1A1 with an MFI that is at least five times as high as the MFI as exhibited relative to unglycosylated BTN1A1.

In some aspects, the antigen binding fragments immunospecifically mask BTN1A1 glycosylation at positions N55, N215, and/or N449. In some aspects, the antigen binding fragments immunospecifically mask BTN1A1 glycosylation at position N55. In some aspects, the antigen binding fragments immunospecifically mask BTN1A1 glycosylation at position N215. In some aspects, the antigen binding fragments immunospecifically mask BTN1A1 glycosylation at position N449. In some aspects, the antigen binding fragments immunospecifically mask one or more glycosylation motifs of BTN1A1. In some aspects, the antigen binding fragments immunospecifically mask BTN1A1 glycosylation at positions N55 and N215. In some aspects, the antigen binding fragments immunospecifically mask BTN1A1 glycosylation at positions N215 and N449. In some aspects, the antigen binding fragments immunospecifically mask BTN1A1 glycosylation at positions N55 and N449. In some aspects, the antigen binding fragments immunospecifically mask BTN1A1 glycosylation at positions N55, N215 and N449.

In some embodiments, provided herein are molecules having an antigen binding fragment that immunospecifically binds to BTN1A1 and comprises the VH or VL domain of the murine monoclonal antibody STC810, as depicted in Table 2. In one embodiment, the molecules can have an antigen binding fragment that comprises both the VH and VL domain of the murine monoclonal antibody STC810, as depicted in Table 2. In another embodiment, the molecules can have an antigen binding fragment that comprises one or more VH CDRs having the amino acid sequence of any one of the VH CDRs of the murine monoclonal antibody STC810, as depicted in Table 2. In another embodiment, the molecules can have antigen binding fragment that comprises one or more VL CDRs having the amino acid sequence of any one of the VL CDRs of the murine monoclonal antibody STC810, as depicted in Table 2. In yet another embodiment, the molecules can have antigen binding fragment that comprises at least one VH CDR and at least one VL CDR of the murine monoclonal antibody STC810, as depicted in Table 2.

In some embodiments, the molecules provided herein have an antigen binding fragment comprising: (a) a heavy chain variable ($V_H$) region comprising: (1) a $V_H$ CDR1 having an amino acid sequence selected from the group consisting of SEQ ID NOS: 7, 10, 13 and 16; (2) a $V_H$ CDR2 having an amino acid sequence selected from the group consisting of SEQ ID NOS: 8, 11, 14 and 17; and (3) a $V_H$ CDR3 having an amino acid sequence selected from the group consisting of SEQ ID NOS: 9, 12, 15 and 18; or (b) a light chain variable ($V_L$) region comprising: (1) a $V_L$ CDR1 having an amino acid sequence selected from the group consisting of SEQ ID NOS: 19, 22, 25 and 28; (2) a $V_L$ CDR2 having an amino acid sequence selected from the group consisting of SEQ ID NOS: 20, 23, 26 and 29; and (3) a $V_L$ CDR3 having an amino acid sequence selected from the group consisting of SEQ ID NOS: 21, 24, 27 and 30.

Also provided herein are isolated nucleic acid molecules encoding a VH chain, VL chain, VH domain, VL domain, VH CDR1, VH CDR2, VH CDR3, VL CDR1, VL CDR2, and/or VL CDR3 of anti-BTN1A1 antibodies described herein. Further provided are vectors and host cells comprising these nucleic acid molecules.

In some embodiments, molecules provided herein have an antigen binding fragment that competitively blocks (e.g., in a dose-dependent manner) a BTN1A1 epitope described herein. The BTN1A1 epitope can be an epitope of STC810 as described herein. In some embodiments, the molecules can have an antigen binding fragment that immunospecifically binds to an epitope of BTN1A1 as described herein. The BTN1A1 epitope can be an epitope of STC810 as described herein. In some embodiments, the BTN1A1 epitope has at least five consecutive amino acids of an amino acid sequence of SEQ ID NOS: 31-41.

In some embodiments, the molecules having an antigen binding fragment that immunospecifically binds to BTN1A1 are anti-BTN1A1 antibodies, including anti-glycosylated BTN1A1 antibodies. The antibodies can be monoclonal antibodies. The antibodies can be humanized antibodies. The antibodies can be human antibodies. The antibodies can be IgG, IgM, or IgA.

In some embodiments, the molecule having an antigen binding fragment that immunospecifically binds to BTN1A1 is a Fab', a F(ab')2, a F(ab')3, a monovalent scFv, a bivalent scFv, or a single domain antibody.

In some embodiments, the molecules having an antigen binding fragment that immunospecifically binds to BTN1A1 are recombinantly produced. In some embodiments, the molecule is conjugated to an imaging agent, a chemotherapeutic agent, a toxin or a radionuclide.

Also provided herein are compositions that comprises a molecule having an antigen binding fragment that immunospecifically binds to BTN1A1, as well as a pharmaceutically acceptable carrier. Further provided herein are kits that include a molecule having an antigen binding fragment that immunospecifically binds to BTN1A1, as well as an ancillary agent.

Also provided herein are antibody-drug conjugates (ADC) that include molecules having an antigen binding fragment that immunospecifically binds to BTN1A1 as described herein. Also provided herein are methods of using molecules provided herein to deliver a compound to a cell expressing BTN1A1 by contacting the cell with molecules provided herein conjugated with the compound. The compound can be an imaging agent, a therapeutic agent, a toxin or a radionuclide as described herein. The compound can be conjugated with anti-BTN1A1 antibody. The conjugate can be any conjugate as described herein, such as an ADC. The cell can be a cancer cell. The cell can also be a population of cells that include both cancer cells and normal cells.

Also provided herein are methods of modulating an immune response in a subject by administering an effective amount of the molecules described herein that have an antigen binding fragment that immunospecifically binds to BTN1A1, including anti-BTN1A1 antibodies. Modulating an immune response can include (a) increasing T cell activation; (b) increasing T cell proliferation; and/or (c) increasing cytokine production.

Also provided herein are methods of enhancing T-cell dependent apoptosis of a cell expressing BTN1A1 by contacting the cell with an effective amount of molecules described herein that have an antigen binding fragment that immunospecifically binds to BTN1A1, including anti-BTN1A1 antibodies. Also provided herein are methods of inhibiting the proliferation of cells expressing BTN1A1 by contacting the cell with an effective amount of molecules described herein that have an antigen binding fragment that immunospecifically binds to BTN1A1, including anti-BTN1A1 antibodies. The cells can be cancer cells.

Additionally, provided herein are methods of treating cancer in a subject by administrating to the subject an effective amount of a molecule having an antigen binding fragment that immunospecifically binds to BTN1A1 as described herein. In some embodiments, the molecule is an anti-BTN1A1 antibody. In some embodiments, the molecule is an anti-glycosylated BTN1A1 antibodies. In some embodiments, the treatment can activate an immune response, or promote the activation and proliferation of T cells in the subject. In some embodiments, the molecule binds to cancer cells and induces an immune response resulting in destruction of the cancer cells. In some embodiments, the destruction of cancer cells is mediated by ADCC activity of the molecules. In some embodiments, the destruction of cancer cells is mediated by CDC activity of the molecule.

In some embodiments, the subject has a metastatic cancer. The cancer can be a hematological cancer or a solid tumor. In some embodiments, the cancer is a hematological cancer selected from the group consisting of leukemia, lymphoma, and myeloma. In some embodiments, the cancer is a solid tumor selected from the group consisting of breast cancer, lung cancer, thymic cancer, thyroid cancer, head & neck cancer, prostate cancer, esophageal cancer, tracheal cancer, brain cancer, liver cancer, bladder cancer, kidney cancer, stomach cancer, pancreatic cancer, ovarian cancer, uterine cancer, cervical cancer, testicular cancer, colon cancer, rectal cancer and skin cancer. The skin cancer can be either melanomatous or non-melanomatous skin cancers.

In some embodiments, the methods include systematic administration to a subject of the molecules having an antigen binding fragment that immunospecifically binds BTN1A1 as described herein. In some embodiments, the molecule is administered intravenously, intradermally, intratumorally, intramuscularly, intraperitoneally, subcutaneously or locally. In some embodiments, the methods include administering a second anticancer therapy to the subject, which can be a surgical therapy, chemotherapy, biological targeted therapy, small molecular targeted therapy, radiation therapy, cryotherapy, hormonal therapy, immunotherapy or cytokine therapy.

4. BRIEF DESCRIPTION OF THE DRAWINGS

The following drawings form part of the present specification and are included to further demonstrate certain aspects of the present invention. The invention can be better understood by reference to one or more of these drawings in combination with the detailed description of specific embodiments presented herein.

FIG. 1—Linear structure of human BTN1A1. FIG. 1 depicts the linear structure of human BTN1A1, which includes two immunoglobulin domains (V-set, C2-set_2) and two protein interaction domains (PRY, SPRY).

Figure 2:

FIG. 2—Sub-cloning human BTN1A1. The entire coding sequence (CD) of human BTN1A1 with C-terminal flag tag was sub-cloned into pcDNA3 using standard cloning methodology. As depicted on FIG. 2, the upper band corresponds to the vector backbone, and the lower band corresponds to the CD of human BTN1A1 with flag tag.

Figure 3:
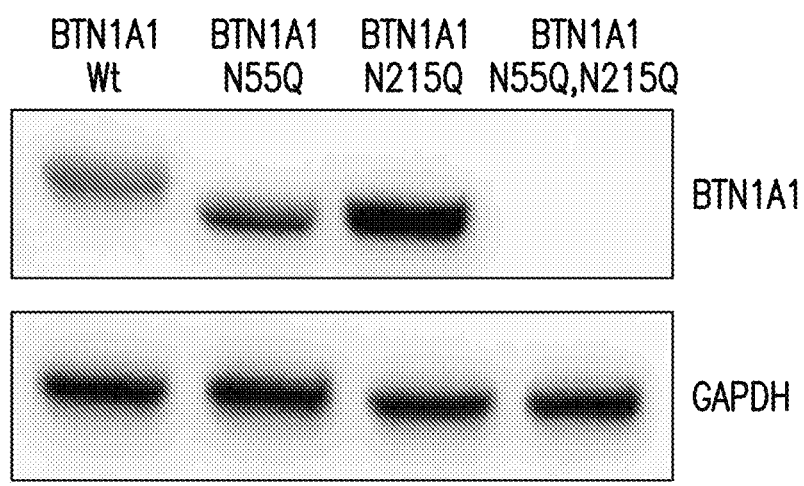

FIG. 3—Expression of glycosylation specific mutants and the wildtype BTN1A1 in 293T cells. Using site directed mutagenesis, specific mutations were made on the glycosylation sites in the extracellular domain of human BTN1A1 (N55Q, N215Q and the compound N55Q and N215Q). Expression of both the wildtype BTN1A1 and its mutant forms is depicted on FIG. 3. As shown, the compound mutant (N55Q and N215Q) of BTN1A1 failed to express, demonstrating that glycosylation of BTN1A1 is critical for its expression.

Figure 4:
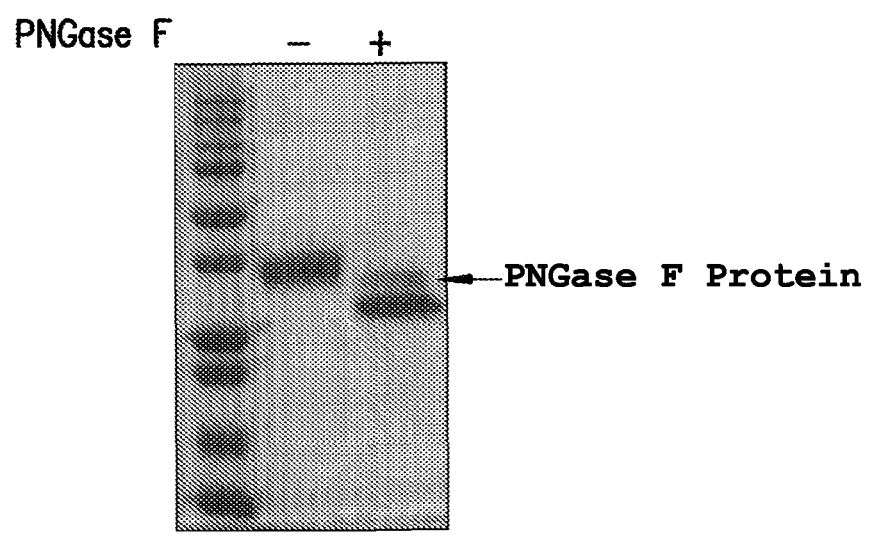

FIG. 4—BTN1A1 is N-linked glycosylated. Recombinant human BTN1A1 protein expressing the extracellular domain was treated with either mock (-) or PNGase F for an hour, subjected to polyacrylamide gel electrophoresis (PAGE) and coomassie stained. As depicted on FIG. 4, an obvious shift was observed in the PNGase F treated lane, indicating that the N-linked glycosylation of BTN1A1. The band corresponding to the arrow is PNGase F protein.

FIG. 5—Putative glycosylation sites in the full length human BTN1A1 protein. The full length sequence of human BTN1A1 (SEQ ID NO: 1) was entered into a N-linked glycosylation sites (Nx[ST] pattern predicting software (hiv-.lanl.gov/content/sequence/GLYCOSITE/glycosite.html). The three candidate glycosylated sites as identified by the software are highlighted in red in the sequence depicted on FIG. 5.

FIG. 6—High degree of homology in the glycosylation sites of the extracellular domains of BTN1A1. The verified BTN1A1 sequences from the three species (*Homo sapiens, Mus musculus* and *Bos taurus*) were collected from uniprot (uniport.org), subjected to the glycosylation site predicting software (hiv.lanl.gov/content/sequence/GLYCOSITE/glycosite.html) and aligned using clustal W2 (ebi.ac.uk/Tools/msa/clustalw2/). As depicted on FIG. 6, the glycosylations sites (SEQ ID NOS 49-54, respectively, in order of appearance) are evolutionarily conserved across species.

Figure 7A:
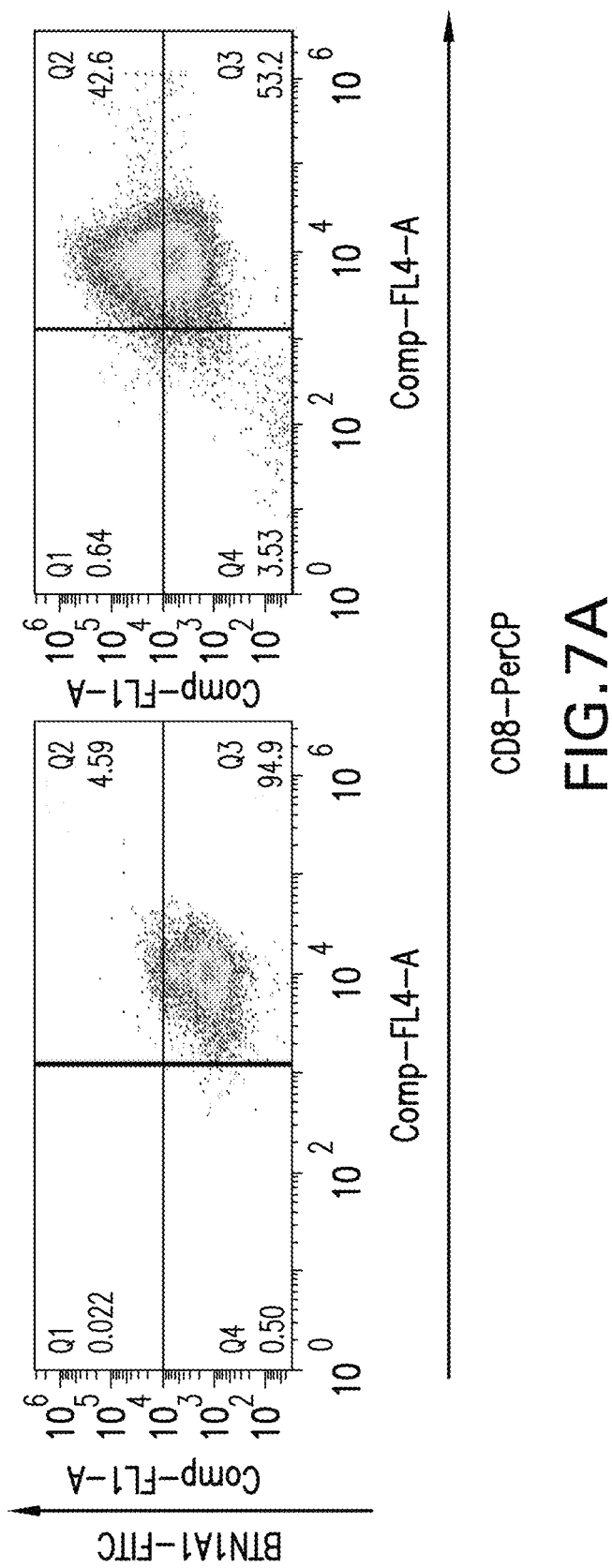

FIG. 7A—High induction of cell surface BTN1A1 in murine T cells following activation by anti CD3/CD28 stimulation. Naïve murine T cells were either mock stimulated (left) or stimulated with anti CD3 (5 ug/ml) and anti CD28 (5 ug/ml) for 2 days and subjected to flow cytometric analysis. FIG. 7A depicts the high induction of cell surface BTN1A1 in the CD3/CD28 stimulated cells compared to the mock treated cells.

Figure 7B:
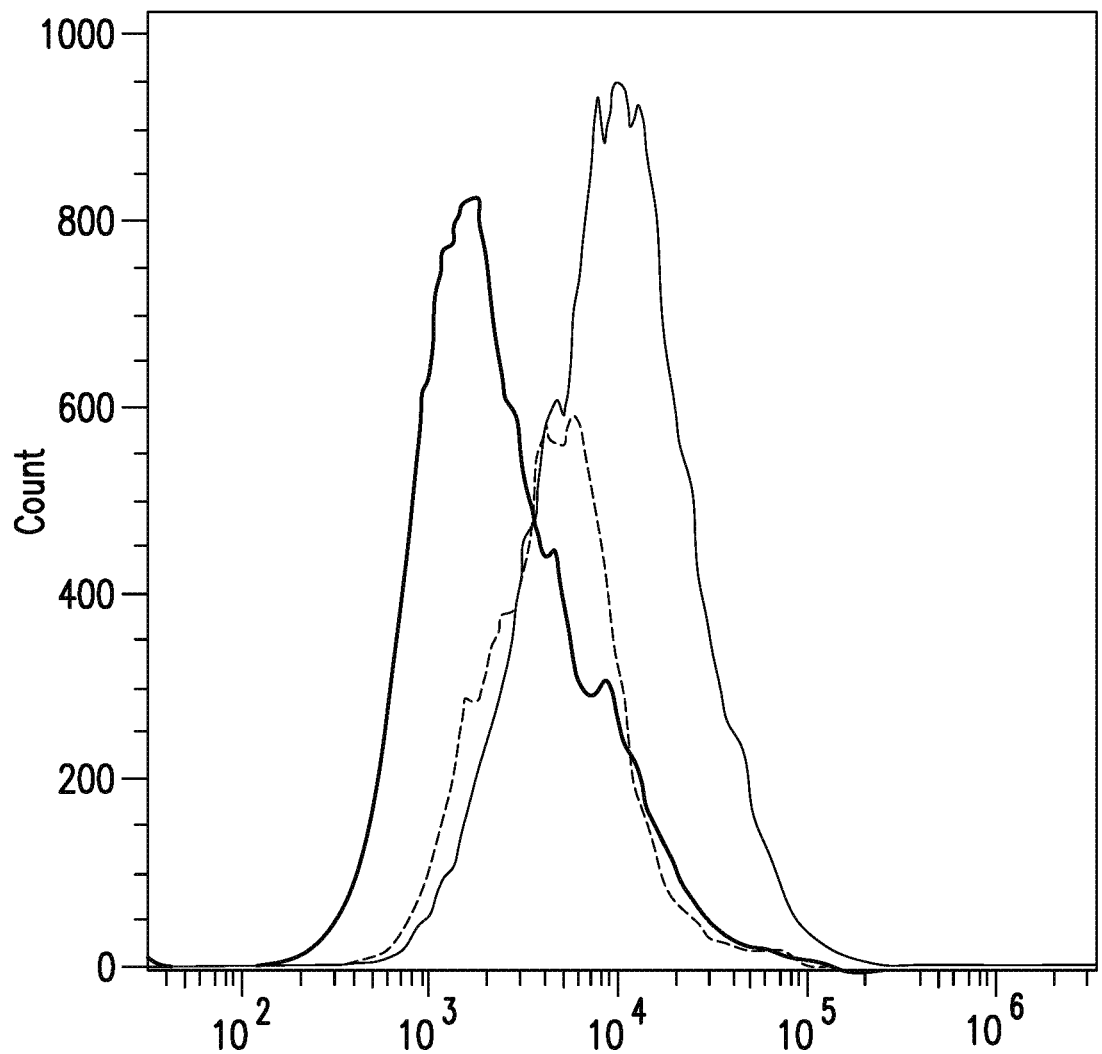

FIG. 7B—High induction of cell surface BTN1A1 in murine T cells following activation by anti CD3/CD28 stimulation. Naïve murine T cells were either mock stimulated (red) or stimulated with anti CD3-(5 ug/ml) and anti-CD28 (5 ug/ml) (orange) for 2 days and subjected to flow cytometry analysis. The expression of BTN1A1 was compared to the secondary antibody only control. FIG. 7B depicts the high induction of cell surface BTN1A1 in the CD3/CD28 stimulated cells compared to the mock treated cells. Blue curve is the isotype control.

Figure 8:
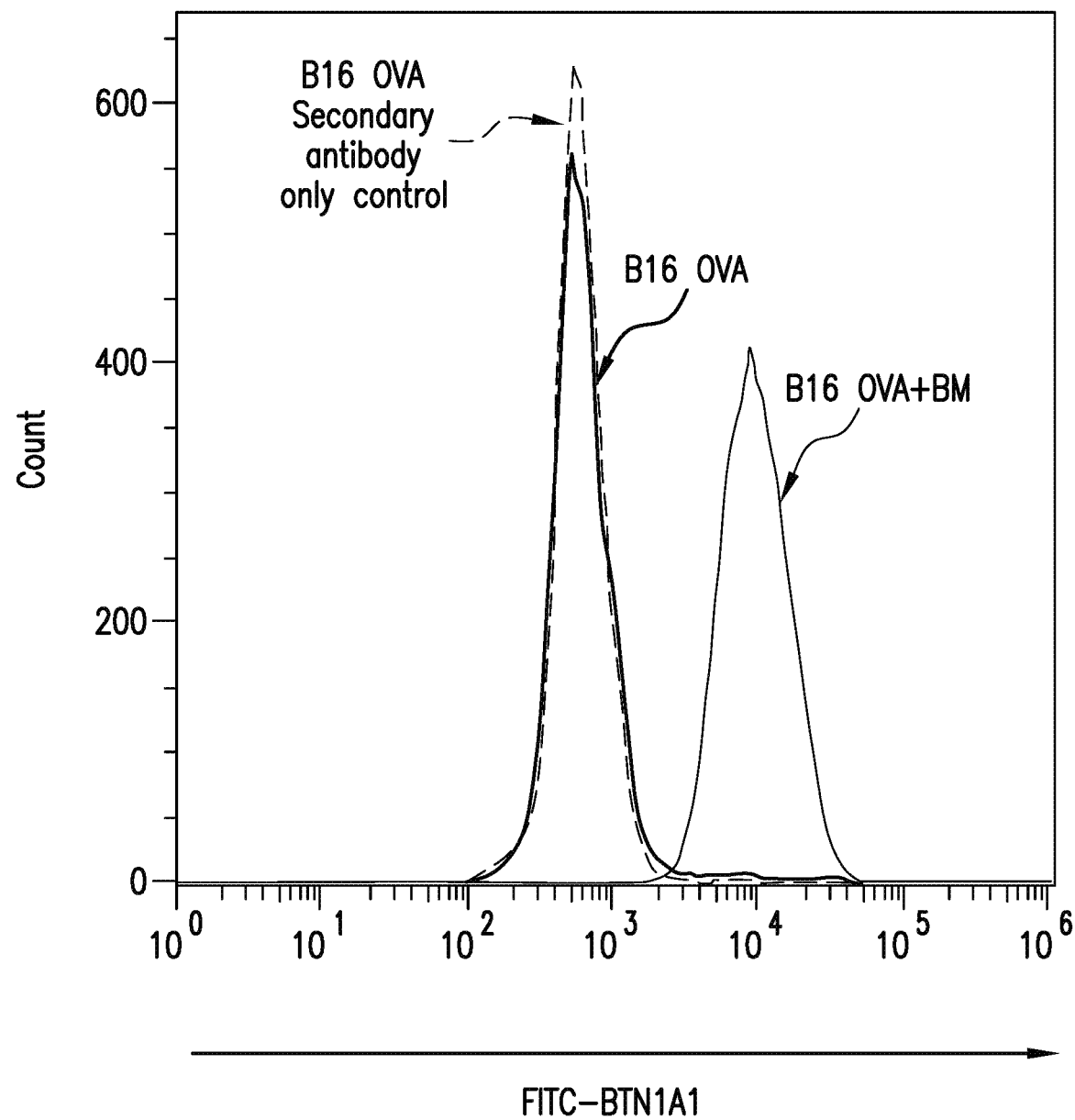

FIG. 8—Bone marrow cells induce BTN1A1 expression in B16-Ova melanoma cells. Extracellular BTN1A1 in B16-Ova cells was detected by staining with antibody only control or FITC-BTN1A1 antibody, and BTN1A1 expression level was examined using flow cytometry. The term "BM" stand for Bone Marrow.

Figure 9A:
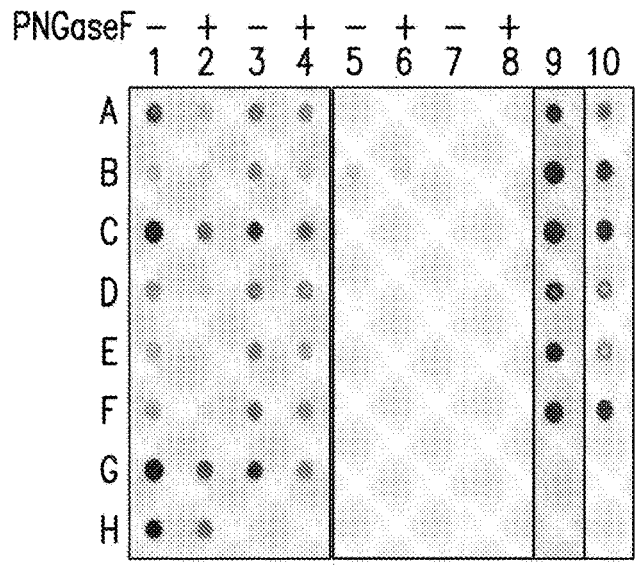
Figure 9B:
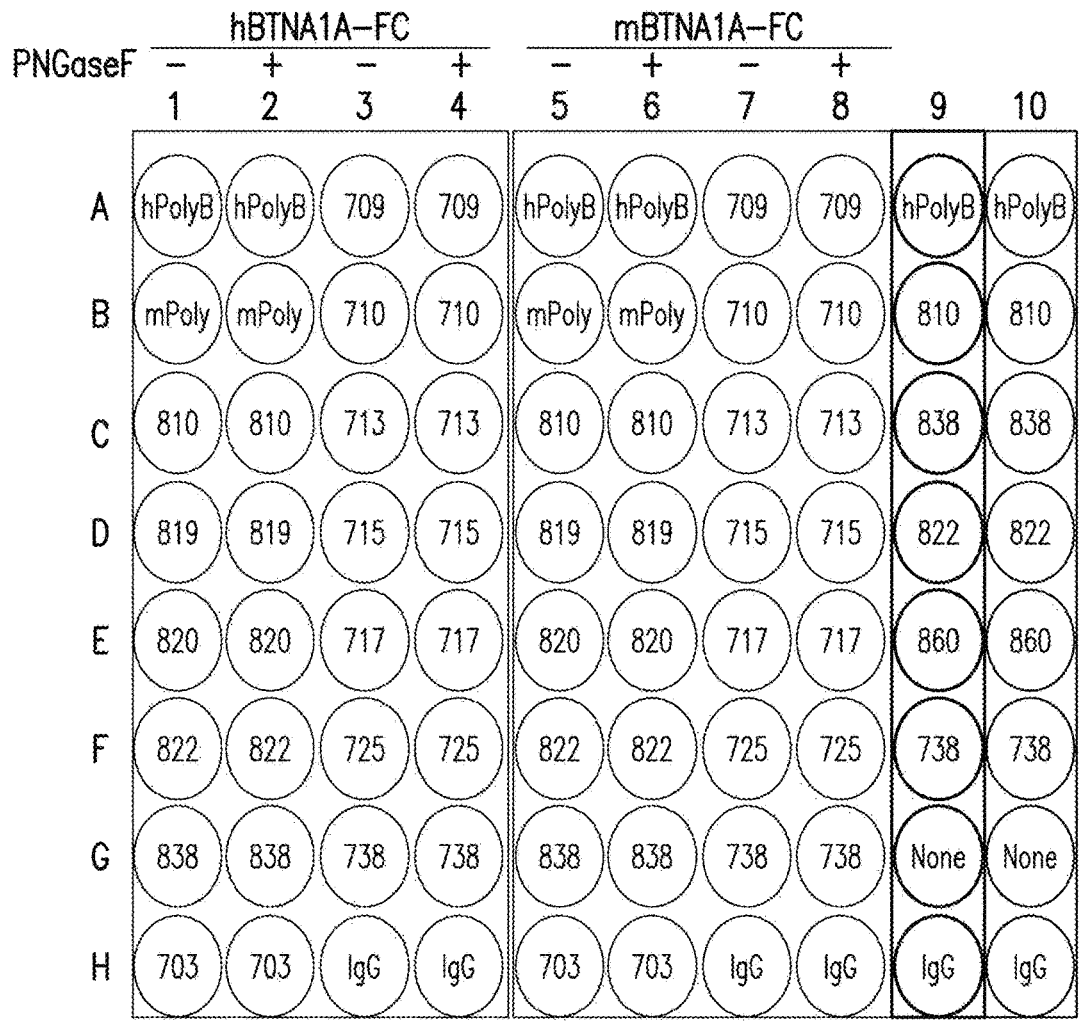

FIGS. 9A and 9B—Dot blot analysis of mouse anti-human BTN1A1 antibodies. In particular, FIG. 9A shows the result of the dot blot analysis, which was used to analyze glyco-specificity of mouse anti-human BTN1A1 monoclonal antibodies. Antigen BTN1A1-ECD tagged with 6×His was treated with PNGase F to remove N-glycosylation. Polyclonal antibodies were used for positive control. To test the species specificity of BTN1A1, human and mouse BTN1A1 tagged with human IgG1 Fc region was used (lane 1-4 with human BTN1A1-Fc and lane 5-8 with mouse BTN1A1-Fc). The term "ECD" stands for extracellular domain. FIG. 9B provides layout of the dot blot as shown in FIG. 9A.

Figure 10:
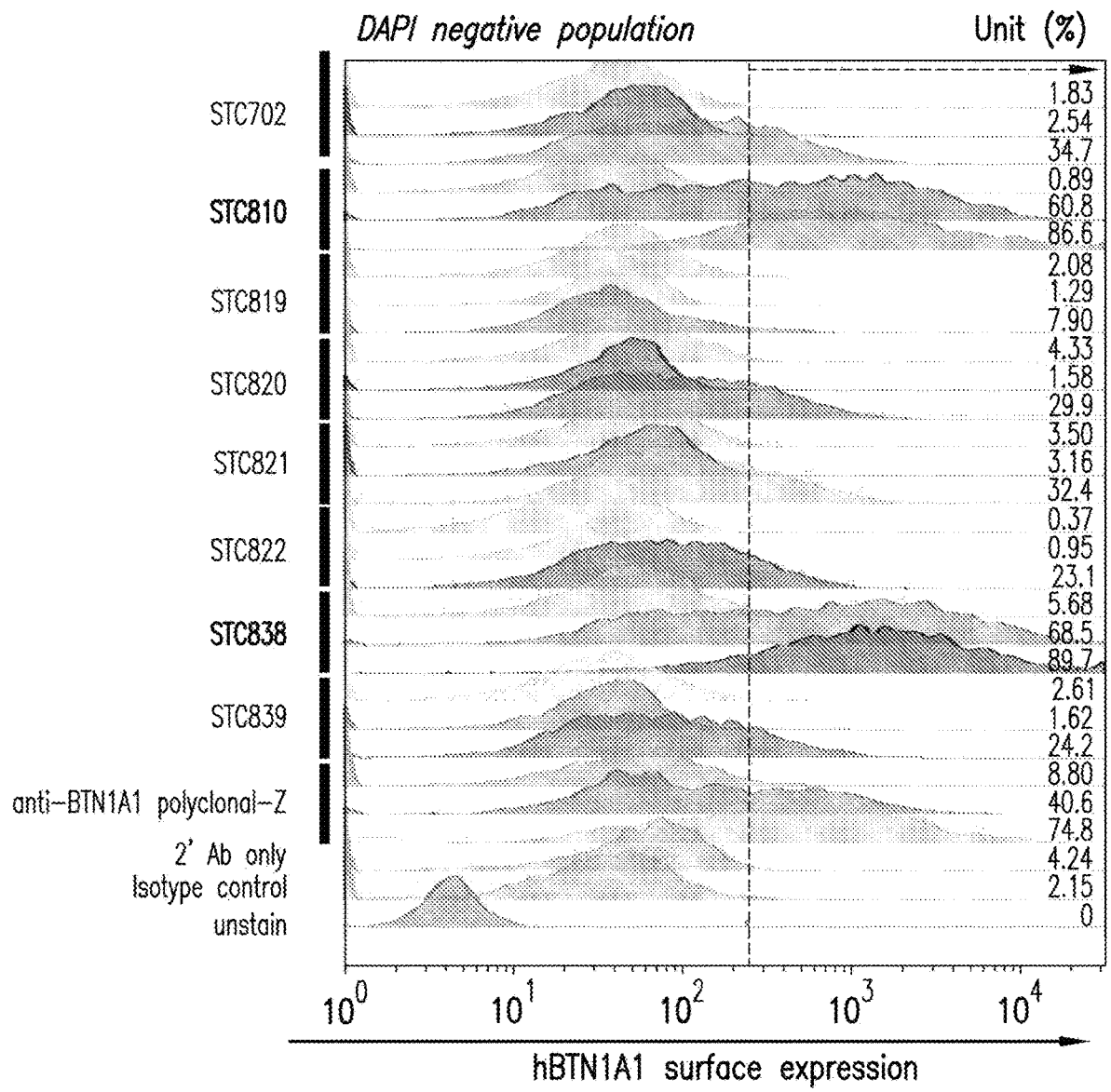

FIG. 10—FACS analysis of mouse anti-human BTN1A1 monoclonal antibodies. Human BTN1A1-2NQ (i.e. N55Q and N215Q) and human BTN1A1 WT were expressed in HEK293T cells by transient transfection. The surface expression of hBTN1A1 was measured by FACS analysis with anti-BTN1A1 monoclonal antibodies designated as STC702, STC810, STC819, STC820, STC821, STC822, STC838, and STC839. Anti-BTN1A1 polyclonal antibodies were used as a positive control.

Figure 11A:
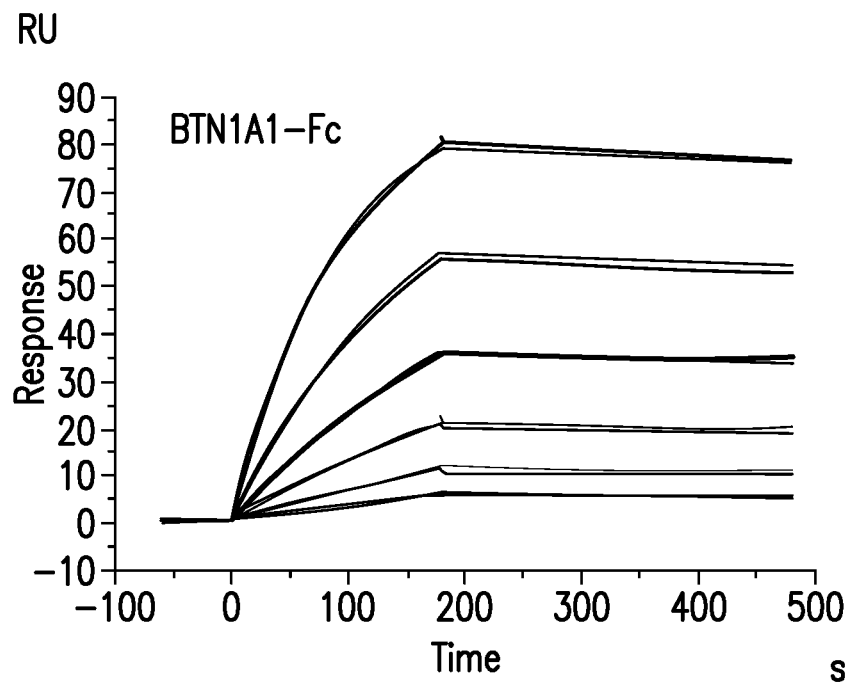
Figure 11B:
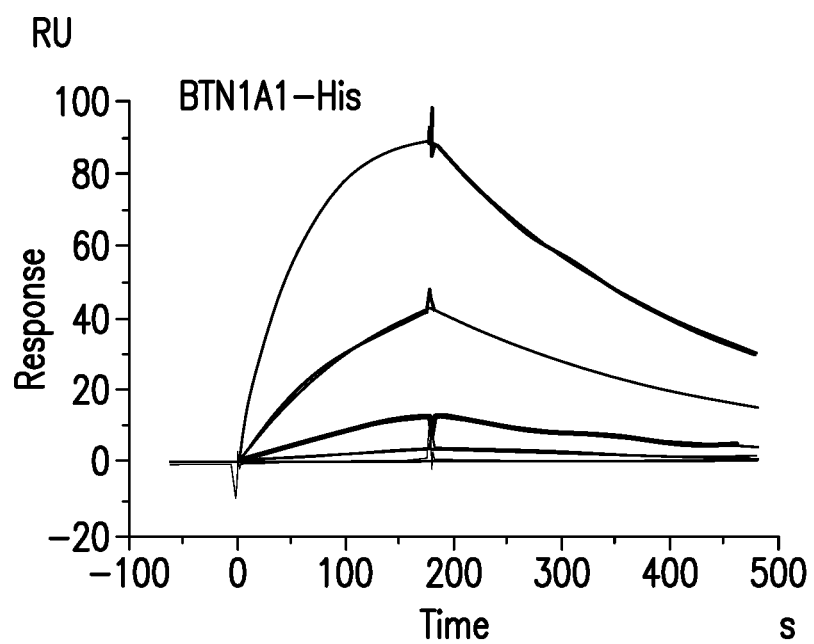

FIGS. 11A and 11B—Surface plasmon resonance analysis of BTN1A1-Fc and BTN1A1-His binding to immobilized STC810 MAb. In particular, FIG. 11A: Sensorgrams showing real-time binding of soluble BTN1A1-Fc protein (2-64 nM with 2-fold dilution) to STC810 immobilized on a Protein A-CM5 chip. Flow cells without any immobilized protein were used as the controls for non-specific binding and were subtracted from the presented data. FIG. 11B: Sensorgrams showing real-time binding of soluble BTN1A1-His protein (2-64 nM with 4-fold dilution) to STC810 immobilized on a Protein A-CM5 chip.

Figure 12:
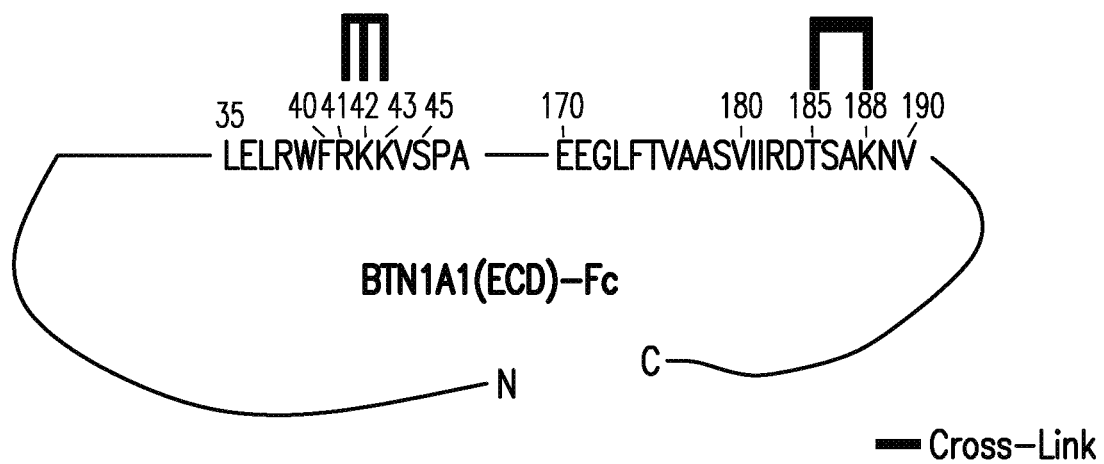

FIG. 12—Epitope mapping of BTN1A1-Fc. STC810 and BTN1A1 (ECD)-Fc were subject to Ag-Ab cross-linking and analyzed by high-mass MALDI. FIG. 12 shows the amino acid residues of BTN1A1 (ECD)-Fc that were cross-linked to STC810, including R41, K42, K43, T185 and K188. FIG. 12 shows a synthesized epitope of BTN1A1 (ECD)-Fc antigen for STC810: LELRWFRKKVSPA (SEQ ID NO:34)—EEGLFTVAASVIIRDTSAKNV (SEQ ID NO:35).

Figure 13:
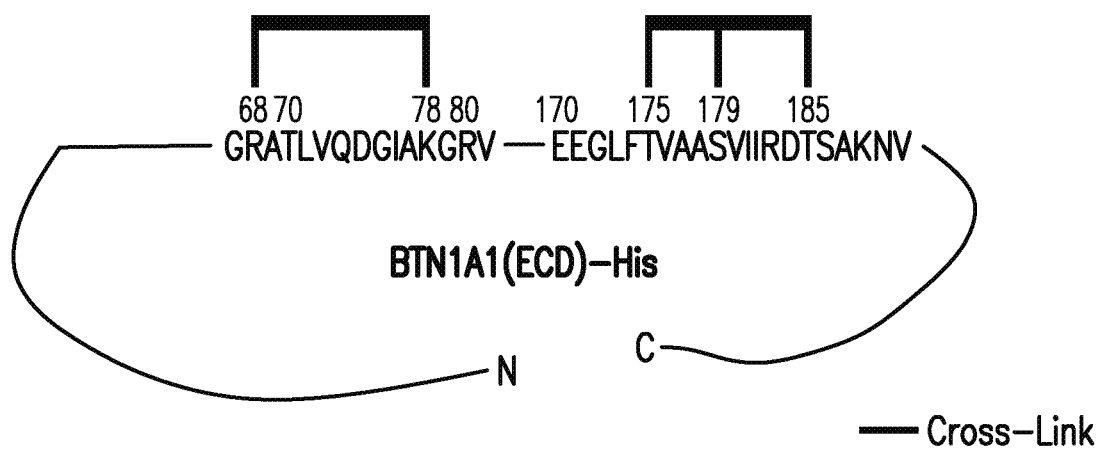

FIG. 13—Epitope mapping of BTN1A1-Fc. STC810 and BTN1A1 (ECD)-His were subject to Ag-Ab cross-linking and analyzed by high-mass MALDI. FIG. 13 shows the amino acid residues of BTN1A1 (ECD)-His that were cross-linked to STC810, including R68, K78, T175, S179 and T185. FIG. 13 shows a synthesized epitope of BTN1A1 (ECD)-His antigen for STC810: GRATLVQDGIAKGRV (SEQ ID NO:40)—EEGLFTVAASVIIRDTSAKNV (SEQ ID NO:41).

Figure 14:
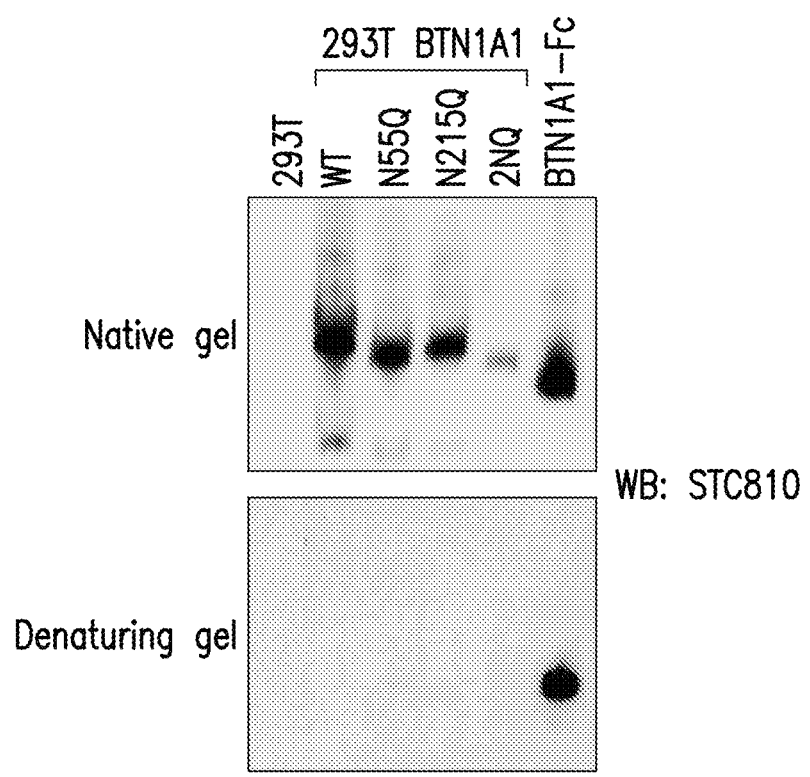

FIG. 14—Western Blot Analysis of BTN1A1 WT, N55Q, N215Q and 2NQ mutants in the native or denaturing conditions. (Top panel) HEK293T cells were transiently transfected with expression vectors for wild-type BTN1A1 and mutant BTN1A1, including N55Q, N215Q, and 2NQ (i.e. N55Q and N215Q). At 48 h after transfection, whole-cell lysates were prepared and proteins were separated in native SDS-PAGE. The gel was subjected to immunoblot analysis with antibody for STC810. (Bottom panel) Cell lysates prepared above were reduced by β-mercaptoethanol and denatured by boiling. The samples were separated in SDS-PAGE and was subjected to immunoblot analysis with antibody for STC810. BTN1A1-Fc was used as a positive control.

Figure 15:
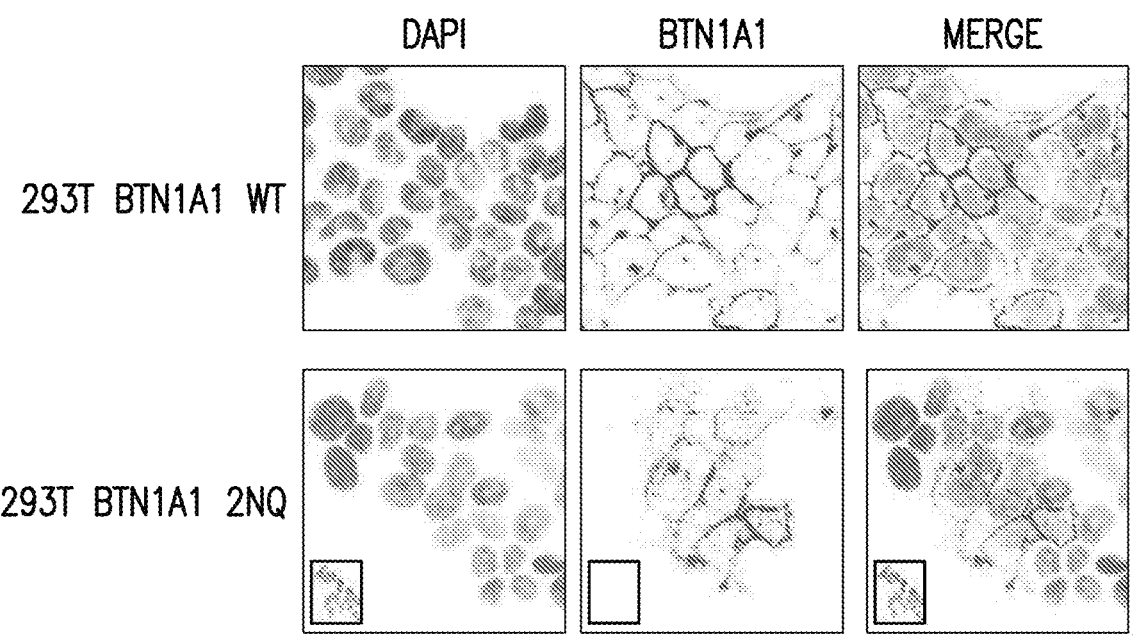

FIG. 15—Immunofluorescence Analysis of STC810 antibodies by Confocal Microscopy. HEK293T cells were transiently transfected with expression vectors for wild-type BTN1A1 (BTN1A1 WT) and mutant BTN1A1 (BTN1A1-2NQ (i.e. N55Q and N215Q)). Cells were plated on a cover slip and probed with primary antibody (STC810) against BTN1A1 and secondary antibodies against mouse IgG. Blue staining is DAPI, which stains the nucleus.

Figure 16A:
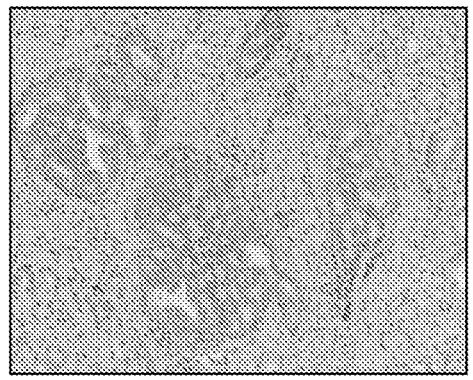
Figure 16B:
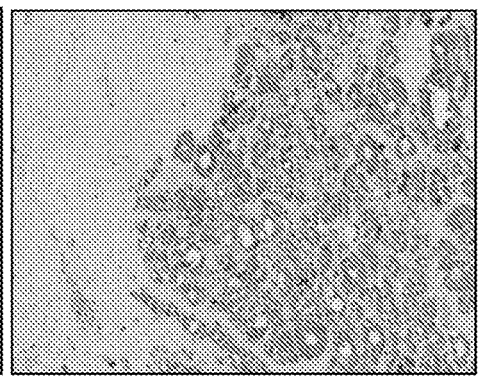
Figure 16C:
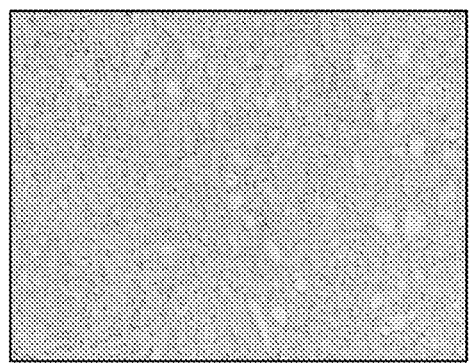
Figure 16D:
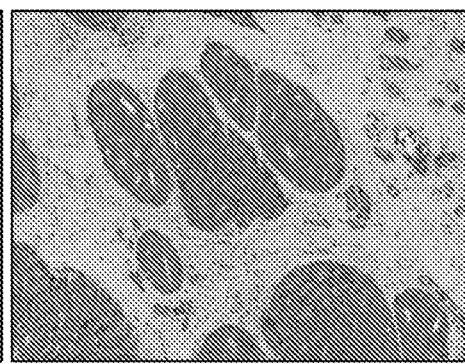

FIGS. 16A-16D—Immunohistochemistry of BTN1A1 expression in prostate tumor. Formalin-fixed paraffin-embedded sections of prostate tissues from cancer patient were subjected to immunostaining of BTN1A1 using mouse anti-human BTN1A1 antibodies, and visualized by 3,3'-diaminobenzidine (DAB) with hematoxylin counterstain (FIG. 16B, 3 μg/ml STC810; FIG. 16D, 5 μg/ml STC810). Mouse IgG was used as negative controls (FIG. 16A, 3 μg/ml mouse IgG; FIG. 16C, 5 μg/ml mouse IgG).

Figure 17:
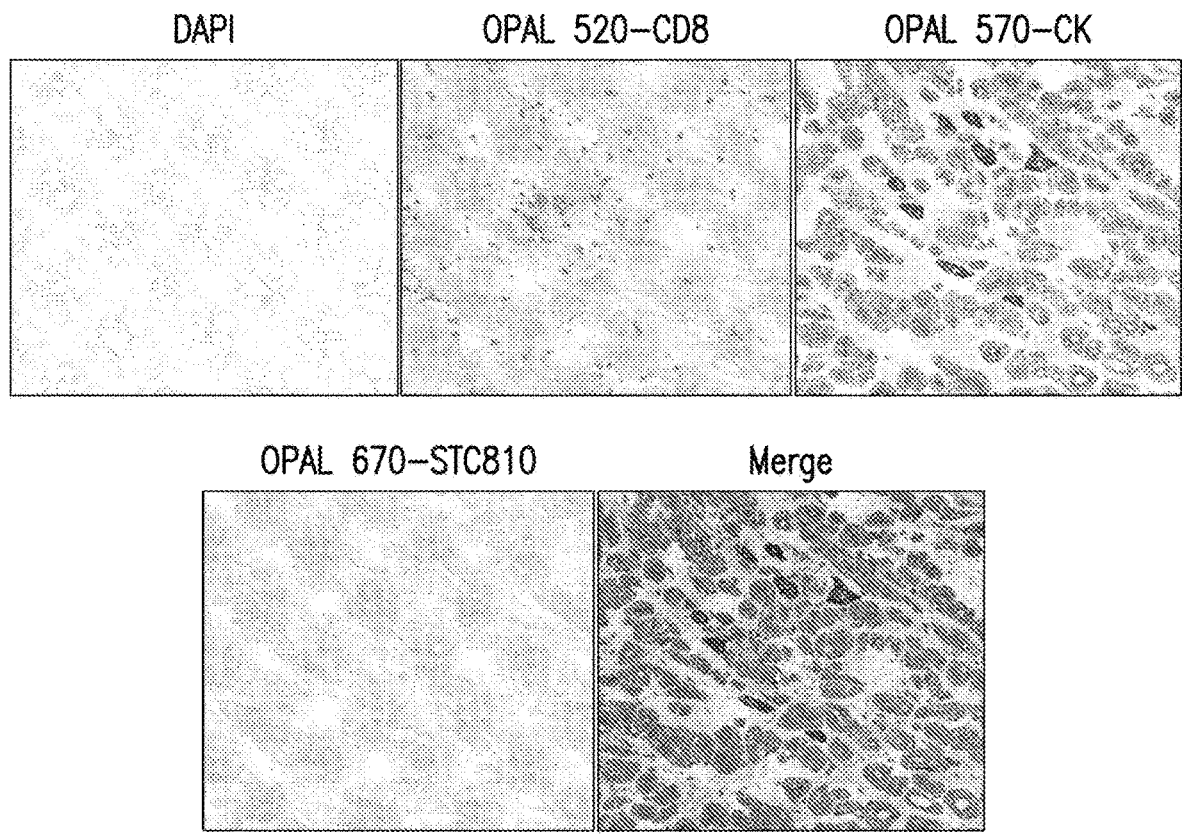

FIG. 17—BTN1A1 expression in prostate tumor samples by OPAL staining. Unmixed composite image from multispectral data separating DAPI, CD8, cytokeratin, and BTN1A1 (STC810) from each fluorescence. A multiplexed staining approach consists of serial application of tyramide signal amplification (TSA) amplified immunofluorescence labels for each antibody and a DAPI counterstain. Prior to immunofluorescence labeling, all four antigens are retrieved with a single microwave step. Each labeling cycle consists of application of a primary antibody, a secondary antibody conjugated to horse radish peroxidase (HRP), and TSA conjugated to a fluorophore. After each TSA-fluorophore conjugate is applied, the sample is processed with the microwave again to strip primary and secondary antibodies, leaving TSA-fluorophore constructs which are covalently bound and very resilient to microwave exposure. Samples were imaged using the Vectra® multispectral slide analysis system from PerkinElmer to automatically acquire 25 fields of interest per slide. Merged image is shown in bottom right panel.

Figure 18A:
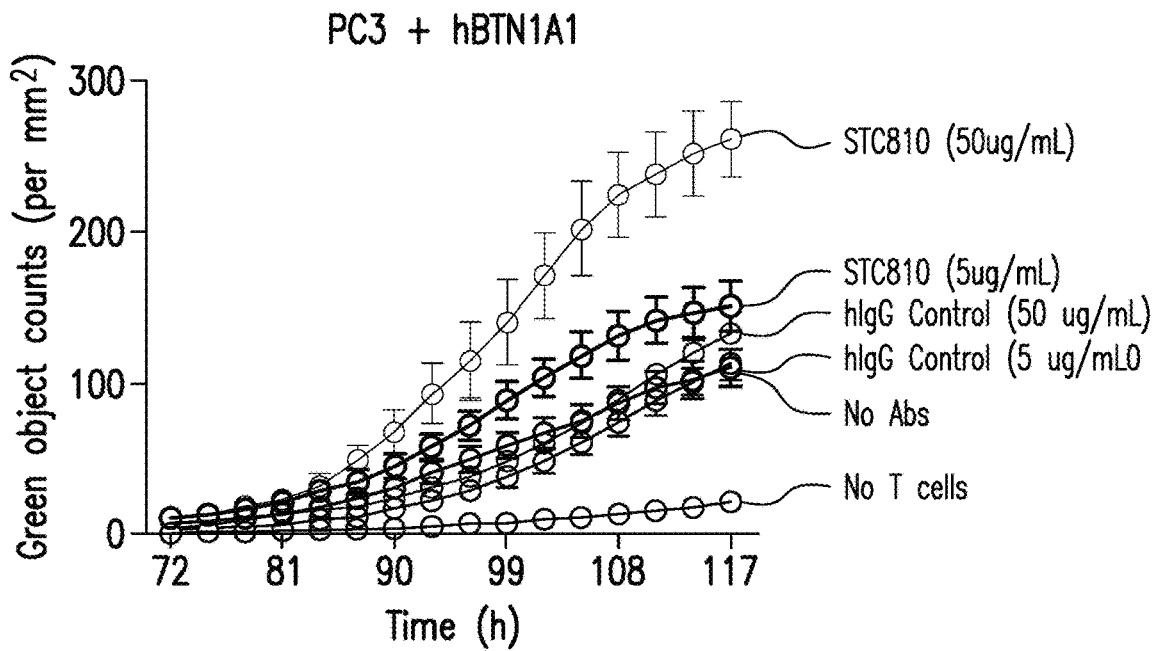
Figure 18B:
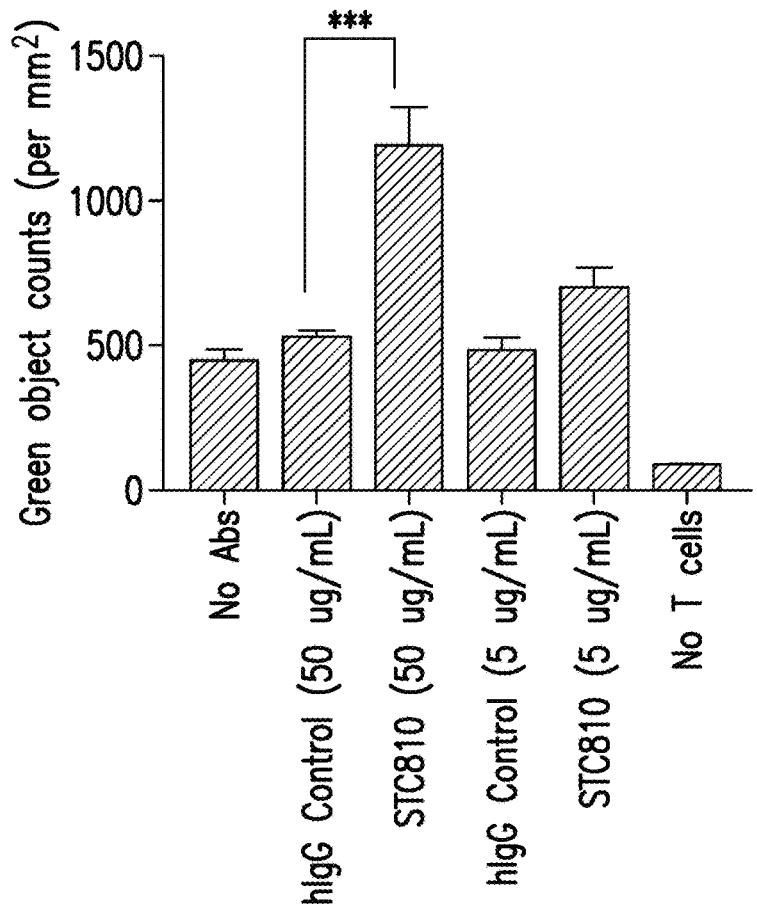
Figure 18C:
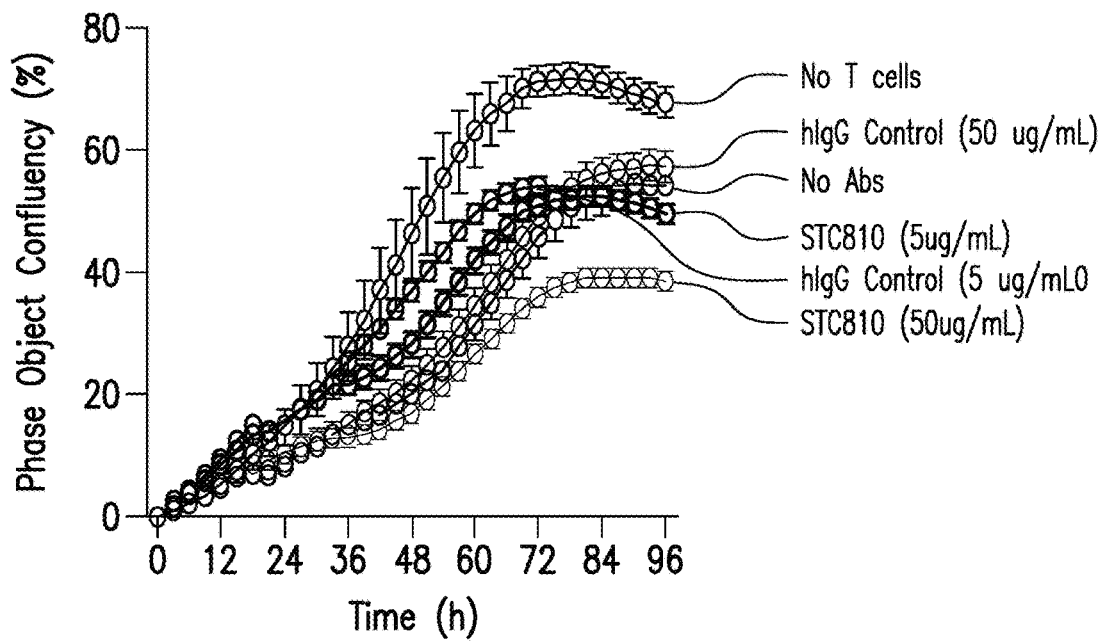
Figure 18D:
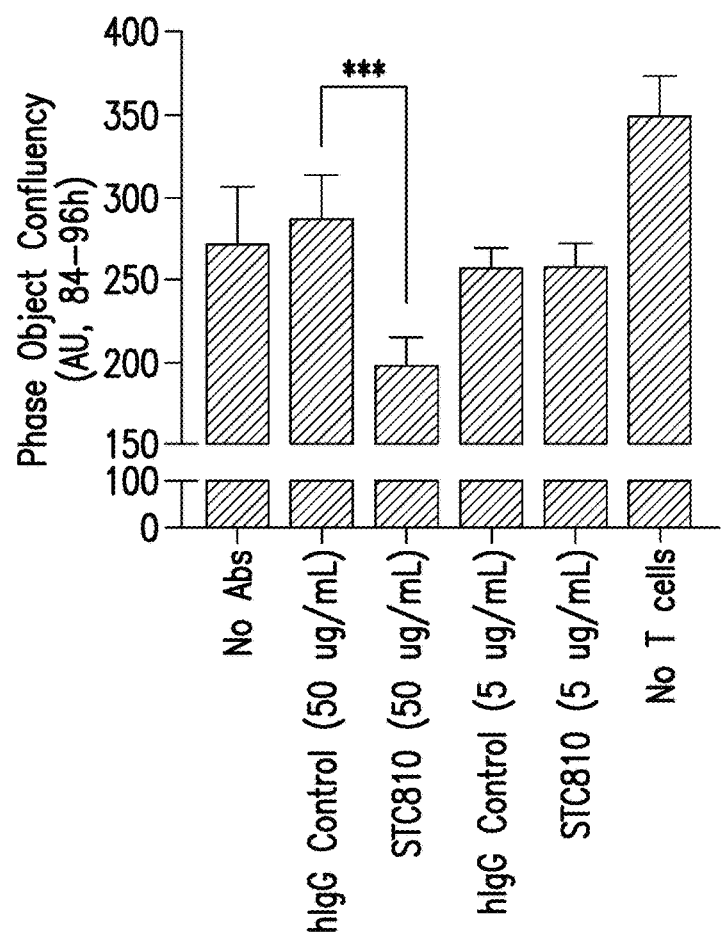

FIGS. 18A-18D—STC810 resulted in apoptosis in hBTN1A1 overexpressing PC3 cells treated with total T cells. T cells were activated with anti-CD3 antibody (100 ng/ml) and IL-2 (10 ng/ml) in the presence of antibody. Cancer cell: T cell ratio of 1:10 was used in this study. Apoptosis of PC3 cells (prostate cancer cells) caused by antibody (STC810) treatment was monitored by using a real-time imaging system IncuCyte ZOOM (Essen Bioscience) and green caspase 3/7 fluorescent substrate (10 μM, Essen Bioscience). In particular, FIG. 18A shows apoptotic cells that were stained with green caspase 3/7 fluorescent PC3 cells. FIG. 18B shows the calculation of relative apoptosis of PC3 cells at 120 h post treatment with antibody. FIG. 18C shows proliferation of cancer cell as monitored by confluency of PC3 cells on the plate. FIG. 18D shows the calculation of relative proliferation of PC3 cells at 120 h post treatment with antibody.

FIG. 19—Duolink Assay. Duolink assay generally includes the following six steps to detect single protein-protein interaction: 1. Incubate with a target primary antibodies; 2. Add PLA probes "PLUS" and "MINUS"; 3. hybridize connector oligos; 4. Ligation to form a complete DNA circle; 5. Rolling circle amplification; and 6. Add fluorescent probes to reveal interaction.

Figure 20A:
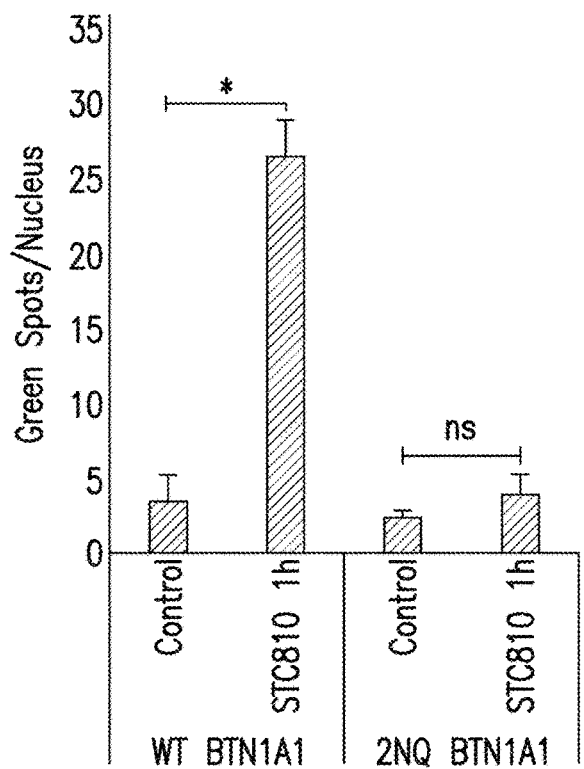
Figure 20B:
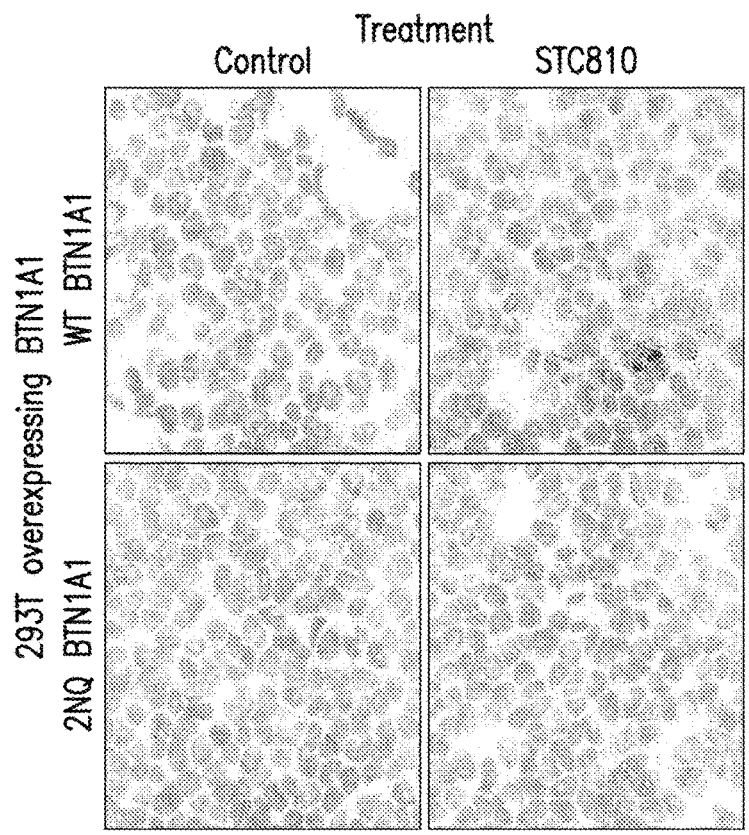

FIGS. 20A-20B—Lysosome internalization of BTN1A1 by STC810. 293T cells overexpressing BTN1A1 WT or BTN1A1 2NQ cultured on Poly-L-Lysine coverslips were treated with 10 pg/mL STC810 or untreated for 1 h, then costained with STC810 5 ug/mL and anti-LAMP1 1 ug/mL using DuoLink reagents to generate green fluorescence indicative of colocalization of BTN1A1 with the lysosomal marker (FIG. 20B). Green spots and nuclei were quantitated and the ratios represented in chart (FIG. 20A). Error bars indicate SEM. *P=0.04

Figure 21:
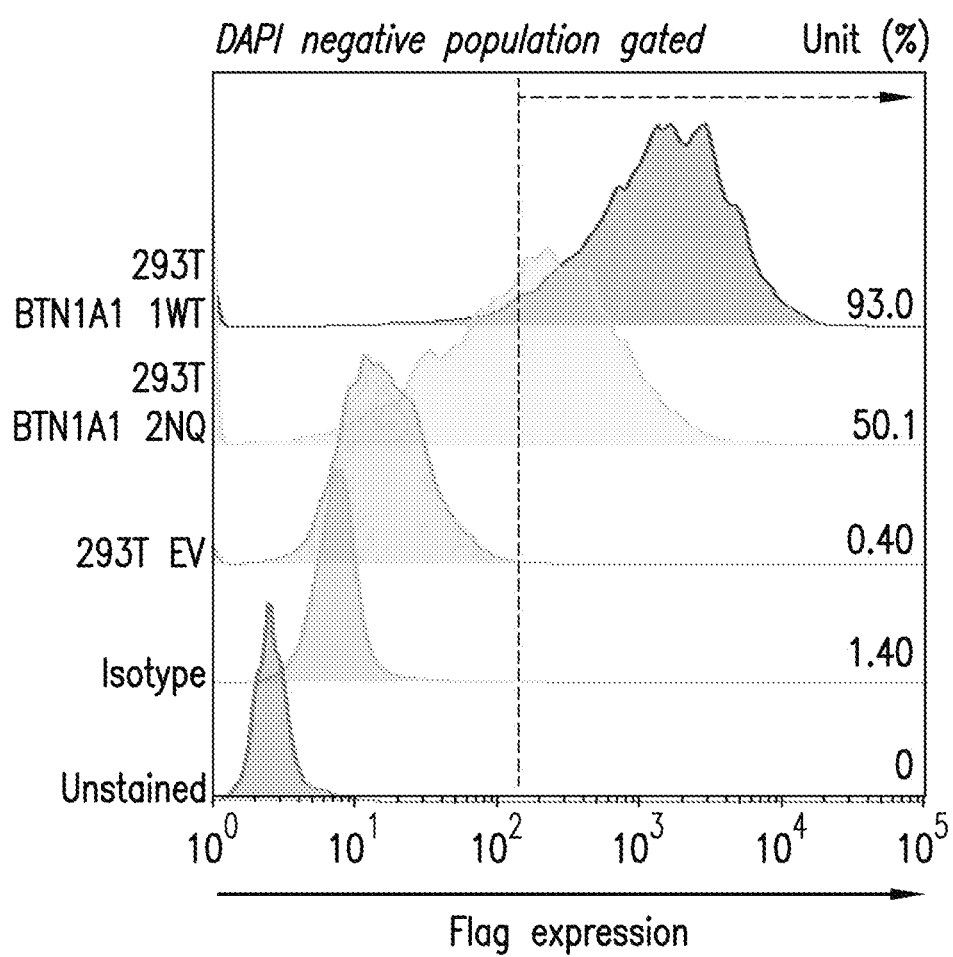

FIG. 21—Detection of BTN1A1 WT and BTN1A1 2NQ Expression by FACS. FACS analysis of HEK293T cells overexpressing BTN1A1 WT, BTN1A1 2NQ, or empty vector (EV). The flag expression indicates the expression of BTN1A1 (WT or 2NQ; flag tagged) in the HEK293T cells.

5. DETAILED DESCRIPTIONS

The B7 family of co-stimulatory molecules can drive the activation and inhibition of immune cells. A related family of molecules—the buryrophilins—also have immunomodulatory functions similar to B7 family members. Butyrophilin, subfamily 1, member A1 ("BTN1A1") is a type I membrane glycoprotein and a major component of milk fat globule membrane, and has structural similarities to the B7 family. BTN1A1 is known as a major protein regulating the formation of fat droplets in the milk. (Ogg et al. *PNAS*, 101(27):10084-10089 (2004)). BTN1A1 is expressed in immune cells, including T cells. Treatment with recombinant BTN1A1 was found to inhibit T cell activation and protect animal models of EAE. (Stefferl et al., *J. Immunol.* 165(5):2859-65 (2000)).

BTN1A1 is also specifically and highly expressed in cancer cells. The BTN1A1 in cancer cells are also glycosylated. The expression of BTN1A1 can be used to aid cancer diagnosis as well as to evaluate the efficacy of a cancer treatment.

Provided herein are anti-BTN1A1 antibodies and other molecules that can immunospecifically bind to BTN1A1, and methods for use thereof in providing cancer diagnosis, evaluating of a cancer treatment, or modulating the activity of immune cells and in treating cancers.

5.1. Definitions

As used herein, and unless otherwise specified, the articles "a," "an," and "the" refer to one or to more than one of the grammatical object of the article. By way of example, an antibody refers to one antibody or more than one antibodies.

As used herein, and unless otherwise specified, the term "Butyrophilin, subfamily 1, member A1" or "BTN1A1" refers to BTN1A1 from any vertebrate source, including mammals such as primates (e.g., humans, cynomolgus monkey (cyno)), dogs, and rodents (e.g., mice and rats). Unless otherwise specified, BTN1A1 also includes various BTN1A1 isoforms, related BTN1A1 polypeptides, including SNP variants thereof, as well as different modified forms of BTN1A1, including but not limited to phosphorylated BTN1A1, glycosylated BTN1A1, and ubiquitinated BTN1A1. As used herein, glycosylated BTN1A1 include BTN1A1 with N55, N215, and/or N449 glycosylation.

An exemplary amino acid sequence of human BTN1A1 (BC096314.1 GI: 64654887), is provided below with the potential glycosylation sites bolded and underlined:

(SEQ ID NO: 1)
MAVFPSSGLPRCLLTLILLQLPKLDSAPFDVIGPPEPILAVVGEDAKLPC

RLSPNASAEHLELRWFRKKVSPAVLVHRDGREQEAEQMPEYRGRATLVQD

GIAKGRVALRIRGVRVSDDGEYTCFFREDGSYEEALVHLKVAALGSDPHI

SMQVQENGEICLECTSVGWYPEPQVQWRTSKGEKFPSTSESRNPDEEGLF

TVAASVIIRDTSAKNVSCYIQNLLLGQEKKVEISIPASSLPRLTPWIVAV

AVILMVLGLLTIGSIFFTWRLYNERPRERRNEFSSKERLLEELKWKKATL

HAVDVTLDPDTAHPHLFLYEDSKSVRLEDSRQKLPEKTERFDSWPCVLGR

ETFTSGRHYWEVEVGDRTDWAIGVCRENVMKKGFDPMTPENGFWAVELYG

NGYWALTPLRTPLPLAGPPRRVGIFLDYESGDISFYNMNDGSDIYTFSNV

TFSGPLRPFFCLWSSGKKPLTICPIADGPERVTVIANAQDLSKEIPLSPM

GEDSAPRDADTLHSKLIPTQPSQGAP

An exemplary encoding nucleic acid sequence of human BTN1A1 (BC096314.1 GI: 64654887), is provided below:

(SEQ ID NO: 2)
ATGGCAGTTTTCCCAAGCTCCGGTCTCCCCAGATGTCTGCTCACCCTCAT

TCTCCTCCAGCTGCCCAAACTGGATTCAGCTCCCTTTGACGTGATTGGAC

CCCCGGAGCCCATCCTGGCCGTTGTGGGTGAGGACGCCAAGCTGCCCTGT

CGCCTGTCTCCGAACGCGAGCGCCGAGCACTTGGAGCTACGCTGGTTCCG

AAAGAAGGTTTCGCCGGCCGTGCTGGTGCATAGGGACGGGCGCGAGCAGG

AAGCCGAGCAGATGCCCGAGTACCGCGGGCGGGCGACGCTGGTCCAGGAC

GGCATCGCCAAGGGGCGCGTGGCCTTGAGGATCCGTGGCGTCAGAGTCTC

TGACGACGGGGAGTACACGTGCTTTTTCAGGGAGGATGGAAGCTACGAAG

AAGCCCTGGTGCATCTGAAGGTGGCTGCTCTGGGCTCTGACCCTCACATC

AGTATGCAAGTTCAAGAGAATGGAGAAATCTGTCTGGAGTGCACCTCAGT

GGGATGGTACCCAGAGCCCCAGGTGCAGTGGAGAACTTCCAAGGGAGAGA

AGTTTCCATCTACATCAGAGTCCAGGAATCCTGATGAAGAAGGTTTGTTC

ACTGTGGCTGCTTCAGTGATCATCAGAGACACTTCTGCGAAAAATGTGTC

CTGCTACATCCAGAATCTCCTTCTTGGCCAGGAGAAGAAAGTAGAAATAT

CCATACCAGCTTCCTCCCTCCCAAGGCTGACTCCCTGGATAGTGGCTGTG

GCTGTCATCCTGATGGTTCTAGGACTTCTCACCATTGGGTCCATATTTTT

CACTTGGAGACTATACAACGAAAGACCCAGAGAGAGGAGGAATGAATTCA

GCTCTAAAGAGAGACTCCTGGAAGAACTCAAATGGAAAAGGCTACCTTG

CATGCAGTTGATGTGACTCTGGACCCAGACACAGCTCATCCCCACCTCTT

TCTTTATGAGGATTCAAAATCTGTTCGACTGGAAGATTCACGTCAGAAAC

TGCCTGAGAAAACAGAGAGATTTGACTCCTGGCCCTGTGTGTTGGGCCGT

GAGACCTTCACCTCAGGAAGGCATTACTGGGAGGTGGAGGTGGGAGACAG

GACTGACTGGGCAATCGGCGTGTGTAGGGAGAATGTGATGAAGAAAGGAT

TTGACCCCATGACTCCTGAGAATGGGTTCTGGGCTGTAGAGTTGTATGGA

AATGGGTACTGGGCCCTCACTCCTCTCCGGACCCCTCTCCCATTGGCAGG

GCCCCCACGCCGGGTTGGGATTTTCCTAGACTATGAATCAGGAGACATCT

CCTTCTACAACATGAATGATGGATCTGATATCTATACTTTCTCCAATGTC

ACTTTCTCTGGCCCCCTCCGGCCCTTCTTTTGCCTATGGTCTAGCGGTAA

AAAGCCCCTGACCATCTGCCCAATTGCTGATGGGCCTGAGAGGGTCACAG

TCATTGCTAATGCCCAGGACCTTTCTAAGGAGATCCCATTGTCCCCCATG

GGGGAGGACTCTGCCCCTAGGGATGCAGACACTCTCCATTCTAAGCTAAT

CCCTACCCAACCCAGCCAAGGGGCACCTTAA

As used herein, and unless otherwise specified, the term "antibody" refers to a polypeptide product of B cells within the immunoglobulin (or "Ig") class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press.; Kuby (1997) *Immunology*, Third Edition, W.H. Freeman and Company, New York). Here, the specific molecular antigen includes the target BTN1A1, which can be a BTN1A1 polypeptide, BTN1A1 fragment or BTN1A1 epitope. Antibodies provided herein include, but are not limited to, monoclonal antibodies, synthetic antibodies, recombinantly produced antibodies, bi-specific antibodies, multispecific antibodies, human antibodies, humanized antibodies, camelized antibodies, chimeric antibodies, intrabodies, anti-idiotypic (anti-Id) antibodies.

As used herein, and unless otherwise specified, the term "monoclonal antibody" refers to an antibody that is the product of a single cell clone or hybridoma or a population of cells derived from a single cell. A monoclonal antibody also is intended to refer to an antibody produced by recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. In contrast, polyclonal antibodies are obtained from different B cells within a population, which are a combination of immunoglobulin molecules that bind a specific antigen. Each immunoglobulin of the polyclonal antibodies can bind a different epitope of the same antigen. Methods for producing both monoclonal antibodies and polyclonal antibodies are well known in the art (Harlow and Lane., *Antibodies: A Laboratory Manual*, Cold Spring Harbor Laboratory Press (1989) and Borrebaeck (ed.), *Antibody Engineering: A Practical Guide*, W.H. Freeman and Co., Publishers, New York, pp. 103-120 (1991)).

As used herein, and unless otherwise specified, the term "human antibody" refers to an antibody that has a human variable region and/or a human constant region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. Here, a human antibody can include an antibody that binds to BTN1A1 and is encoded by a nucleic acid sequence that is a naturally occurring somatic variant of the human germline immunoglobulin nucleic acid sequence.

As used herein, and unless otherwise specified, the term "chimeric antibody" refers to an antibody that a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA,* 81:6851-6855 (1984)).

As used herein, and unless otherwise specified, the term "humanized antibody" refers to chimeric antibodies that include human immunoglobulins (e.g., recipient antibody) in which the native Complementarity Determining Region ("CDR") residues are replaced by residues from the corresponding CDR of a nonhuman species (e.g., donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can have residues that are not found in the recipient antibody or in the donor antibody. These modifications are made to further refine antibody performance. A humanized antibody heavy or light chain can have substantially all of at least one or more variable regions, in which all or substantially all of the CDRs correspond to those of a nonhuman immunoglobulin and all or substantially all of the FRs are those of a human immunoglobulin sequence. The humanized antibody can have at least a portion of an immunoglobulin constant region (Fc), typically that of a human immunoglobulin. For further details, see, Jones et al., *Nature,* 321:522-525 (1986); Riechmann et al., *Nature,* 332:323-329 (1988); and Presta, *Curr. Op. Struct. Biol.,* 2:593-596 (1992); Carter et al., *Proc. Natl. Acd. Sci. USA* 89:4285-4289 (1992); and U.S. Pat. Nos. 6,800,738, 6,719,971, 6,639,055, 6,407,213, and 6,054,297.

As used herein, and unless otherwise specified, the term "recombinant antibody" refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor, L. D. et al., *Nucl. Acids Res.* 20:6287-6295(1992)) or antibodies prepared, expressed, created or isolated by any other means that involves splicing of immunoglobulin gene sequences to other DNA sequences. Such recombinant antibodies can have variable and constant regions, including those derived from human germline immunoglobulin sequences (see Kabat, E. A. et al. (1991) *Sequences of Proteins of Immunological Interest*, Fifth Edition, U.S. Department of Health and Human Services, NIH Publication No. 91-3242). The recombinant antibodies can also be subjected to in vitro mutagenesis (or, when an animal transgenic for human Ig sequences is used, in vivo somatic mutagenesis) and thus the amino acid sequences of the VH and VL regions of the recombinant antibodies can be sequences that, while derived from and related to human germline VH and VL sequences, do not naturally exist within the human antibody germline repertoire in vivo.

As used herein, and unless otherwise specified, a "neutralizing antibody" refers to an antibody that blocks the binding the BTN1A1 with its natural ligands and inhibits the signaling pathways mediated by BTN1A1 and/or its other physiological activities. The IC50 of a neutralizing antibody refers to the concentration of the antibody that is required to neutralize 50% of BTN1A1 in a neutralization assay. The IC50 of the neutralizing antibody can range between 0.01-10 µg/ml in the neutralization assay.

As used herein, and unless otherwise specified, the term "antigen binding fragment" and similar terms refer to a portion of an antibody which includes the amino acid residues that immunospecifically bind to an antigen and confer on the antibody its specificity and affinity for the antigen. An antigen binding fragment can be referred to as a functional fragment of an antibody. An antigen binding fragment can be monovalent, bivalent, or multivalent.

Molecules having an antigen binding fragment include, for example, an Fd, Fv, Fab, F(ab'), $F(ab)_2$, $F(ab')_2$, single chain Fv (scFv), diabody, triabody, tetrabody, minibody, or a single domain antibody. A scFv can be monovalent scFv or bivalent scFv. Other molecules having an antigen binding fragment can include, for example, heavy or light chain polypeptides, variable region polypeptides or CDR polypeptides or portions thereof so long as such antigen binding fragments retain binding activity. Such antigen binding fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics,* 22:189-224 (1993); Plückthun and Skerra, *Meth. Enzymol.,* 178:497-515 (1989) and in Day, E. D., *Advanced Immunochemistry*, Second Ed., Wiley-Liss, Inc., New York, NY (1990). An antigen binding fragment can be a polypeptide having an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The heavy chain of an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha (α), delta (δ), epsilon (ε), gamma (γ) and mu (µ), based on the amino acid sequence of the heavy chain constant region. The distinct heavy chains differ in size: α, δ and γ contain approximately 450 amino acids, while μ and ϲ contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The light chain of an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

The variable domain or variable region of an antibody refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) 5$^{th}$ ed. A variable region can be a human variable region.

A CDR refers to one of three hypervariable regions (H1, H2 or H3) within the non-framework region of the immunoglobulin (Ig or antibody) VH (3-sheet framework, or one of three hypervariable regions (L1, L2 or L3) within the non-framework region of the antibody VL (3-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved (3-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to standard designations are set forth in the Table 1 below.

TABLE 1

CDR Definitions

| | Exemplary (Kabat + Chothia) | IMGT | Kabat | AbM | Chothia | Contact |
|---|---|---|---|---|---|---|
| V$_H$ CDR1 | 26-35 | 27-38 | 31-35 | 26-35 | 26-32 | 30-35 |
| V$_H$ CDR2 | 50-65 | 56-65 | 50-65 | 50-58 | 53-55 | 47-58 |
| V$_H$ CDR3 | 95-102 | 105-117 | 95-102 | 95-102 | 96-101 | 93-101 |
| V$_L$ CDR1 | 24-34 | 27-38 | 24-34 | 24-34 | 26-32 | 30-36 |
| V$_L$ CDR2 | 50-56 | 56-65 | 50-56 | 50-56 | 50-52 | 46-55 |
| V$_L$ CDR3 | 89-97 | 105-117 | 89-97 | 89-97 | 91-96 | 89-96 |

One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest.

The "framework" or "FR" residues refer to those variable domain residues flanking the CDRs. FR residues are present, e.g., in chimeric, humanized, human, domain antibodies, diabodies, linear antibodies, and bispecific antibodies. FR residues are those variable domain residues other than the hypervariable region residues herein defined.

As used herein, and unless otherwise specified, the term "isolated" as used in reference to an antibody means the antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). In certain embodiments, when the antibody is recombinantly produced, it is substantially free of culture medium, e.g., culture medium represents less than about 20%, 10%, or 5% of the volume of the protein preparation. In certain embodiments, when the antibody is produced by chemical synthesis, it is substantially free of chemical precursors or other chemicals, e.g., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al. J. Bio. Chem. 193: 265-275, 1951), such as 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step. In a specific embodiment, antibodies provided herein are isolated As used herein, and unless otherwise specified, the term "polynucleotide," "nucleotide," nucleic acid" "nucleic acid molecule" and other similar terms are used interchangeable and include DNA, RNA, mRNA and the like.

As used herein, and unless otherwise specified, the term "isolated" as used in reference to a nucleic acid molecule means the nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding an antibody provided herein is isolated or purified.

As used herein and unless otherwise specified, the term "bind" or "binding" refers to an interaction between molecules. Interactions can be, for example, non-covalent interactions including hydrogen bonds, ionic bonds, hydrophobic interactions, and/or van der Waals interactions. The strength of the total non-covalent interactions between an antibody and a single epitope of a target molecule, such as BTN1A1, is the affinity of the antibody for that epitope. "Binding affinity" generally refers to the strength of the sum total of noncovalent interactions between a single binding site of a molecule (e.g., a binding protein such as an antibody) and its binding partner (e.g., an antigen).

The affinity of a binding molecule X, such as an antibody, for its binding partner Y, such as the antibody's cognate antigen can generally be represented by the dissociation constant ($K_D$). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. The "$K_D$" or "$K_D$ value" can be measured by assays known in the art, for example by a binding assay. The $K_D$ can be measured in a radiolabeled antigen binding assay (MA), for example, performed with the Fab version of an antibody of interest and its antigen (Chen, et al., (1999) *J. Mol. Biol.* 293:865-881). The $K_D$ or $K_D$ value can also be measured by using surface plasmon resonance assays by Biacore, using, for example, a BIAcore™-2000 or a BIAcore™-3000 BIAcore, Inc., Piscataway, NJ), or by biolayer interferometry using, for example, the OctetQK384 system (ForteBio, Menlo Park, CA).

As used herein, and unless otherwise specified, a molecule is said to be able to "immunospecifically bind" a second molecule if such binding exhibits the specificity and affinity of an antibody to its cognate antigen. An antibody immunospecifically binds to a target region or conformation ("epitope") of an antigen if such binding involves the antigen recognition site of the antibody. An antibody that immunospecifically binds to a particular antigen can bind to other antigens with lower affinity if the other antigen has some sequence or conformational similarity that is recognized by the antigen recognition site as determined by, e.g., immunoassays, BIACORE® assays, or other assays known in the art. An antibody in general do not bind to a totally unrelated antigen. Some antibodies (and their antigen binding fragments) does not cross-react with other antigens. Antibodies can also bind to other molecules in a way that is not immunospecific, such as to FcR receptors, by virtue of binding domains in other regions/domains of the antibody that do not involve the antigen recognition site, such as the Fc region.

An antibody or antigen binding fragment that immunospecifically binds to an antigen or an epitope of an antigen that includes a glycosylation site can bind to the antigen or the epitope in both glycosylated form or unglycosylated form. In some embodiments, the antibody or antigen binding fragment preferentially binds to the glycosylated antigen or epitope over the unglycosylated antigen or epitope. The preferential binding can be determined by binding affinity. For example, an antibody or antigen binding fragment that preferentially binds to glycosylated BTN1A1 over unglycosylated BTN1A1 can bind to glycosylated BTN1A1 with a Kd less than the Kd exhibited relative to unglycosylated BTN1A1. In some embodiments, the antibody or antigen binding fragment binds to glycosylated BTN1A1 with Kd less than half of the Kd exhibited relative to unglycosylated BTN1A1. In some embodiments, the antibody or antigen binding fragment binds to glycosylated BTN1A1 with Kd at least 10 times less than the Kd exhibited relative to unglycosylated BTN1A1. In some embodiments, the antibody or antigen binding fragment binds to glycosylated BTN1A1 with Kd that is about 75%, about 50%, about 25%, about 10%, about 5%, about 2.5%, or about 1% of the Kd exhibited relative to unglycosylated BTN1A1.

The preferential binding can also be determined by binding assays and be indicated by, for example, fluorescence intensity ("MFI"). For example, an antibody or antigen binding fragment that preferentially binds to the glycosylated BTN1A1 can bind to glycosylated BTN1A1 with an MFI that is higher than the MFI as exhibited relative to unglycosylated BTN1A1. In some embodiments, the antibody or antigen binding fragment binds to glycosylated BTN1A1 with an MFI that is at least twice as high as the MFI as exhibited relative to unglycosylated BTN1A1. In some embodiments, antibody or the antigen binding fragment binds to glycosylated BTN1A1 with an MFI that is at least three times as high as the MFI as exhibited relative to unglycosylated BTN1A1. In some embodiments, antibody or the antigen binding fragment binds to glycosylated BTN1A1 with an MFI that is at least five times, at least ten times, at least fifteen times, or at least twenty times as high as the MFI as exhibited relative to unglycosylated BTN1A1.

As used herein, and unless otherwise specified, a molecule is said to "immunospecifically mask" glycosylation of an antigen or epitope, or a specified glycosylation site thereof, refers to its ability to either (1) block the glycosylation site of an unglycosylated antigen or epitope so that the antigen or epitope cannot be glycosylated, or (2) bind to the glycosylated antigen or epitope or at the specified glycosylation site of the glycosylated antigen or epitope and prevent the physiological effect of the glycosylation, such as the downstream signaling mediated by the glycosylation. For example, an antibody or antigen binding fragment that immunospecifically masks BTN1A1 glycosylation refers to the antibody or antigen binding fragment that (1) either blocks the glycosylation site of an unglycosylated BTN1A1 and prevents its glycosylation or (2) binds to glycosylated BTN1A1 and prevents the physiological effects of the glycosylation, such as the immunosuppressive effect mediated by the glycosylation. For another example, an antibody or antigen binding fragment that immunospecifically masks BTN1A1 glycosylation at N55 and N215 refers to the antibody or antigen binding fragment that either (1) blocks N55 and N215 of an unglycosylated BTN1A1 and prevents the glycosylation of N55 and N215 or (2) binds to BTN1A1 glycosylated at N55 and N215 and prevent the physiological effect of the glycosylation, such as the immunosuppressive effect mediated by the glycosylation.

As used herein, and unless otherwise specified, the term "carrier" refers to a diluent, adjuvant (e.g., Freund's adjuvant (complete or incomplete)), excipient, stabilizers or vehicle with which a therapeutic agent is administered. A "pharmaceutically acceptable carrier" is a carrier that is nontoxic to the cell or mammal being exposed thereto at the dosages and concentrations employed, which can be sterile liquids, such as water and oils, including those of petroleum, animal, vegetable or synthetic origin, such as peanut oil, soybean oil, mineral oil, sesame oil and the like.

As used herein, and unless otherwise specified, the term "vector" refers to a substance that is used to introduce a nucleic acid molecule into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecule is expressed in a sufficient amount to produce the desired product (e.g. an anti-BTN1A1 antibody provided herein), and it is further understood that expression levels can be optimized to obtain sufficient expression using methods well known in the art.

As used herein, and unless otherwise specified, the term "host cell" refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, and unless otherwise specified, the term "subject" refers to an animal that is the object of treatment, observation and/or experiment. "Animal" includes vertebrates and invertebrates, such as fish, shellfish, reptiles, birds, and, in particular, mammals. "Mammal" includes, but not limited to, mice, rats, rabbits, guinea pigs, dogs, cats, sheep, goats, cows, horses, primates, such as monkeys, chimpanzees, apes, and humans.

As used herein, and unless otherwise specified, the term "cancer" or "cancerous" refers to the physiological condition in mammals that is typically characterized by unregulated cell growth. Examples of cancer include, but are not limited to, hematological cancers and solid tumors.

As used herein, and unless otherwise specified, the term "treat," "treating," "treatment," when used in reference to a cancer patient, refer to an action that reduces the severity of the cancer, or retards or slows the progression of the cancer, including (a) inhibiting the cancer growth, or arresting development of the cancer, and (b) causing regression of the cancer, or delaying or minimizing one or more symptoms associated with the presence of the cancer.

As used herein, and unless otherwise specified, the term "therapeutically effective amount" refers to the amount of an agent (e.g., an antibody described herein or any other agent described herein) that is sufficient to reduce and/or ameliorate the severity and/or duration of a given disease, disorder or condition, and/or a symptom related thereto. A therapeutically effective amount of an agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody provided herein). A therapeutically effective amount of a substance/molecule/agent of the present disclosure (e.g., an anti-BTN1A1 antibody) can vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects.

As used herein, and unless otherwise specified, the term "administer" or "administration" refers to the act of injecting or otherwise physically delivering a substance as it exists outside the body into a patient, such as by mucosal, intradermal, intravenous, intramuscular delivery and/or any other method of physical delivery described herein or known in the art. When a disease, disorder or condition, or a symptom thereof, is being treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

5.2 Molecules Having an Antigen Binding Fragment that Immunospecifically Bind to BTN1A1

Provided herein are molecules having an antigen binding fragment that immunospecifically binds to BTN1A1, including anti-BTN1A1 antibodies. In some embodiments, the antigen binding fragment that immunospecifically binds BTN1A1 binds to a fragment, or an epitope of BTN1A1. In some embodiments, the BTN1A1 epitope can be a linear epitope. In some embodiments, the BTN1A1 epitope can be a conformation epitope. In some embodiments, the molecules provided herein that have an antigen binding fragment that immunospecifically binds to BTN1A1 inhibit the immune suppressive function of BTN1A1.

N-glycosylation is a posttranslational modification that is initiated in the endoplasmic reticulum (ER) and subsequently processed in the Golgi (Schwarz and Aebi, Curr. Opin. Struc. Bio., 21(5): 576-582 (2011)). This type of modification is first catalyzed by a membrane-associated oligosaccharyl transferase (OST) complex that transfers a preformed glycan composed of oligosaccharides to an asparagine (Asn) side-chain acceptor located within the NXT motif (-Asn-X-Ser/Thr-) (Cheung and Reithmeier, Methods, 41: 451-459 (2007); Helenius and Aebi, Science, 291(5512):2364-9 (2001)). The addition or removal of saccharides from the preformed glycan is mediated by a group of glycotransferases and glycosidases, respectively, which tightly regulate the N-glycosylation cascade in a cell- and location-dependent manner.

In some embodiments, the molecules have an antigen binding fragment that selectively binds to one or more glycosylation motifs of BTN1A1. In some embodiments, the antigen binding fragment immunospecifically binds to a glycopeptide having a glycosylation motif and the adjacent peptide. In some embodiments, the antigen binding fragment immunospecifically binds to a peptide sequence that is located near one or more of the glycosylation motifs in three dimensions.

In some embodiments, the antigen binding fragment binds to glycosylated BTN1A1 with Kd less than at least 30%, 40%, 50%, 60%, 70%, 80%, or 90% of the Kd exhibited relative to unglycosylated BTN1A1. In certain embodiments, the antigen binding fragment binds to glycosylated BTN1A1 with Kd less than 50% of the Kd exhibited relative to unglycosylated BTN1A1. In some embodiments, the antigen binding fragment binds to glycosylated BTN1A1 with Kd that is less than 1%, 2%, 3%, 4%, 5%, 6%, 7%, 8%, 9%, 10%, 15%, 20%, 30%, 40%, 50% of the Kd exhibited relative to unglycosylated BTN1A1. In further aspects, the antigen binding fragment binds to glycosylated BTN1A1 with Kd at least 10 times less than the Kd exhibited relative to unglycosylated BTN1A1.

The specific glycosylation sites of a particular BTN1A1 isoform or variant can vary from amino acids at position 55, 215, or 449 of that particular BTN1A1 isoform or variant. In those circumstances, a person of ordinary skill in the art would be able to determine the glycosylation sites of any particular BTN1A1 isoform or variant that correspond to N55, N215, and N449 of the human BTN1A1 exemplified above based on sequence alignment and other common knowledge in the art. As such, provided herein are also molecules having an antigen binding fragment that immunospecifically binds to a glycosylated form of a BTN1A1 isoform or variant relative to the unglycosylated BTN1A1 isoform or variant. The glycosylated sites of a BTN1A1 isoform or variant can be the corresponding sites of N55, N215, and N449 of human BTN1A1 sequence as provided above.

In some embodiments, the molecules have an antigen binding fragment that immunospecifically binds to glycosylated BTN1A1. In some aspects, the antigen binding fragment immunospecifically binds to BTN1A1 glycosylated at positions N55, N215, and/or N449. In some aspects, the antigen binding fragment immunospecifically binds to BTN1A1 glycosylated at position N55. In some aspects, the antigen binding fragment immunospecifically binds to BTN1A1 glycosylated at position N215. In some aspects, the antigen binding fragment immunospecifically binds to BTN1A1 glycosylated at position N449. In some aspects, the antigen binding fragment immunospecifically binds to one or more glycosylation motifs. In some aspects, the antigen binding fragment immunospecifically binds to BTN1A1 glycosylated at positions N55 and N215. In some aspects, the antigen binding fragments immunospecifically binds to BTN1A1 glycosylated at positions N215 and N449. In some aspects, the antigen binding fragments immunospecifically binds to BTN1A1 glycosylated at positions N55 and N449. In some aspects, the antigen binding fragments immunospecifically binds to BTN1A1 glycosylated at positions N55, N215 and N449.

In some embodiments, the molecules have an antigen binding fragment that immunospecifically binds to glycosylated BTN1A1, wherein the antigen binding fragment preferentially binds glycosylated BTN1A1 over non-glycosylated BTN1A1. In some aspects, the antigen binding fragments preferentially bind to BTN1A1 glycosylated at positions N55, N215, and/or N449 over non-glycosylated BTN1A1. In some aspects, the antigen binding fragments preferentially bind to BTN1A1 glycosylated at position N55 over non-glycosylated BTN1A1. In some aspects, the antigen binding fragments preferentially bind to BTN1A1 glycosylated at position N215 over non-glycosylated BTN1A1. In some aspects, the antigen binding fragments preferentially bind to BTN1A1 glycosylated at position N449 over non-glycosylated BTN1A1. In some aspects, the antigen binding fragments preferentially bind to one or more glycosylation motifs. In some aspects, the antigen binding fragments preferentially binds to BTN1A1 glycosylated at positions N55 and N215 over non-glycosylated BTN1A1. In some aspects, the antigen binding fragments preferentially bind to BTN1A1 glycosylated at positions N215 and N449 over non-glycosylated BTN1A1. In some aspects, the antigen binding fragments preferentially bind to BTN1A1 glycosylated at positions N55 and N449 over non-glycosylated BTN1A1. In some aspects, the antigen binding fragments preferentially binds to BTN1A1 glycosylated at positions N55, N215 and N449 over non-glycosylated BTN1A1.

The preferential binding can be determined by binding affinity. For example, an antibody or antigen binding fragment that preferentially binds to the glycosylated BTN1A1 can bind to glycosylated BTN1A1 with a Kd less than the Kd exhibited relative to unglycosylated BTN1A1. In some embodiments, the antibody or antigen binding fragment binds to glycosylated BTN1A1 with Kd less than half of the Kd exhibited relative to unglycosylated BTN1A1. In some embodiments, the antibody or antigen binding fragment binds to glycosylated BTN1A1 with Kd at least 10 times less than the Kd exhibited relative to unglycosylated BTN1A1. In some embodiments, the antibody or antigen binding fragment binds to glycosylated BTN1A1 with Kd that is about 75% of the Kd exhibited relative to unglycosylated BTN1A1. In some embodiments, the antibody or antigen binding fragment binds to glycosylated BTN1A1 with Kd that is about 50% of the Kd exhibited relative to unglycosylated BTN1A1. In some embodiments, the antibody or antigen binding fragment binds to glycosylated BTN1A1 with Kd that is about 25% of the Kd exhibited relative to unglycosylated BTN1A1. In some embodiments, the antibody or antigen binding fragment binds to glycosylated BTN1A1 with Kd that is about 10% of the Kd exhibited relative to unglycosylated BTN1A1. In some embodiments, the antibody or antigen binding fragment binds to glycosylated BTN1A1 with Kd that is about 5% of the Kd exhibited relative to unglycosylated BTN1A1. In some embodiments, the antibody or antigen binding fragment binds to glycosylated BTN1A1 with Kd that is bout 2.5% of the Kd exhibited relative to unglycosylated BTN1A1. In some embodiments, the antibody or antigen binding fragment binds to glycosylated BTN1A1 with Kd that is bout 1% of the Kd exhibited relative to unglycosylated BTN1A1.

The preferential binding can also be determined by in a binding assay as indicated by, for example, fluorescence intensity ("MFI"). For example, an antibody or antigen binding fragment that preferentially binds to the glycosylated BTN1A1 can bind to glycosylated BTN1A1 with an MFI that is higher than the MFI as exhibited relative to unglycosylated BTN1A1. In some embodiments, the antibody or antigen binding fragment binds to glycosylated BTN1A1 with an MFI that is at least twice as high as the MFI as exhibited relative to unglycosylated BTN1A1. In some embodiments, antibody or the antigen binding fragment binds to glycosylated BTN1A1 with an MFI that is at least three times as high as the MFI as exhibited relative to unglycosylated BTN1A1. In some embodiments, antibody or the antigen binding fragment binds to glycosylated BTN1A1 with an MFI that is at least five times as high as the MFI as exhibited relative to unglycosylated BTN1A1. In some embodiments, antibody or the antigen binding fragment binds to glycosylated BTN1A1 with an MFI that is at least ten times as high as the MFI as exhibited relative to unglycosylated BTN1A1. In some embodiments, antibody or the antigen binding fragment binds to glycosylated BTN1A1 with an MFI that is at least fifteen times as high as the MFI as exhibited relative to unglycosylated BTN1A1. In some embodiments, antibody or the antigen binding fragment binds to glycosylated BTN1A1 with an MFI that is at least twenty times as high as the MFI as exhibited relative to unglycosylated BTN1A1.

In some aspects, the antigen binding fragments immunospecifically mask BTN1A1 glycosylation at positions N55, N215, and/or N449. In some aspects, the antigen binding fragments immunospecifically mask BTN1A1 glycosylation at position N55. In some aspects, the antigen binding fragments immunospecifically mask BTN1A1 glycosylation at position N215. In some aspects, the antigen binding fragments immunospecifically mask BTN1A1 glycosylation at position N449. In some aspects, the antigen binding fragments immunospecifically mask one or more glycosylation motifs of BTN1A1. In some aspects, the antigen binding fragments immunospecifically mask BTN1A1 glycosylation at positions N55 and N215. In some aspects, the antigen binding fragments immunospecifically mask BTN1A1 glycosylation at positions N215 and N449. In some aspects, the antigen binding fragments immunospecifically mask BTN1A1 glycosylation at positions N55 and N449. In some aspects, the antigen binding fragments immunospecifically mask BTN1A1 glycosylation at positions N55, N215 and N449.

5.2.1. Antibodies and Other Molecules Having an Antigen Binding Fragment

In some embodiments, the anti-BTN1A1 antibody or anti-glycosylated BTN1A1 antibody can be an IgG, IgM, IgA, IgD, or IgE. The anti-BTN1A1 antibody or anti-glycosylated BTN1A1 antibody can also be a chimeric antibody, an affinity matured antibody, a humanized antibody, or a human antibody. The anti-BTN1A1 antibody or anti-glycosylated BTN1A1 antibody can also be a camelized antibody, an intrabody, an anti-idiotypic (anti-Id) antibody. In some embodiments, the anti-BTN1A1 antibody or anti-glycosylated BTN1A1 antibody can be a polyclonal antibody or monoclonal antibody.

Antibodies can be produced from any animal source, including birds and mammals. In some embodiments, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is hereby incorporated by reference in its entirety. These techniques are further described in Marks (1992); Stemmer (1994); Gram et al. (1992); Barbas et al. (1994); and Schier et al. (1996); which are hereby incorporated by reference in their entireties.

Methods for producing polyclonal antibodies in various animal species, as well as for producing monoclonal antibodies of various types, including humanized, chimeric, and fully human, are well known in the art. For example, the following U.S. patents provide enabling descriptions of such methods and are herein incorporated by reference: U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,891,024; 7,407,659; and 8,178,098, which are hereby incorporated by reference in their entireties.

The molecules having an antigen binding fragment that immunospecifically binds BTN1A1 or specifically glycosylated BTN1A1, including the anti-BTN1A1 antibodies or anti-glycosylated BTN1A1 antibodies, can also be produced by any method known in the art useful for the production of polypeptides, e.g., in vitro synthesis, recombinant DNA production, and the like. The humanized antibodies can be produced by recombinant DNA technology. The antibodies described herein can also be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757; which are hereby incorporated by reference in their entireties. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992); which are hereby incorporated by reference in their entireties. Additional information concerning the generation, design and expression of recombinant antibodies can be found in Mayforth, Designing Antibodies, Academic Press, San Diego (1993).

In certain embodiments, the anti-BTN1A1 antibody or anti-glycosylated BTN1A1 antibody is a human antibody. Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a BTN1A1 polypeptide, or a glycosylated BTN1A1 polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, therapeutically useful IgG, IgA, IgM and IgE antibodies can be produced. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633, 425, 5,569,825, 5,661,016, 5,545,806, 5,814,318, and 5,939, 598, which are incorporated by reference herein in their entirety. In addition, companies such as Abgenix, Inc. (Freemont, Calif) and Medarex (Princeton, N.J.) can be engaged to provide human antibodies directed against a selected antigen using technology similar to that described above.

In some embodiments, the anti-BTN1A1 antibody or anti-glycosylated BTN1A1 antibody is a chimeric antibody, for example, an antibody having antigen binding sequences from a non-human donor grafted to a heterologous non-human, human or humanized sequence (e.g., framework and/or constant domain sequences). In one embodiment, the non-human donor is a rat. In one embodiment, an antigen binding sequence is synthetic, e.g., obtained by mutagenesis (e.g., phage display screening of a human phage library, etc.). In one embodiment, a chimeric antibody can have murine V regions and human C regions. In one embodiment, the murine light chain V region is fused to a human kappa light chain. In one embodiment, the murine heavy chain V region is fused to a human IgG1 C region.

Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807, 715, 4,816,567, and 4,816,397; all of which are hereby incorporated by references in their entireties. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519, 596; Padlan, 1991, *Molecular Immunology* 28(4/5):489-498; Studnicka et al., 1994, *Protein Engineering* 7:805; and Roguska et al., 1994, *Proc. Natl. Acad. Sci. USA* 91:969), and chain shuffling (U.S. Pat. No. 5,565,332); all of which are hereby incorporated by references in their entireties.

An exemplary process for the production of the recombinant chimeric anti-BTN1A1 antibodies can include the following: a) constructing, by conventional molecular biology methods, an expression vector that encodes and expresses an antibody heavy chain in which the CDRs and variable region of the murine anti-BTN1A1 (or anti-glycosylated BTN1A1) monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-BTN1A1 (or anti-glycosylated BTN1A1) monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized anti-BTN1A1 antibodies can include the following: a) constructing, by conventional molecular biology methods, an expression vector that encodes and expresses an antibody heavy chain in which the CDRs and a minimal portion of the variable region framework that are required to retain donor antibody binding specificity are derived from a non-human immunoglobulin, such as the murine anti-BTN1A1 (or anti-glycosylated BTN1A1) monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as the murine anti-BTN1A1 (or anti-glycosylated BTN1A1) monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells can be co-transfected with such expression vectors, which can contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains can comprise cDNA or genomic DNA or both. The host cell used to express the recombinant antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and can be selected so as to have the desired expression and regulatory characteristics in the selected host cell. Other cell lines that can be used include, but are not limited to, CHO-K1, NSO, and PER.C6 (Crucell, Leiden, Netherlands). Furthermore, codon usage can by optimized when host cell is selected to account for species specific codon usage bias and enhance protein expression. For example, for CHO cell expression the DNA encoding the antibodies can incorporate codons used preferentially by *Cricetulus griseus* (from where Chinese Hamster ovaries cells are derived. Methods of codon optimization may be employed to facilitate improved expression by a desired host cell (see, e.g., Wohlgemuth, I. et al., *Philos. Trans. R. Soc. Lond. B Biol. Sci.* 366(1580): 2979-2986 (2011); Jestin, J. L. et al., *J. Mol. Evol.* 69(5): 452-457 (2009); Bollenbach, T. et al., *Genome Res.* 17(4): 401-404(2007); Kurland, C. G. et al., *Prog. Nucleic Acid Res. Mol. Biol.* 31:191-219 (1984); Grosjean, H. et al., *Gene* 18(3): 199-209(1982)).

In some embodiments, the anti-BTN1A1 antibodies or anti-glycosylated BTN1A1 antibodies can be monoclonal antibodies. In some embodiments, the anti-BTN1A1 antibodies or anti-glycosylated BTN1A1 antibodies can be polyclonal antibodies. Animals can be inoculated with an antigen, such as a BTN1A1 polypeptide or glycosylated BTN1A1 polypeptide in order to produce antibodies specific for a BTN1A1 polypeptide or a glycosylated BTN1A1 polypeptide. Frequently an antigen is bound or conjugated to another molecule to enhance the immune response. A conjugate can be any peptide, polypeptide, protein, or non-proteinaceous substance bound to an antigen that is used to elicit an immune response in an animal. Antibodies produced in an animal in response to antigen inoculation have a variety of non-identical molecules (polyclonal antibodies) made from a variety of individual antibody producing B lymphocytes. Given the correct conditions for polyclonal antibody production in an animal, most of the antibodies in the animal's serum recognize the collective epitopes on the antigenic compound to which the animal has been immunized.

This specificity can be further enhanced by affinity purification to select only those antibodies that recognize the antigen or epitope of interest. The methods for generating monoclonal antibodies (MAbs) can begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and can provide certain advantages. Mice (e.g., BALB/c mice) are routinely used and generally give a high percentage of stable fusions.

Hybridoma technology involves the fusion of a single B lymphocyte from a mouse previously immunized with a BTN1A1 polypeptide or glycosylated BTN1A1 polypeptide with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) can be produced.

In one embodiment, the antibody is an immunoglobulin single variable domain derived from a camelid antibody, preferably from a heavy chain camelid antibody, devoid of light chains, which are known as $V_HH$ domain sequences or Nanobodies™. A Nanobody™ (Nb) is the smallest functional fragment or single variable domain ($V_HH$) of a naturally occurring single-chain antibody and is known to the person skilled in the art. They are derived from heavy chain only antibodies seen in camelids (Hamers-Casterman et al., *Nature*, 363(6428):446-8 (1993); Desmyter et al., *Nat Struct Biol.*, 3(9):803-11. (1996)). In the family of "camelids," immunoglobulins devoid of light polypeptide chains are found. "Camelids" comprise old world camelids (*Camelus bactrianus* and *Camelus dromedarius*) and new world camelids (for example, *Lama paccos*, *Lama glama*, *Lama guanicoe* and *Lama vicugna*). The single variable domain heavy chain antibody is herein designated as a Nanobody™ or a $V_HH$ antibody. The small size and unique biophysical properties of Nbs excel conventional antibody fragments for the recognition of uncommon or hidden epitopes and for binding into cavities or active sites of protein targets. Further, Nbs can be designed as multi-specific and multi-valent antibodies, attached to reporter molecules, or humanzied. Nbs are stable, survive the gastro-intestinal system and can easily be manufactured.

Unifying two antigen binding sites of different specificity into a single construct, bispecific antibodies have the ability to bring together two discreet antigens with exquisite specificity and therefore have great potential as therapeutic agents. Bispecific antibodies can be made by fusing two hybridomas, each capable of producing a different immunoglobulin. Bispecific antibodies can also be produced by joining two scFv antibody fragments while omitting the Fc portion present in full immunoglobulins. Each scFv unit in such constructs can be made up of one variable domain from each of the heavy (VH) and light (VL) antibody chains, joined with one another via a synthetic polypeptide linker, the latter often being genetically engineered so as to be minimally immunogenic while remaining maximally resistant to proteolysis. Respective scFv units can be joined by a number of techniques including incorporation of a short (usually less than 10 amino acids) polypeptide spacer bridging the two scFv units, thereby creating a bispecific single chain antibody. The resulting bispecific single chain antibody is therefore a species containing two VH/VL pairs of different specificity on a single polypeptide chain, wherein the VH and VL domains in a respective scFv unit are separated by a polypeptide linker long enough to allow intramolecular association between these two domains, and wherein the thusly formed scFv units are contiguously tethered to one another through a polypeptide spacer kept short enough to prevent unwanted association between, for example, the VH domain of one scFv unit and the VL of the other scFv unit.

Examples of molecules having an antigen binding fragment that immunospecifically binds to BTN1A1 or glycosylated BTN1A1, include, without limitation: (i) the Fab fragment, consisting of VL, VH, CL, and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker that allows the two domains to associate to form a binding domain; (viii) bi-specific single chain Fv dimers (see U.S. Pat. No. 5,091,513); and (ix) diabodies, multivalent, or multispecific fragments constructed by gene fusion (U.S. Patent Appln. Publn. No. 20050214860). Fv, scFv, or diabody molecules may be stabilized by the incorporation of disulfide bridges linking the VH and VL domains. Minibodies having a scFv joined to a CH3 domain can also be made (Hu et al., *Cancer Res.*, 56(13):3055-61(1996)).

Antibody-like binding peptidomimetics are also contemplated in embodiments. Murali et al., *Cell Mol. Biol.*, 49 (2):209-216 (2003) describe "antibody like binding peptidomimetics" (ABiPs), which are peptides that act as pared-down antibodies and have certain advantages of longer serum half-life as well as less cumbersome synthesis methods, which is hereby incorporated by reference in its entirety.

5.2.2. Anti-BTN1A1 Antibodies

A total of 68 mouse monoclonal antibodies that immunospecifically bind to BTN1A1 were cloned and characterized (Table 5 below). For example, the antibody designated as STC810 (also referred to as STC838) showed glycosylation specific binding with high affinity (KD between STC810 and hBTN1A1-Fc was determined to be 1.81 nM by Biacore, and 2.12 nM by Octet). As described in detail below, treatment of the monoclonal anti-BTN1A1 antibody, e.g., STC810, enhanced T-cell dependent apoptosis of cancer cells, inhibited proliferation of cancer cells, and also resulted in glycosylation dependent internalization of BTN1A1 to lysosomes. The epitopes of STC810 are also provided herein. Accordingly, provided herein are also anti-BTN1A1 antibodies with specific sequence features, anti-BTN1A1 antibodies that immunospecifically bind to specific epitopes, as well as the uses thereof in cancer treatment.

In certain embodiments, the anti-BTN1A1 antibody provided herein comprises a VH domain, VL domain, VH CDR1, VH CDR2, VH CDR3, VL CDR1, VL CDR2, and/or VL CDR3 of monoclonal antibody STC810 described herein, or a humanized variant thereof. In certain embodiments, the anti-BTN1A1 antibody can further comprise a VH FR1, VH FR2, VH FR3, VH FR4, VL FR1, VL FR2, VL FR3, and/or VL FR4 of a human germline immunoglobulin amino acid sequence or a variant thereof.

In certain embodiments, the anti-BTN1A1 antibody comprises less than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3. In specific embodiments, the antibody comprises or consists of one, two, three, four, or five CDRs selected from the group consisting of VH CDR1, VH CDR2, VH CDR3, VL CDR1, VL CDR2, and/or VL CDR3 of the monoclonal antibody STC810 described herein, or a humanized variant thereof. In specific embodiments, the antibody further comprises a VH FR1, VH FR2, VH FR3, VH FR4, VL FR1, VL FR2, VL FR3, and/or VL FR4 of a human germline immunoglobulin amino acid sequence or a variant thereof.

In specific embodiments, the antibody is a humanized antibody, a monoclonal antibody, a recombinant antibody, an antigen binding fragment or any combination thereof. In particular embodiments, the antibody is a humanized monoclonal antibody, or antigen binding fragment thereof.

In some embodiments, provided herein are antibodies, including humanized antibodies, (i) that competitively block (e.g., in a dose-dependent manner) an anti-BTN1A1 antibody provided herein from binding to a BTN1A1 polypeptide (e.g., a cell surface-expressed or soluble BTN1A1), a BTN1A1 fragment, or a BTN1A1 epitope and/or (ii) that bind to a BTN1A1 epitope that is bound by an anti-BTN1A1 antibody (e.g., humanized anti-BTN1A1 antibodies) provided herein. In other embodiments, the antibody competitively blocks (e.g., in a dose-dependent manner) monoclonal antibody STC810 described herein or a humanized variant thereof from binding to a BTN1A1 polypeptide (e.g., a cell surface-expressed or soluble BTN1A1), a BTN1A1 fragment, or a BTN1A1 epitope. In other embodiments, the antibody binds to a BTN1A1 epitope that is bound (e.g., recognized) by monoclonal antibody BTN1A1 described herein or a humanized variant thereof (e.g. humanized anti-BTN1A1 antibodies).

TABLE 2a

Sequences of heavy chain variable (VH) region and light chain variable (VL) region of mouse monoclonal anti-human BTN1A1 Antibody STC810

| | DNA sequence | Protein sequence |
| --- | --- | --- |
| heavy chain | GAGGTCCAGCTGCAGCAGTCTGGACCTG<br>AGCTGGTGAAGCCTGGGGCTTCAGTGA<br>AGATATCCTGCAAGGCTTCTGGATACAC<br>ATTCACTCACTACAACATGGACTGGGTG<br>AAGCAGAGCCATGGAAAGAGCCTTGAA<br>TGGATTGGATATATTTATCCTTCCAATG<br>GTGGTACTGGCTACAACCAGAAATTCAA<br>GAGCAGGGCCACATTGACTGTAGACAA<br>GTCCTCCAGCACAGCCTACATGGAACTC<br>CACAGCCTGACATCTGAGGACTCTGCAG<br>TCTATTACTGTGCAAGAGGGGCCTATCA<br>CTACGGTAGTTCCTACGCCTACTGGTAC<br>TTCGATGTCTGGGGCGCAGGGACCACG<br>GTCACCGTCTCCTCA<br>(SEQ ID NO: 4) | EVQLQQSGPELVKPGASVKIS<br>CKASGYTFTHYNMDWVKQS<br>HGKSLEWIGYIYPSNGGTGY<br>NQKFKSRATLTVDKSSSTAY<br>MELHSLTSEDSAVYYCARGA<br>YHYGSSYAYWYFDVWGAGT<br>TVTVSS<br>(SEQ ID NO: 3) |
| Kappa Light chain | GATATCCAGATGACACAGACTACATCCT<br>CCCTGTCTGCCTCTCTGGGAGACAGAGT<br>CACCATCAGTTGCAGTGCAAGTCAGGAC<br>ATTAGCAATTATTTAAACTGGTATCAGC<br>AGAAACCAGATGAAACTGTTAAACTCCT<br>GATCTCTTACACATCAAGTTTACACTCA<br>GGAGTCCCATCAAGATTCAGTGGCAGTG<br>GGTCTGGGACAGATTATTCTCTCACCAT<br>CAGCAACCTGGCACCTGAAGATATTGCC<br>ACTTACTATTGTCAGCAGTCTAGTAAGC<br>TTCCATTCACGTTCGGCTCGGGGACAGA<br>GTTGGAAATAAAACGGGCT<br>(SEQ ID NO: 6) | DIQMTQTTSSLSASLGDRVTI<br>SCSASQDISNYLNWYQQKPD<br>ETVKLLISYTSSLHSGVPSRFS<br>GSGSGTDYSLTISNLAPEDIAT<br>YYCQQSSKLPFTFGSGTELEI<br>KRA<br>(SEQ ID NO: 5) |

TABLE 2b

CDR Sequences of mouse monoclonal anti-human BTN1A1 Antibody STC810

| | Region definition | CDR1 | CDR2 | CDR3 |
|---|---|---|---|---|
| Heavy chain | Chothia | (SEQ ID NO: 7) GYTFTHY | (SEQ ID NO: 8) YPSNGG | (SEQ ID NO: 9) GAYHYGSSYAYWYFDV |
| | AbM | (SEQ ID NO: 10) GYTFTHYNMD | (SEQ ID NO: 11) YIYPSNGGTG | (SEQ ID NO: 12) GAYHYGSSYAYWYFDV |
| | Kabat | (SEQ ID NO: 13) HYNMD | (SEQ ID NO: 14) YIYPSNGGTGYNQKFKS | (SEQ ID NO: 15) GAYHYGSSYAYWYFDV |
| | Contact | (SEQ ID NO: 16) THYNMD | (SEQ ID NO: 17) WIGYIYPSNGGTG | (SEQ ID NO: 18) ARGAYHYGSSYAYWYFD |
| Kappa light chain | Chothia | (SEQ ID NO: 19) SASQDISNYLN | (SEQ ID NO: 20) YTSSLHS | (SEQ ID NO: 21) QQSSKLPFT |
| | AbM | (SEQ ID NO: 22) SASQDISNYLN | (SEQ ID NO: 23) YTSSLHS | (SEQ ID NO: 24) QQSSKLPFT |
| | Kabat | (SEQ ID NO: 25) SASQDISNYLN | (SEQ ID NO: 26) YTSSLHS | (SEQ ID NO: 27) QQSSKLPFT |
| | Contact | (SEQ ID NO: 28) SNYLNWY | (SEQ ID NO: 29) LLISYTSSLH | (SEQ ID NO: 30) QQSSKLPF |

Accordingly, provided herein are molecules having an antigen binding fragment that immunospecifically binds to BTN1A1 or glycosylated BTN1A1 with the following sequence features. In some embodiments, the molecules provided herein have an antigen binding fragment that has (a) a heavy chain variable (VH) region comprising: (1) a VH CDR1 having an amino acid sequence of SEQ ID NOS: 7, 10, 13, or 16; (2) a VH CDR2 having an amino acid sequence SEQ ID NOS: 8, 11, 14 or 17; and (3) a VH CDR3 having an amino acid sequence of SEQ ID NOS: 9, 12, 15 or 18; and/or (b) a light chain variable (VL) region comprising: (1) a VL CDR1 having an amino acid sequence of SEQ ID NOS: 19, 22, 25 or 28; (2) a VL CDR2 having an amino acid sequence of SEQ ID NOS: 20, 23, 26 or 29; and (3) a VL CDR3 having an amino acid sequence of SEQ ID NOS: 21, 24, 27 or 30. In some embodiments, provided herein are antibodies having (a) a heavy chain variable (VH) region comprising: (1) a VH CDR1 having an amino acid sequence of SEQ ID NOS: 7, 10, 13, or 16; (2) a VH CDR2 having an amino acid sequence SEQ ID NOS: 8, 11, 14 or 17; and (3) a VH CDR3 having an amino acid sequence of SEQ ID NOS: 9, 12, 15 or 18; and/or (b) a light chain variable (VL) region comprising: (1) a VL CDR1 having an amino acid sequence of SEQ ID NOS: 19, 22, 25 or 28; (2) a VL CDR2 having an amino acid sequence of SEQ ID NOS: 20, 23, 26 or 29; and (3) a VL CDR3 having an amino acid sequence of SEQ ID NOS: 21, 24, 27 or 30. The antibody can be a monoclonal antibody. The antibody can be a humanized antibody.

In some embodiments, the molecules provided herein have an antigen binding fragment that has a heavy chain variable (VH) region comprising: (1) a VH CDR1 having an amino acid sequence of SEQ ID NOS: 7, 10, 13 or 16; (2) a VH CDR2 having an amino acid sequence of SEQ ID NOS: 8, 11, 14 or 17; and/or (3) a VH CDR3 having an amino acid sequence of SEQ ID NOS: 9, 12, 15 or 18. In some embodiments, the heavy chain variable (VH) region comprises (1) a VH CDR1 having an amino acid sequence of SEQ ID NOS: 7, 10, 13 or 16; and (2) a VH CDR2 having an amino acid sequence of SEQ ID NOS: 8, 11, 14 or 17. In some embodiments, the heavy chain variable (VH) region comprises (1) a VH CDR1 having an amino acid sequence of SEQ ID NOS: 7, 10, 13 or 16; and (3) a VH CDR3 having an amino acid sequence of SEQ ID NOS: 9, 12, 15 or 18. In some embodiments, the molecules provided herein have an antigen binding fragment that has a heavy chain variable (VH) region comprising: (1) a VH CDR1 having an amino acid sequence of SEQ ID NOS: 7, 10, 13 or 16; and (3) a VH CDR3 having an amino acid sequence of SEQ ID NOS: 9, 12, 15 or 18.

In some embodiments, the molecules provided herein have an antigen binding fragment that has a heavy chain variable (VH) region comprising a VH CDR1 having an amino acid sequence of SEQ ID NOS: 7, 10, 13 or 16. The VH CDR1 can have an amino acid sequence of SEQ ID NO: 7. The VH CDR1 can have an amino acid sequence of SEQ ID NO: 10. The VH CDR1 can have an amino acid sequence of SEQ ID NO: 13. The VH CDR1 can have an amino acid sequence of SEQ ID NO: 16.

In some embodiments, the molecules provided herein have an antigen binding fragment that has a heavy chain variable (VH) region comprising a VH CDR2 having an amino acid sequence of SEQ ID NOS: 8, 11, 14 or 17. The VH CDR2 can have an amino acid sequence of SEQ ID NO: 8. The VH CDR2 can have an amino acid sequence of SEQ ID NO: 11. The VH CDR2 can have an amino acid sequence of SEQ ID NO: 14. The VH CDR2 can have an amino acid sequence of SEQ ID NO: 17.

In some embodiments, the molecules provided herein have an antigen binding fragment that has a heavy chain variable (VH) region comprising a VH CDR3 having an amino acid sequence of SEQ ID NOS: 9, 12, 15 or 18. The VH CDR3 can have an amino acid sequence of SEQ ID NO: 9. The VH CDR3 can have an amino acid sequence of SEQ ID NO: 12. The VH CDR3 can have an amino acid sequence of SEQ ID NO: 15. The VH CDR3 can have an amino acid sequence of SEQ ID NO: 20.

In some embodiments, the molecules provided herein have an antigen binding fragment that has a heavy chain variable (VH) region comprising: (1) a VH CDR1 having an amino acid sequence of SEQ ID NO: 7; (2) a VH CDR2 having an amino acid sequence of SEQ ID NO: 8; and/or (3) a VH CDR3 having an amino acid sequence of SEQ ID NO: 9.

In some embodiments, the molecules provided herein have an antigen binding fragment that has a heavy chain variable (VH) region comprising: (1) a VH CDR1 having an amino acid sequence of SEQ ID NO: 10; (2) a VH CDR2 having an amino acid sequence of SEQ ID NO: 11; and/or (3) a VH CDR3 having an amino acid sequence of SEQ ID NO: 12.

In some embodiments, the molecules provided herein have an antigen binding fragment that has a heavy chain variable (VH) region comprising: (1) a VH CDR1 having an amino acid sequence of SEQ ID NO: 13; (2) a VH CDR2 having an amino acid sequence of SEQ ID NO: 14; and/or (3) a VH CDR3 having an amino acid sequence of SEQ ID NO: 15.

In some embodiments, the molecules provided herein have an antigen binding fragment that has a heavy chain variable (VH) region comprising: (1) a VH CDR1 having an amino acid sequence of SEQ ID NO: 16; (2) a VH CDR2 having an amino acid sequence of SEQ ID NO: 17; and/or (3) a VH CDR3 having an amino acid sequence of SEQ ID NO: 18.

In some embodiments, the molecules provided herein have an antigen binding fragment that has a heavy chain variable (VH) region that has the amino acid sequence of SEQ ID NO: 3. The molecule can be an antibody. The antibody can be a monoclonal antibody. The antibody can be a humanized antibody.

In some embodiments, the molecules provided herein have an antigen binding fragment that has a light chain variable (VL) region comprising: (1) a VL CDR1 having an amino acid sequence of SEQ ID NOS: 19, 22, 25 or 28; (2) a VL CDR2 having an amino acid sequence of SEQ ID NOS: 20, 23, 26 or 29; and (3) a VL CDR3 having an amino acid sequence of SEQ ID NOS: 21, 24, 27 or 30.

In some embodiments, the molecules provided herein have an antigen binding fragment that has a light chain variable (VL) region comprising: (1) a VL CDR1 having an amino acid sequence of SEQ ID NOS: 19, 22, 25 or 28; and (2) a VL CDR2 having an amino acid sequence of SEQ ID NOS: 20, 23, 26 or 29. In some embodiments, the molecules provided herein have an antigen binding fragment that has a light chain variable (VL) region comprising: (1) a VL CDR1 having an amino acid sequence of SEQ ID NOS: 19, 22, 25 or 28; and (3) a VL CDR3 having an amino acid sequence of SEQ ID NOS: 21, 24, 27 or 30. In some embodiments, the molecules provided herein have an antigen binding fragment that has a light chain variable (VL) region comprising: (2) a VL CDR2 having an amino acid sequence of SEQ ID NOS: 20, 23, 26 or 29; and (3) a VL CDR3 having an amino acid sequence of SEQ ID NOS: 21, 24, 27 or 30.

In some embodiments, the molecules provided herein have an antigen binding fragment that has a light chain variable (VL) region comprising a VL CDR1 having an amino acid sequence of SEQ ID NOS: 19, 22, 25 or 28. The VL CDR1 can have an amino acid sequence of SEQ ID NO: 19. The VL CDR1 can have an amino acid sequence of SEQ ID NO: 22. The VL CDR1 can have an amino acid sequence of SEQ ID NO: 25. The VL CDR1 can have an amino acid sequence of SEQ ID NO: 28.

In some embodiments, the molecules provided herein have an antigen binding fragment that has a light chain variable (VL) region comprising a VL CDR2 having an amino acid sequence of SEQ ID NOS: 20, 23, 26 or 29. The VL CDR2 can have an amino acid sequence of SEQ ID NO:23. The VL CDR2 can have an amino acid sequence of SEQ ID NO:26. The VL CDR2 can have an amino acid sequence of SEQ ID NO:29.

In some embodiments, the molecules provided herein have an antigen binding fragment that has a light chain variable (VL) region comprising a VL CDR3 having an amino acid sequence of SEQ ID NOS: 21, 24, 27 or 30. The VL CDR3 can have an amino acid sequence of SEQ ID NO: 21. The VL CDR3 can have an amino acid sequence of SEQ ID NO: 24. The VL CDR3 can have an amino acid sequence of SEQ ID NO: 27. The VL CDR3 can have an amino acid sequence of SEQ ID NO:30.

In some embodiments, the molecules provided herein have an antigen binding fragment that has a light chain variable (VL) region that has (1) a VL CDR1 having an amino acid sequence of SEQ ID NO: 19; (2) a VL CDR2 having an amino acid sequence of SEQ ID NO: 20; and/or (3) a VL CDR3 having an amino acid sequence of SEQ ID NO: 21.

In some embodiments, the molecules provided herein have an antigen binding fragment that has a light chain variable (VL) region that has (1) a VL CDR1 having an amino acid sequence of SEQ ID NO: 22; (2) a VL CDR2 having an amino acid sequence of SEQ ID NO: 23; and/or (3) a VL CDR3 having an amino acid sequence of SEQ ID NO: 24.

In some embodiments, the molecules provided herein have an antigen binding fragment that has a light chain variable (VL) region that has (1) a VL CDR1 having an amino acid sequence of SEQ ID NO: 25; (2) a VL CDR2 having an amino acid sequence of SEQ ID NO: 26; and/or (3) a VL CDR3 having an amino acid sequence of SEQ ID NO: 27.

In some embodiments, the molecules provided herein have an antigen binding fragment that has a light chain variable (VL) region that has (1) a VL CDR1 having an amino acid sequence of SEQ ID NO: 28; (2) a VL CDR2 having an amino acid sequence of SEQ ID NO: 29; and/or (3) a VL CDR3 having an amino acid sequence of SEQ ID NO: 30.

In some embodiments, the molecules provided herein have an antigen binding fragment that has a light chain variable (VL) region that has the amino acid sequence of SEQ ID NO: 5. The molecule can be an antibody. The antibody can be a monoclonal antibody. The antibody can be a humanized antibody.

In some embodiments, the molecules provided herein have an antigen binding fragment that has (a) a heavy chain variable (VH) region comprising: (1) a VH CDR1 having an amino acid sequence of SEQ ID NOS: 7, 10, 13 or 16; (2) a VH CDR2 having an amino acid sequence of SEQ ID NOS: 8, 11, 14 or 17; and/or (3) a VH CDR3 having an amino acid sequence of SEQ ID NOS: 9, 12, 15 or 18; and (b) a light chain variable (VL) region comprising: (1) a VL CDR1 having an amino acid sequence of SEQ ID NOS: 19, 22, 25 or 28; (2) a VL CDR2 having an amino acid sequence of SEQ ID NOS: 20, 23, 26 or 29; and/or (3) a VL CDR3 having an amino acid sequence of SEQ ID NOS: 21, 24, 27 or 30. The molecule can be an antibody. The antibody can be a monoclonal antibody. The antibody can be a humanized antibody.

In some embodiments, the molecules provided herein have an antigen binding fragment that has (a) a heavy chain variable (VH) region comprising: (1) a VH CDR1 having an amino acid sequence of SEQ ID NO 7; (2) a VH CDR2 having an amino acid sequence of SEQ ID NO 8; and/or (3) a VH CDR3 having an amino acid sequence of SEQ ID NO 9; and (b) a light chain variable (VL) region comprising: (1) a VL CDR1 having an amino acid sequence of SEQ ID NO: 19; (2) a VL CDR2 having an amino acid sequence of SEQ ID NO: 20; and/or (3) a VL CDR3 having an amino acid sequence of SEQ ID NO: 21. The molecule can be an antibody. The antibody can be a monoclonal antibody. The antibody can be a humanized antibody.

In some embodiments, the molecules provided herein have an antigen binding fragment that has (a) a heavy chain variable (VH) region comprising: (1) a VH CDR1 having an amino acid sequence of SEQ ID NO 10; (2) a VH CDR2 having an amino acid sequence of SEQ ID NO 11; and/or (3) a VH CDR3 having an amino acid sequence of SEQ ID NO 12; and (b) a light chain variable (VL) region comprising: (1) a VL CDR1 having an amino acid sequence of SEQ ID NO: 22; (2) a VL CDR2 having an amino acid sequence of SEQ ID NO: 23; and/or (3) a VL CDR3 having an amino acid sequence of SEQ ID NO: 24. The molecule can be an antibody. The antibody can be a monoclonal antibody. The antibody can be a humanized antibody.

In some embodiments, the molecules provided herein have an antigen binding fragment that has (a) a heavy chain variable (VH) region comprising: (1) a VH CDR1 having an amino acid sequence of SEQ ID NO 13; (2) a VH CDR2 having an amino acid sequence of SEQ ID NO 14; and/or (3) a VH CDR3 having an amino acid sequence of SEQ ID NO 15; and (b) a light chain variable (VL) region comprising: (1) a VL CDR1 having an amino acid sequence of SEQ ID NO: 25; (2) a VL CDR2 having an amino acid sequence of SEQ ID NO: 26; and/or (3) a VL CDR3 having an amino acid sequence of SEQ ID NO: 27. The molecule can be an antibody. The antibody can be a monoclonal antibody. The antibody can be a humanized antibody.

In some embodiments, the molecules provided herein have an antigen binding fragment that has (a) a heavy chain variable (VH) region comprising: (1) a VH CDR1 having an amino acid sequence of SEQ ID NO 16; (2) a VH CDR2 having an amino acid sequence of SEQ ID NO 17; and (3) a VH CDR3 having an amino acid sequence of SEQ ID NO 18; and (b) a light chain variable (VL) region comprising: (1) a VL CDR1 having an amino acid sequence of SEQ ID NO: 28; (2) a VL CDR2 having an amino acid sequence of SEQ ID NO: 29; and (3) a VL CDR3 having an amino acid sequence of SEQ ID NO: 30. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 3 and the VL region that has the the amino acid sequence of SEQ ID NO: 5. The molecule can be an antibody. The antibody can be a monoclonal antibody. The antibody can be a humanized antibody.

In some embodiments, the molecules provided herein is the mouse monoclonal antibody designated as STC810, or a humanized antibody version there of A humanized STC810 antibody can have the VH region, the VL region, or both the VH and VL region of STC810 as described herein. A humanized STC810 antibody can also have six CDR regions (VH CDR1, VH CDR2, VH CDR3, VL CDR1, VL CDR2 and VL CDR3) of STC810 as described herein. The humanized STC810 antibody can also have less than the six CDR regions of STC810. In some embodiments, the humanized STC810 antibody can also have one, two, three, four, or five CDR regions (VH CDR1, VH CDR2, VH CDR3, VL CDR1, VL CDR2 and VL CDR3) of STC810.

Standard techniques known to those of skill in the art can be used to introduce mutations in the nucleotide sequence encoding an antigen binding fragment, or an antibody, provided herein, including, for example, site-directed mutagenesis and PCR-mediated mutagenesis which results in amino acid substitutions. In certain embodiments, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a specific embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In one embodiment, the molecules provided herein having an antigen binding fragment that immunospecifically binds to BTN1A1 or glycosylated BTN1A1 can have an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the murine monoclonal antibody STC810, or an antigen-binding fragment thereof, such as a VH domain or VL domain. In one embodiment, the molecules provided herein can have an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in SEQ ID NOS: 3 or 5. In yet another embodiment, the molecules provided herein can have a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence and/or a VL CDR amino acid sequence depicted in Table 2 above.

In some embodiments, the molecules provided herein can have an amino acid sequence of a VH domain and/or an amino acid sequence a VL domain encoded by a nucleotide sequence that hybridizes to the complement of a nucleotide sequence encoding any one of the VH and/or VL domains depicted in Table 2 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In another embodiment, the molecules provided herein can have an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in Table 2 under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3)

In some embodiments, provided herein are also isolated nucleic acid that encode an amino acid sequence f a VH CDR or an amino acid sequence of a VL CDR depicted in Table 2, or that hybridizes to the complement of a nucleic acid sequence encoding any one of the VH CDRs and/or VL CDRs depicted in Table 2 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, provided herein are also isolated nucleic acid that encode an amino acid sequence of a VH domain and/or an amino acid sequence a VL domain depicted in Table 2, or that hybridizes to the complement of a nucleotide sequence encoding any one of the VH and/or VL domains depicted in Table 2 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 4 or that hybridizes to the complement of a nucleotide sequence of SEQ ID NO: 4 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 6 or that hybridizes to the complement of a nucleotide sequence of SEQ ID NO: 6 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the molecules provided herein can be chemically modified, e.g., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

The molecules provided herein can have a framework region known to those of skill in the art (e.g., a human or non-human fragment). The framework region can, for example, be naturally occurring or consensus framework regions. In specific embodiments, the framework region of an antibody provided herein is human (see, e.g., Chothia et al., 1998, *J. Mol. Biol.* 278:457-479 for a listing of human framework regions, which is incorporated by reference herein in its entirety). See also Kabat et al. (1991) *Sequences of Proteins of Immunological Interest* (U.S. Department of Health and Human Services, Washington, D.C.) 5th ed.

The BTN1A1 epitopes of STC810 were mapped by cross-link analysis. Table 3 summarizes the cross-linked peptides of BTN1A1-Fc and STC810, which represent BTN1A1 epitopes of STC810 (SEQ ID NOS: 31-33). FIG. 12 shows a synthesized epitope of BTN1A1(ECD)-Fc antigen for STC810:

```
                                       (SEQ ID NO: 34)
       LELRWFRKKVSPA
```

```
                                       (SEQ ID NO: 35)
       EEGLFTVAASVIIRDTSAKNV
```

Table 4 summarizes the the cross-linked peptides of BTN1A1-His and STC810, which represent BTN1A1 epitopes of STC810 (SEQ ID NOS: 36-39). FIG. 13 shows a synthesized epitope of BTN1A1(ECD)-His antigen for STC810.

```
                                       (SEQ ID NO: 40)
       GRATLVQDGIAKGRV
```

```
                                       (SEQ ID NO: 41)
       EEGLFTVAASVIIRDTSAKNV
```

TABLE 3

Cross-linked peptides of BTN1A1-Fc with STC810 analyzed by nLC-orbitrap MS/MS.

| Proteolysis | Sequence | Protein 1 | Protein 2 | Sequence protein 1 | Sequence protein 2 |
| --- | --- | --- | --- | --- | --- |
| Chymotrypsin | RKKVSPAVL (SEQ ID NO: 31)-YCARGAY (SEQ ID NO: 42)-a1-b1 | BTN1A1-FC | STC810 HC | 41-49 | 95-101 |
|  | RKKVSPAVL(SEQ ID NO: 31) - YCARGAY(SEQ ID NO: 42)-a2-b1 | BTN1A1-FC | STC810 HC | 41-49 | 95-101 |
|  | RKKVSPAVL(SEQ ID NO: 31) - YCARGAY(SEQ ID NO: 42)-a3-b1 | BTN1A1-FC | STC810 HC | 41-49 | 95-101 |
|  | TVAASVIIRDTSAKNVSCY (SEQ ID NO: 32)TFTHY (SEQ ID NO: 43)-a11-b3 | BTN1A1-FC | STC810 HC | 175-193 | 28-32 |
|  | TVAASVIIRDTSAKNVSCY (SEQ ID NO: 32)-TFTHY (SEQ ID NO: 43)-a11-b4 | BTN1A1-FC | STC810 HC | 175-193 | 28-32 |
|  | TVAASVIIRDTSAKNVSCY (SEQ ID NO: 32)-TFTHY (SEQ ID NO: 43)-a14-b4 | BTN1A1-FC | STC810 HC | 175-193 | 28-32 |
| Thermolysin | IRDTSAKN (SEQ ID NO: 33)FTFGSGTE (SEQ ID NO: 44)-a4-b7 | BTN1A1-FC | STC810LC | 182-189 | 96-105 |

TABLE 4

Cross-linked peptides of BTN1A1-His with STC810 analyzed by nLC-orbitrap MS/MS.

| Proteolysis | Sequence | Protein 1 | Protein 2 | Sequence protein 1 | Sequence protein 2 |
| --- | --- | --- | --- | --- | --- |
| Trypsin | ATLVQDGIAKGR (SEQ ID NO: 36) - SLEWIGYIYPSNGGTGYNQKFKSR (SEQ ID NO: 45)-a10-b11 | BTN1A1-His | STC810 HC | 69-80 | 44-67 |
|  | NPDEEGLFTVAASVIIRDTSAK (SEQ ID NO: 37) -LLISYTSSLHSGVPSR (SEQ ID NO: 46)-a13-b6 | BTN1A1-His | STC810 LC | 167-188 | 46-61 |
|  | NPDEEGLFTVAASVIIRDTSAK (SEQ ID NO: 37) - LLISYTSSLHSGVPSR (SEQ ID NO: 46)-a9-b6 | BTN1A1-His | STC810 LC | 167-188 | 46-61 |
| Chymotrypsin | TVAASVIIRDTSAKNVSCY (SEQ ID NO: 38)-TFTHY (SEQ ID NO: 47)-a11-b3 | BTN1A1-His | STC810 HC | 175-193 | 28-32 |
|  | TVAASVIIRDTSAKNVSCY (SEQ ID NO: 38)-TFTHY (SEQ ID NO: 47)-a5-b3 | BTN1A1-His | STC810 HC | 175-193 | 28-32 |

TABLE 4-continued

Cross-linked peptides of BTN1A1-His with STC810 analyzed by nLC-orbitrap MS/MS.

| Proteolysis | Sequence | Protein 1 | Protein 2 | Sequence protein 1 | Sequence protein 2 |
|---|---|---|---|---|---|
| Thermolysin | AEQXPEYRGRAT (SEQ ID NO: 39)-LHSGVPSR (SEQ ID NO: 48)-a10-b2 | BTN1A1 -His | STC810 LC | 59-70 | 54-61 |

Accordingly, also provided herein are the molecule is an molecules having an antigen binding fragment that competitively blocks (e.g., in a dose-dependent manner) a BTN1A1 epitope described herein. In some embodiments, provided herein are molecules having an antigen binding fragment that competitively block (e.g., in a dose-dependent manner) an BTN1A1 epitope of STC810. In some embodiments, the molecules provided herein have an antigen binding fragment that immunospecifically binds to an epitope of BTN1A1 as described herein. In some embodiments, the molecules provided herein have an antigen binding fragment that immunospecifically binds to an BTN1A1 epitope of STC810. The molecule can be an antibody. The antibody can be a monoclonal antibody. The antibody can be a humanized antibody.

In some embodiments, provided herein are anti-BTN1A1 antibodies that competitively block (e.g., in a dose-dependent manner) a BTN1A1 epitope described herein. In some embodiments, provided herein are anti-BTN1A1 antibodies that competitively block (e.g., in a dose-dependent manner) a BTN1A1 epitope of STC810 as described herein. In some embodiments, the anti-BTN1A1 antibodies provided herein immunospecifically bind to an epitope of BTN1A1 as described herein. In some embodiments, the anti-BTN1A1 antibodies provided herein immunospecifically bind to an BTN1A1 epitope of STC810.

In some embodiments, the molecules having an antigen binding fragment that competitively block (e.g., in a dose-dependent manner) a BTN1A1 epitope, wherein the BTN1A1 epitope has at least five consecutive amino acids of an amino acid sequence of SEQ ID NOS: 31-41. In some embodiments, the molecules provided herein have an antigen binding fragment that immunospecifically binds to an epitope of BTN1A1, wherein the BTN1A1 epitope has at least five consecutive amino acids of an amino acid sequence of SEQ ID NOS: 31-41. The epitope of BTN1A1 can have at least six, at least seven, at least eight, at least nine, at least ten, at least eleven, at least twelve, at least thirteen, at least fourteen, or at least fifteen, consecutive amino acids of an amino acid sequence of SEQ ID NOS: 31-41. The epitope of BTN1A1 can have at least six consecutive amino acids of an amino acid sequence of SEQ ID NOS: 31-41. The epitope of BTN1A1 can have at least seven consecutive amino acids of an amino acid sequence of SEQ ID NOS: 31-41. The epitope of BTN1A1 can have at least eight consecutive amino acids of an amino acid sequence of SEQ ID NOS: 31-41. The epitope of BTN1A1 can have at least nine consecutive amino acids of an amino acid sequence of SEQ ID NOS: 31-41. The epitope of BTN1A1 can have at least ten consecutive amino acids of an amino acid sequence of SEQ ID NOS: 31-41. The epitope of BTN1A1 can have at least eleven consecutive amino acids of an amino acid sequence of SEQ ID NOS: 31-41. The epitope of BTN1A1 can have at least twelve consecutive amino acids of an amino acid sequence of SEQ ID NOS: 31-41. The epitope of BTN1A1 can have at least thirteen consecutive amino acids of an amino acid sequence of SEQ ID NOS: 31-41. The epitope of BTN1A1 can have at least fourteen consecutive amino acids of an amino acid sequence of SEQ ID NOS: 31-41. The epitope of BTN1A1 can have at least fifteen consecutive amino acids of an amino acid sequence of SEQ ID NOS: 31-41. The molecule can be an antibody. The antibody can be a monoclonal antibody. The antibody can be a humanized antibody.

In some embodiments, the molecules having an antigen binding fragment that competitively block (e.g., in a dose-dependent manner) a BTN1A1 epitope, wherein the BTN1A1 epitope has an amino acid sequence of SEQ ID NOS: 31-41. In some embodiments, the molecules provided herein have an antigen binding fragment that immunospecifically binds to an epitope of BTN1A1, wherein the BTN1A1 epitope has an amino acid sequence of SEQ ID NOS: 31, 32, 33, 34, 35, 36, 37, 38, 39, 40 or 41. The epitope of BTN1A1 can have an amino acid sequence of SEQ ID NO: 31. The epitope of BTN1A1 can have an amino acid sequence of SEQ ID NO: 32. The epitope of BTN1A1 can have an amino acid sequence of SEQ ID NO: 33. The epitope of BTN1A1 can have an amino acid sequence of SEQ ID NO: 34. The epitope of BTN1A1 can have an amino acid sequence of SEQ ID NO: 35. The epitope of BTN1A1 can have an amino acid sequence of SEQ ID NO: 36. The epitope of BTN1A1 can have an amino acid sequence of SEQ ID NO: 37. The epitope of BTN1A1 can have an amino acid sequence of SEQ ID NO: 38. The epitope of BTN1A1 can have an amino acid sequence of SEQ ID NO: 39. The epitope of BTN1A1 can have an amino acid sequence of SEQ ID NO: 40. The epitope of BTN1A1 can have an amino acid sequence of SEQ ID NO: 41.

In certain embodiments, the molecules provided herein have a high affinity for BTN1A1, glycosylated BTN1A1 or a polypeptide, or polypeptide fragment or epitope thereof. In one embodiment, the molecules provided herein can be anti-BTN1A1 antibodies that have a higher affinity for a BTN1A1 antibody than known antibodies (e.g., commercially available monoclonal antibodies discussed elsewhere herein). In a specific embodiment, the molecules provided herein can be anti-BTN1A1 antibodies can have a 2- to 10-fold (or more) higher affinity for a BTN1A1 antigen than a known anti-BTN1A1 antibody as assessed by techniques described herein or known to one of skill in the art (e.g., a BIAcore assay). In accordance with these embodiments, the affinity of the antibodies are, in one embodiment, assessed by a BIAcore assay.

In certain embodiments, molecules provided herein can have an antigen binding fragment that binds to BTN1A1, glycosylated BTN1A1 or a polypeptide, or polypeptide fragment or epitope thereof with a dissociation constant (Kd) of no more than 1 µM, no more than 100 nM, no more than 10 nM, no more than 1 nM, or no more than 0.1 nM. In some embodiments, molecules provided herein can be anti-BTN1A1 antibodies having a Kd of no more than 500 nM. In some embodiments, molecules provided herein can be anti-BTN1A1 antibodies having a Kd of no more than 200 nM. In some embodiments, molecules provided herein can be anti-BTN1A1 antibodies having a Kd of no more than 100 nM. In some embodiments, the anti-BTN1A1 antibodies having a Kd of no more than 50 nM. In some embodiments, molecules provided herein can be anti-BTN1A1 antibodies having a Kd of no more than 20 nM. In some embodiments, molecules provided herein can be anti-BTN1A1 antibodies having a Kd of no more than 10 nM. In some embodiments, molecules provided herein can be anti-BTN1A1 antibodies having a Kd of no more than 5 nM. In some embodiments, molecules provided herein can be anti-BTN1A1 antibodies having a Kd of no more than 2 nM. In some embodiments, molecules provided herein can be anti-BTN1A1 antibodies having a Kd of no more than 1 nM. In some embodiments, molecules provided herein can be anti-BTN1A1 antibodies having a Kd of no more than 0.5 nM. In some embodiments, molecules provided herein can be anti-BTN1A1 antibodies having a Kd of no more than 0.1 nM.

In certain embodiments, molecules provided herein can block or neutralize the activities of BTN1A1. The molecule can be a neutralizing antibody. The neutralizing antibody can block the binding the BTN1A1 with its natural ligands and inhibit the signaling pathways mediated by BTN1A1 and/or its other physiological activities. The IC50 of a neutralizing antibody can range between 0.01-10 pg/ml in the neutralization assay. The IC50 of a neutralizing antibody can be no more than 10 μg/ml. The IC50 of a neutralizing antibody can be no more than 8 pg/ml. The IC50 of a neutralizing antibody can be no more than 6 μg/ml. The IC50 of a neutralizing antibody can be no more than 4 μg/ml. The IC50 of a neutralizing antibody can be no more than 2 μg/ml. The IC50 of a neutralizing antibody can be no more than 1 pg/ml. The IC50 of a neutralizing antibody can be no more than 0.8 μg/ml. The IC50 of a neutralizing antibody can be no more than 0.6 μg/ml. The IC50 of a neutralizing antibody can be no more than 0.4 μg/ml. The IC50 of a neutralizing antibody can be no more than 0.2 μg/ml. The IC50 of a neutralizing antibody can be no more than 0.1 μg/ml. The IC50 of a neutralizing antibody can be no more than 0.08 μg/ml. The IC50 of a neutralizing antibody can be no more than 0.06 pg/ml. The IC50 of a neutralizing antibody can be no more than 0.04 μg/ml. The IC50 of a neutralizing antibody can be no more than 0.02 μg/ml. The IC50 of a neutralizing antibody can be no more than 0.01 μg/ml.

The molecules provided herein having an antigen binding fragment that immunospecifically binds to BTN1A1 or glycosylated BTN1A1 can be anti-BTN1A1 antibodies. Antibodies provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments of any of the above. Non-limiting examples of functional fragments include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (sdFv), Fd fragments, Fv fragments, diabody, triabody, tetrabody and minibody.

In particular, molecules provided herein include immunoglobulin molecules and immunologically active portions of immunoglobulin molecules, e.g., molecules that contain an antigen binding fragment that immunospecifically binds to BTN1A1 or glycosylated BTN1A1. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

The molecules provided herein can be monospecific, bispecific, trispecific antibodies or antibodies of greater multispecificity. Multispecific antibodies may be specific for different epitopes of a BTN1A1 as described here, or can be specific for both a BTN1A1 polypeptide as well as for a heterologous epitope, such as a heterologous polypeptide or solid support material. In specific embodiments, the antibodies provided herein are monospecific for a given epitope of a BTN1A1 polypeptide and do not bind to other epitopes.

5.2.3. Modifications and Derivatives

The binding properties of any of the above molecules having an antigen binding fragment that immunospecifically binds to BTN1A1 or glycosylated BTN1A1 can be further improved by screening for variants that exhibit desired properties. For example, such improvement can be done using various phage display methods known in the art. In phage display methods, functional antibody domains are displayed on the surface of phage particles which carry the polynucleotide sequences encoding them. In a particular embodiment, such phage can be utilized to display antigen binding fragments, such as Fab and Fv or disulfide-bond stabilized Fv, expressed from a repertoire or combinatorial antibody library (e.g., human or murine). Phage expressing an antigen binding fragment that binds the antigen of interest can be selected or identified with antigen, e.g., using labeled antigen or antigen bound or captured to a solid surface or bead. Phage used in these methods are typically filamentous phage, including fd and M13. The antigen binding fragments are expressed as a recombinantly fused protein to either the phage gene III or gene VIII protein. Examples of phage display methods that can be used to make the antibodies or other molecules having an antigen binding fragment as described herein include those disclosed in Brinkman et al., *J. Immunol Methods,* 182:41-50 (1995); Ames et al., *J. Immunol. Methods,* 184:177-186 (1995); Kettleborough et al., *Eur. J. Immunol.,* 24:952-958(1994); Persic et al., *Gene,* 187:9-18 (1997); Burton et al., *Adv. Immunol.* 57:191-280 (1994); PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; all of which are hereby incorporated by references in their entireties.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT Publication WO 92/22324; Mullinax, R. L. et al., *BioTechniques,* 12(6):864-869 (1992); and Sawai et al., *Am. J. Reprod. Immunol.* 34:26-34 (1995); and Better, M. et al. *Science* 240:1041-1043(1988); all of which are hereby incorporated by references in their entireties. Examples of techniques which can be used to produce single-chain Fvs and antibodies include those described in U.S. Pat. Nos. 4,946,778 and 5,258,498; Huston, J. S. et al., *Methods in Enzymology* 203:46-88(1991); Shu, L. et al., *Proc. Natl. Acad. Sci.* (*USA*) 90:7995-7999; and Skerra. A. et al., *Science* 240:1038-1040 (1988); all of which are hereby incorporated by references in their entireties.

Phage display technology can be used to increase the affinity of an anti-BTN1A1 antibody of or anti-glycosylated BTN1A1 antibodies, or other molecules having an antigen binding fragment that immunospecifically binds BTN1A1 or glycosylated BTN1A1 as described herein. This technique can be used in obtaining high affinity antibodies that could be used in the combinatorial methods described herein. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al., *J. Immunol.* 149:3903-3913(1992)). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al., *Proc. Natl. Acad. Sci.* (USA) 95(11):6037-6042(1998); Yelton, D. E. et al., *J. Immunol.* 155:1994-2004 (1995). CDR walking which randomizes the light chain can also be used. (see Schier et al., *J. Mol. Biol.* 263:551-567(1996)).

Random mutagenesis can be used in concert with methods of phage display to identify improved CDRs and/or variable regions. Phage display technology can alternatively be used to increase (or decrease) CDR affinity by directed mutagenesis (e.g., affinity maturation or "CDR-walking"). This technique uses the target antigen or an antigenic fragment thereof to identify antibodies having CDRs that bind with higher (or lower) affinity to the antigen when compared with the initial or parental antibody (see, e.g., Glaser, S. M. et al., *J. Immunol.* 149:3903-3913(1992)).

Methods for accomplishing such affinity maturation are described for example in: Krause, J. C. et al., *MBio.* 2(1) pii: e00345-10. doi: 10.1128/mBio.00345-10(2011); Kuan, C. T. et al., *Int. J. Cancer* 10.1002/ijc.25645; Hackel, B. J. et al., *J. Mol. Biol.* 401(1):84-96(2010); Montgomery, D. L. et al., *MAbs* 1(5):462-474(2009); Gustchina, E. et al., *Virology* 393(1):112-119 (2009); Finlay, W. J. et al., *J. Mol. Biol.* 388(3):541-558 (2009); Bostrom, J. et al., Methods Mol. Biol. 525:353-376 (2009); Steidl, S. et al., *Mol. Immunol.* 46(1):135-144 (2008); and Barderas, R. et al., *Proc. Natl. Acad. Sci.* (*USA*) 105(26):9029-9034 (2008); all of which are hereby incorporated by references in their entireties.

Provided herein are also derivatives of any of the above-described molecules having an antigen binding fragment that immunospecifically binds to BTN1A1 or glycosylated BTN1A1, which can be an anti-BTN1A1 antibody or anti-glycosylated BTN1A1 antibody, but which has one, two, three, four, five or more amino acid substitutions, additions, deletions or modifications relative to a "parental" (or wild-type) molecule. Such amino acid substitutions or additions can introduce naturally occurring (i.e., DNA-encoded) or non-naturally occurring amino acid residues. Such amino acids can be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In some embodiments, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al., *J. Biol. Chem.* 277(30): 26733-26740 (2002); Davies J. et al. *Biotechnology* & *Bioengineering* 74(4): 288-294(2001); all of which are hereby incorporated by references in their entireties). Methods of altering carbohydrate contents are known to those skilled in the art, see, e.g., Wallick, S. C. et al., *J. Exp. Med.* 168(3): 1099-1109(1988); Tao, M. H. et al., *J. Immunol.* 143(8): 2595-2601 (1989); Routledge, E. G. et al., *Transplantation* 60(8):847-53 (1995); Elliott, S. et al., *Nature Biotechnol.* 21:414-21(2003); Shields, R. L. et al., *J. Biol. Chem.* 277(30): 26733-26740 (2002); all of which are hereby incorporated by references in their entireties.

In some embodiments, a humanized antibody is a derivative antibody. Such a humanized antibody includes amino acid residue substitutions, deletions or additions in one or more non-human CDRs. The humanized antibody derivative can have substantially the same binding, better binding, or worse binding when compared to a non-derivative humanized antibody. In some embodiments, one, two, three, four, or five amino acid residues of the CDR have been mutated, such as substituted, deleted or added.

The molecules and antibodies as described herein can be modified by chemical modifications using techniques known to those of skill in the art, including, but not limited to, specific chemical cleavage, acetylation, formulation, metabolic synthesis of tunicamycin, etc. In one embodiment, a derivative molecule or a derivative antibody possesses a similar or identical function as the parental molecule or antibody. In another embodiment, a derivative molecule or a derivative antibody exhibits an altered activity relative to the parent molecule or parental antibody. For example, a derivative antibody (or fragment thereof) can bind to its epitope more tightly or be more resistant to proteolysis than the parental antibody.

Substitutions, additions or deletions in the derivatized antibodies can be in the Fc region of the antibody and can thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821; all of which are hereby incorporated by references in their entireties. In some embodiments, the antibodies or other molecules can have altered affinity for an activating FcγR, e.g., FcγRIIIA Preferably such modifications also have an altered Fc-mediated effector function. Modifications that affect Fc-mediated effector function are well known in the art (see U.S. Pat. No. 6,194,551, and WO 00/42072). In some embodiments, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

ADCC is a cell-mediated reaction in which antigen-nonspecific cytotoxic cells that express FcRs (e.g., natural killer (NK) cells, neutrophils, and macrophages) recognize antibody bound to the surface of a target cell and subsequently cause lysis of (i.e., "kill") the target cell. The primary mediator cells are NK cells. NK cells express FcγRIII only, with FcγRIIIA being an activating receptor and FcγRIIIB an inhibiting one; monocytes express FcγRI, FcγRII and FcγRIII (Ravetch et al. (1991) *Annu. Rev. Immunol.*, 9:457-92). ADCC activity can be expressed as a concentration of antibody or Fc fusion protein at which the lysis of target cells is half-maximal. Accordingly, in some embodiments, the concentration of an antibody or Fc fusion protein of the invention, at which the lysis level is the same as the half-maximal lysis level by the wild-type control, is at least 2-, 3-, 5-, 10-, 20-, 50-, 100-fold lower than the concentration of the wild-type control itself. Additionally, in some embodiments, the antibody or Fc fusion protein of the invention can exhibit a higher maximal target cell lysis as compared to the wild-type control. For example, the maximal target cell lysis of an antibody or Fc fusion protein can be 10%, 15%, 20%, 25% or more higher than that of the wild-type control.

The molecules and antibodies as described herein can be modified to have enhanced potency. In some embodiments, the molecules and antibodies are modified with respect to effector function, e.g., so as to enhance ADCC and/or complement dependent cytotoxicity (CDC). In some embodiments, these therapeutic molecules or antibodies have enhanced interaction with killer cells bearing Fc receptors. Enhancement of effector functions, such as ADCC, can be achieved by various means, including introducing one or more amino acid substitutions in an Fc region. Also, cysteine residue(s) can be introduced in the Fc region, allowing interchain disulfide bond formation in this region. The homodimeric antibody can also have improved internalization capability and/or increased CDC and ADCC. Caron et al., *J. Exp Med.*, 176:1191-95 (1992) and Shopes, B. *J. Immunol.*, 148:2918-22 (1992). Homodimeric antibodies with enhanced anti-cancer activity can also be prepared using heterobifunctional cross-linkers. Wolff et al., *Cancer Research*, 53:2560-65 (1993). Additionally, an antibody or molecule can be engineered which has dual Fc regions and can thereby have enhanced CDC and ADCC capabilities. Stevenson et al., *Anti-Cancer Drug Design* 3:219-30 (1989).

The glycosylation pattern of the Fc region can also be engineered. A number of antibody glycosylation forms have been reported as having a positive impact on effector function, including ADCC. Thus, engineering of the carbohydrate component of the Fc region, particularly reducing core fucosylation, can also have enhanced therapeutic potency. Shinkawa T, et al., *J Biol. Chem.*, 278:3466-73 (2003); Niwa R, et al., *Cancer Res.*, 64:2127-33 (2004); Okazaki A, et al., *J Mol. Biol.* 336:1239^19 (2004); and Shields R L, et al., *J Biol. Chem.* 277:26733-40 (2002). Antibodies or molecules described herein with select glycoforms can be produced by a number of means, including the use of glycosylation pathway inhibitors, mutant cell lines that have absent or reduced activity of particular enzymes in the glycosylation pathway, engineered cells with gene expression in the glycosylation pathway either enhanced or knocked out, and in vitro remodeling with glycosidases and glycosyltransferases. Methods to modify the glycosylation of Fc region and enhance the therapeutic potency of antibodies or other molecules having an antigen binding fragment are known in the art. Rothman et al., Molecular Immunology 26: 1113-1123 (1989); Umana et al., *Nature Biotechnology* 17: 176-180 (1999); Shields et al., JBC 277:26733-26740 (2002); Shinkawa et al., *JBC* 278: 3466-3473 (2003); Bischoff et al., *J. Biol. Chem.* 265(26):15599-15605 (1990); U.S. Pat. Nos. 6,861,242 and 7,138,262, as well as US Publication No. 2003/0124652; all of which are hereby incorporated by reference in their entireties. A person of ordinary skill in the art would understand that the antibodies and molecules provided herein can be modified by any methods known in the art to have enhanced therapeutic potency.

Derivative molecules or antibodies can also have altered half-lives (e.g., serum half-lives) of parental molecules or antibodies in a mammal, preferably a human. In some embodiments, such alteration results in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of humanized antibodies or other molecules in a mammal, preferably a human, results in a higher serum titer of said antibodies or other molecules in the mammal, and thus, reduces the frequency of the administration of said antibodies or other molecules and/or reduces the concentration of said antibodies or other molecules to be administered. Molecules or antibodies having increased in vivo half-lives can be generated by techniques known to those of skill in the art. For example, molecules or antibodies with increased in vivo half-lives can be generated by modifying (e.g., substituting, deleting or adding) amino acid residues identified as involved in the interaction between the Fc domain and the FcRn receptor. The humanized antibodies as described herein can be engineered to increase biological half-lives (see, e.g. U.S. Pat. No. 6,277,375). For example, humanized antibodies as described herein can be engineered in the Fc-hinge domain to have increased in vivo or serum half-lives.

Molecules or antibodies as described herein with increased in vivo half-lives can be generated by attaching to said antibodies or antibody fragments polymer molecules such as high molecular weight polyethyleneglycol (PEG). PEG can be attached to the molecules or antibodies with or without a multifunctional linker either through site-specific conjugation of the PEG to the N- or C-terminus of said molecules or antibodies or via epsilon-amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The molecules or antibodies as described herein can also be modified by the methods and coupling agents described by Davis et al. (See U.S. Pat. No. 4,179,337) in order to provide compositions that can be injected into the mammalian circulatory system with substantially no immunogenic response. Removal of the Fc portion can reduce the likelihood that the antibody fragment elicits an undesirable immunological response and, thus, antibodies without Fc can be used for prophylactic or therapeutic treatments. As described above, antibodies can also be constructed so as to be chimeric, partially or fully human, so as to reduce or eliminate the adverse immunological consequences resulting from administering to an animal an antibody that has been produced in, or has sequences from, other species.

5.2.3. Fusions and Conjugates

Provided herein are molecules having an antigen binding fragment that immunospecifically binds to BTN1A1 or glycosylated BTN1A1, including anti-BTN1A1 antibodies and anti-glycosylated BTN1A1 antibodies. In some embodiments, such molecules are expressed as a fusion protein with other proteins or chemically conjugated to another moiety.

In some embodiments, the molecule is a fusion protein having an Fc portion, wherein the Fc portion can be varied by isotype or subclass, can be a chimeric or hybrid, and/or can be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al., Mol. Immun. 34(6):441-452 (1997), Swann, P. G., Curr. Opin. Immun. 20:493-499 (2008), and Presta, L. G., Curr. Opin. Immun. 20:460-470 (2008). In some embodiments the Fc region is the native IgG1, IgG2, or IgG4 Fc region. In some embodiments the Fc region is a hybrid, for example a chimeric having of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region can include the entire hinge region, or less than the entire hinge region.

Another embodiment includes IgG2-4 hybrids and IgG4 mutants that have reduce binding to FcR which increase their half-life. Representative IG2-4 hybrids and IgG4 mutants are described in Angal et al., Molec. Immunol. 30(1):105-108 (1993); Mueller et al., Mol. Immun. 34(6): 441-452 (1997); and U.S. Pat. No. 6,982,323; all of which are hereby incorporated by references in their entireties. In some embodiments the IgG1 and/or IgG2 domain is deleted for example, Angal et al. describe IgG1 and IgG2 having serine 241 replaced with a proline.

In some embodiments, the molecules are polypeptides having at least 10, at least 20, at least 30, at least 40, at least 50, at least 60, at least 70, at least 80, at least 90 or at least 100 amino acids.

In some embodiments, provided herein are molecules that have an antigen binding fragment that immunospecifically binds to BTN1A1 or glycosylated BTN1A1, which link to or covalently bind or form into a complex with at least one moiety. Such a moiety can be, but is not limited to, one that increases the efficacy of molecules as diagnostic or therapeutic agents. In some embodiments, the moiety can be image agents, toxins, therapeutic enzymes, antibiotics, radio-labeled nucleotides and the like.

Molecules provided herein can include a therapeutic moiety (or one or more therapeutic moieties). Molecules provided herein can be an antibody conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, auristatin F, monomethyl auristatin E, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458, 935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, molecules provided herein be antibodies conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, y-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

In addition, an antibody provided herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7, 10-tetraazacyclododecane-N,N',N'',N'''-tetraacetic acid (DOTA) which can be attached to the antibody via a linker molecule. Such linker molecules are commonly known in the art and described in Denardo et al., 1998, *Clin Cancer Res.* 4(10):2483-90; Peterson et al., 1999, *Bioconjug. Chem.* 10(4):553-7; and Zimmerman et al., 1999, *Nucl. Med. Biol.* 26(8):943-50, each incorporated by reference in their entireties.

The therapeutic moiety or drug conjugated or recombinantly fused to an antibody provided herein that immunospecifically binds to BTN1A1 should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody provided herein: the nature of the disease, the severity of the disease, and the condition of the subject.

In some embodiments, the moiety can be enzymes, hormones, cell surface receptors, toxins (such as abrin, ricin A, *pseudomonas* exotoxin (i.e., PE-40), diphtheria toxin, ricin, gelonin, or pokeweed antiviral protein), proteins (such as tumor necrosis factor, interferon (e.g., α-interferon, (3-interferon), nerve growth factor, platelet derived growth factor, tissue plasminogen activator, or an apoptotic agent (e.g., tumor necrosis factor-α, tumor necrosis factor-(3)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, monomethyl auristatin F (MMAF), monomethyl auristatin E (MMAE; e.g., vedotin) and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

Techniques for conjugating such therapeutic moieties to antibodies are well known; see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; Thorpe et al., *Immunol. Rev.* 62:119-158 (1982); Carter et al., *Cancer J.* 14(3):154-169 (2008); Alley et al., *Curr. Opin. Chem. Biol.* 14(4):529-537 (2010); Carter et al., *Amer. Assoc. Cancer Res. Educ. Book.* 2005(1):147-154 (2005); Carter et al., *Cancer J.* 14(3):154-169(2008); Chari, *Acc. Chem Res.* 41(1):98-107 (2008); Doronina et al., Nat. Biotechnol. 21(7):778-784(2003); Ducry et al., *Bioconjug Chem.* 21(1):5-13(2010); Senter, *Curr. Opin. Chem. Biol.* 13(3):235-244 (2009); and Teicher, *Curr Cancer Drug Targets.* 9(8):982-1004 (2009).

In some embodiments, molecules as described herein can be conjugated to a marker, such as a peptide, to facilitate purification. In some embodiments, the marker is a hexahistidine peptide (SEQ ID NO: 55), the hemagglutinin "HA" tag, which corresponds to an epitope derived from the influenza hemagglutinin protein (Wilson, I. A. et al., *Cell,* 37:767-778 (1984)), or the "flag" tag (Knappik, A. et al., *Biotechniques* 17(4):754-761 (1994)).

In some embodiments, the moiety can be an image agent that can be detected in an assay. Such image agent can be enzymes, prosthetic groups, radiolabels, nonradioactive paramagnetic metal ions, haptens, fluorescent labels, phosphorescent molecules, chemiluminescent molecules, chromophores, luminescent molecules, bioluminescent molecules, photoaffinity molecules, colored particles or ligands, such as biotin.

In some embodiments, the enzymes include, but not limited to, horseradish peroxidase, alkaline phosphatase, beta-galactosidase, or acetylcholinesterase; the prosthetic group complexes include, but not limited to, streptavidin/ biotin and avidin/biotin; the fluorescent materials include, but not limited to, umbelliferone, fluorescein, fluorescein isothiocyanate, rhodamine, dichlorotriazinylamine fluorescein, dansyl chloride or phycoerythrin; the luminescent material such as, but not limited to, luminol; the bioluminescent materials include, but not limited to, luciferase, luciferin, and aequorin; the radioactive material include, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb) yttrium ($^{90}$Y), zinc ($^{65}$Zn); positron emitting metals using various positron emission tomographies, and nonradioactive paramagnetic metal ions.

The image agent can be conjugated to the molecule having an antigen binding fragment either directly, or indirectly through an intermediate (such as, for example, a linker known in the art) using techniques known in the art. See, for example, U.S. Pat. No. 4,741,900 for metal ions which can be conjugated to antibodies and other molecules as described herein for use as diagnostics. Some conjugation methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Monoclonal antibodies can also be reacted with an enzyme in the presence of a coupling agent such as glutaraldehyde or periodate. Conjugates with fluorescein markers can be prepared in the presence of these coupling agents or by reaction with an isothiocyanate.

The molecules as described herein can be conjugated to a second antibody to form an antibody heteroconjugate as described by Segal in U.S. Pat. No. 4,676,980. Such heteroconjugate antibodies can additionally bind to haptens (e.g., fluorescein), or to cellular markers (e.g., 4-1-BB, B7-H4, CD4, CD8, CD14, CD25, CD27, CD40, CD68, CD163, CTLA4, GITR, LAG-3, OX40, TIM3, TIM4, TLR2, LIGHT, ICOS, B7-H3, B7-H7, B7-H7CR, CD70, CD47) or to cytokines (e.g., IL-7, IL-15, IL-12, IL-4 TGF-beta, IL-10, IL-17, IFNγ, Flt3, BLys) or chemokines (e.g., CCL21).

The molecules as described herein can be attached to solid supports, which can be useful for immunoassays or purification of the target antigen or of other molecules that are capable of binding to target antigen that has been immobilized to the support via binding to an antibody or antigen binding fragment as described herein. Such solid supports include, but are not limited to, glass, cellulose, polyacrylamide, nylon, polystyrene, polyvinyl chloride or polypropylene.

Provided herein are also nucleic acid molecules (DNA or RNA) that encode any such antibodies, antigen binding fragments, and molecules having the antigen binding fragment that immunospecifically binds to BTN1A1 or glycosylated BTN1A1. Provided herein are also vector molecules (such as plasmids) that are capable of transmitting or of replication such nucleic acid molecules. The nucleic acids can be single-stranded, double-stranded, and can contain both single-stranded and double-stranded portions.

Antibody-Drug Conjugates (ADCs)

As the molecules provided herein can result in internalization of BTN1A1 into the cells. Provided herein are also Antibody-Drug Conjugates (ADCs) that include any anti-BTN1A1 antibody described herein. In a specific embodiment, provided herein are ADC that having STC810 or a humanized variant thereof as the antibody.

In some embodiments, provided herein are antibody-drug conjugates, including an antibody-drug conjugate of the following formulas (Ia) and (Ib):

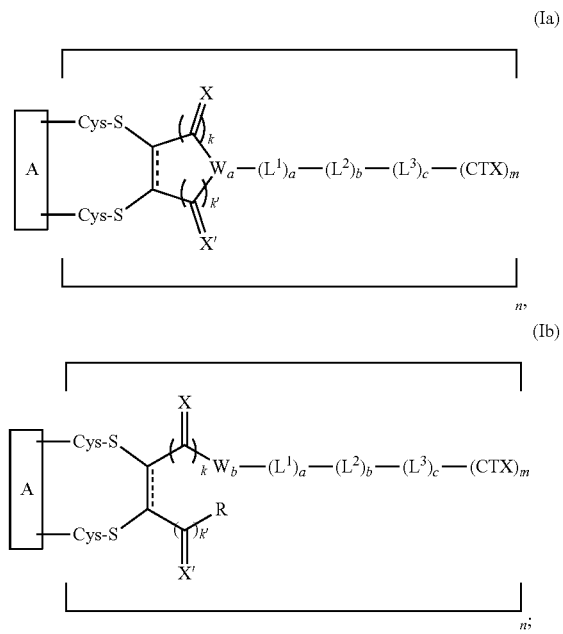

or a pharmaceutically acceptable salt thereof;
wherein:
A is a molecule that have an antigen binding fragment;
the two depicted cysteine residues are from an opened cysteine-cysteine disulfide bond in A;
each X and X' is independently O, S, NH, or NR$^1$ wherein R$^1$ is C$_{1-6}$ alkyl;
W$_a$ is =N—, =CH—, =CHCH$_2$—, =C(R$^2$)—, or =CHCH(R$^2$)—; W$_b$ —NH—, —N(R$^1$)—, —CH$_2$—, —CH$_2$—NH—, —CH$_2$—N(R$^1$)—, —CH$_2$CH$_2$—, —CH(R$^2$)—, or —CH$_2$CH(R$^2$)—; wherein R$^1$ and R$^2$ are independently C$_{1-6}$ alkyl;
CTX is a cytotoxin;
R is any chemical group; or R is absent;
each L$^1$, L$^2$ and L$^3$ is independently a linker selected from the group consisting of —O—, —C(O)—, —S—, —S(O)—, —S(O)$_2$—, —NH—, —NCH$_3$—, —(CH$_2$)$_q$—, —NH(CH$_2$)$_2$NH—, —OC(O)—, —CO$_2$—, —NHCH$_2$CH$_2$C(O)—, —C(O) NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)$_p$, —(CH$_2$CH$_2$O)$_p$CH$_2$CH$_2$—, —CH$_2$CH$_2$—(CH$_2$CH$_2$O)$_p$—, —OCH(CH$_2$O—)$_2$, -(AA)$_r$-, cyclopentanyl, cyclohexanyl, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$ alkyl, —C(O)CH$_3$, —CN, —NH—, —NH$_2$, —O—, —OH, —NHCH$_3$, —N(CH$_3$)$_2$, and C$_{1-3}$ alkyl;

a, b and c are each independently an integer of 0, 1, 2 or 3, provided that at least one of a, b or c is 1;
each k and k' is independently an integer of 0 or 1;
each p is independently an integer of 1 to 14;
each q is independently an integer from 1 to 12;
each AA is independently an amino acid;
each r is 1 to 12;
m is an integer of 1 to 4;
n is an integer of 1 to 4; and
the ===== bond represents a single or a double bond.

In certain embodiments of the antibody-drug conjugate (ADC) of formula (Ib), R is selected from the group consisting of W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, and W-$(L^1)_a$-$(L^2)_b$-$(L^3)_c$-Z, as defined herein. In certain embodiments, R is selected from the group consisting of W, $(L^1)_a$, $(L^2)_b$, $(L^3)_c$, and W-$(L^1)_a$-$(L^2)_b$-$(L^3)_c$. In certain embodiments, R is selected from the group consisting of Z, $(L^1)_a$-$(L^2)_b$-$(L^3)_c$-Z, and W-$(L^1)_a$-$(L^2)_b$-$(L^3)_c$-Z.

In certain embodiments of the antibody-drug conjugate (ADC) of formula (Ib), R is a detectable probe. In certain embodiments, R is a fluorophore, chromophore, radiolabel, enzyme, ligand, antibody or antibody fragment. In certain embodiments, R is a ligand (e.g., a ligand specific for a receptor on a tumor cell, such as a prostate specific membrane antigen, or a virally infected cell, such as an HIV infected cell).

In certain embodiments of the antibody-drug conjugate (ADC) of formula (Ib), R is bonded to the rest of the linker molecule via an amide, an N—($C_{1-6}$ alkyl)amide, a carbamate, an N—($C_{1-6}$ alkyl)carbamate, an amine, an N—($C_{1-6}$ alkyl)amine, an ether, a thioether, an urea, an N—($C_{1-6}$ alkyl)urea, or an N,N-di($C_{1-6}$ alkyl)urea bond.

In certain embodiments of the antibody-drug conjugate (ADC) of formula (Ia) or (Ib), each $L^1$, $L^2$ and $L^3$ is independently selected from the group consisting of —NHC(O)—, —C(O)NH—, —($CH_2CH_2O)_p$—, —($CH_2CH_2O)_pCH_2CH_2$—, —$CH_2CH_2$—($CH_2CH_2O)_p$—, —OCH($CH_2O$—$)_2$, -(AA)$_r$-, unsubstituted phenylenyl, and phenylenyl substituted by 1 or 2 substituents selected from the group consisting of halo, $CF_3$—, $CF_3O$—, $CH_3O$—, —C(O)OH, —C(O)O$C_{1-3}$ alkyl, —C(O)$CH_3$, —CN, —NH—, —$NH_2$, —O—, —OH, —$NHCH_3$, —N($CH_3)_2$, and $C_{1-3}$ alkyl; where a, b and c are each independently 0 or 1; and each p and r is independently 1, 2 or 3. In certain embodiments, one or more of the $L^1$, $L^2$ and $L^3$ is -(AA)$_r$-, wherein -(AA)$_r$- is ValCit (e.g., the first amino acid is Valine, the second amino acid is Citrulline, and r is 1). In certain embodiments, one or more of the $L^1$, $L^2$ and $L^3$ is -(AA)$_r$-, wherein -(AA)$_r$- is ValAla (e.g., the first amino acid is Valine, the second amino acid is Alanine, and r is 1). In certain embodiments, one or more of the $L^1$, $L^2$ and $L^3$ is phenylenyl substituted by —C(O)OH and —$NH_2$. In certain embodiments, one or more of the $L^1$, $L^2$ and $L^3$ is phenylenyl substituted by —C(O)O— and —NH—. In certain embodiments, one or more of the $L^1$, $L^2$ and $L^3$ is phenylenyl substituted by —OC(O)— and —NH—. In certain embodiments, one or more of the $L^1$, $L^2$ and $L^3$ is phenylenyl substituted by —O— and —NH—. In certain embodiments, one or more of the $L^1$, $L^2$ and $L^3$ is para aminobenzyl (PAB), which is optionally substituted with —C(O)O—, —OC(O)— or —O—. In certain embodiments, $L^1$ is —($CH_2)_q$—, $L^2$ is absent, $L^3$ is absent, and the CTX is bonded to $(L^1)_a$-$(L^2)_b$-$(L^3)_c$ via an amide bond. In certain embodiments, $L^1$ is —($CH_2)_q$—, $L^2$ is —($OCH_2CH_2)_p$—, $L^3$ is absent, and the CTX is bonded to $(L^1)_a$-$(L^2)_b$-$(L^3)_c$ via an amide bond. In certain embodiments, $L^1$ is —($CH_2CH_2O)_p$—, $L^2$ is —($CH_2)_q$—, $L^3$ is absent, and the CTX is bonded to $(L^1)_a$-$(L^2)_b$-$(L^3)_c$ via an amide bond. In certain embodiments, each $L^1$ is independently selected from the group consisting of —($CH_2CH_2O)_pCH_2CH_2$— and —$CH_2CH_2$—($CH_2CH_2O)_p$—, $L^2$ is absent, $L^3$ is absent, and the CTX is bonded to $(L^1)_a$-$(L^2)_b$-$(L^3)_c$ via an amide bond. In certain embodiments, each $L^1$ is independently selected from the group consisting of —($CH_2)_q$—, —($CH_2CH_2O)_p$, —($CH_2CH_2O)_pCH_2CH_2$—, —$CH_2CH_2$—($CH_2CH_2O)_p$—, and —C(O)—, $L^2$ is Val-Cit, $L^3$ is PAB, and the CTX is bonded to $(L^1)_a$-$(L^2)_b$-$(L^3)_c$ via an amide bond. In certain embodiments, each $L^1$ is independently selected from the group consisting of —($CH_2)_q$—, —($CH_2CH_2O)_p$, —($CH_2CH_2O)_pCH_2CH_2$—, —$CH_2CH_2$—($CH_2CH_2O)_p$—, and —C(O)—, $L^2$ is Val-Cit, $L^3$ is PAB, and the CTX is bonded to $(L^1)_a$-$(L^2)_b$-$(L^3)_c$ via an amide bond. In certain embodiments, each $L^1$ is independently selected from the group consisting of —($CH_2)_q$—, —($CH_2CH_2O)_p$, —($CH_2CH_2O)_pCH_2CH_2$—, —$CH_2CH_2$—($CH_2CH_2O)_p$—, and —C(O)—, $L^2$ is Val-Ala, $L^3$ is PAB, and the CTX is bonded to $(L^1)_a$-$(L^2)_b$-$(L^3)_c$ via an amide bond.

In certain embodiments of the antibody-drug conjugate (ADC) of formula (Ia) or (Ib), CTX is selected from a from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments of the antibody-drug conjugate (ADC) of formula (Ia) or (Ib), the CTX is a chemotherapeutic agent. Those of ordinary skill in the art will be aware of appropriate chemotherapeutic agents as disclosed, for example, in Chu, E., DeVite, V. T., 2012, Physicians' Cancer Chemotherapy Drug Manual 2012 (Jones & Bartlett Learning Oncology), and similar documents.

In certain embodiments, the CTX may be any FDA-approved chemotherapeutic agent. In certain embodiments, the CTX may be any FDA-approved chemotherapeutic agent available for cancer treatment.

In certain embodiments, the CTX is selected from the group consisting of an alkylating agents, an anthracyclines, a cytoskeletal disruptors (taxanes), an epothilones, an histone deacetylase Inhibitor (HDAC), an inhibitor of Topoisomerase I, an Inhibitor of Topoisomerase II, a kinase inhibitor, a monoclonal antibodies, a nucleotide analog, a peptide antibiotic, a platinum-based agent, a retinoids, a Vinca alkaloid or a derivative thereof, and radioisotope.

In certain embodiments, the CTX is selected from the group consisting of Actinomycin, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In certain embodiments, the CTX is selected from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments, the CTX is selected from the group consisting of Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. In certain embodiments, the CTX is an auristatin, a calicheamicin, a maytansinoid, or a tubulysin.

In certain embodiments, the CTX is monomethylauristatin E (MMAE), monomethylauristatin F (MMAF), a pyrrolobenzodiazepine (PDB), calicheamicin γ, mertansine, or tubulysin T2. In certain embodiments, the CTX is MMAE or MMAF. In certain embodiments, the CTX is a PDB. In certain embodiments, the CTX is tubulysin T2. In certain embodiments, the CTX is tubulysin T3, or tubulysin T4, the structures for which are provided below:

T3

T4

Thus, the conjugated or fusion proteins provided herein can include any anti-BTN1A1 antibody or antigen binding fragments described herein. In one embodiment, a conjugated or fusion protein provided herein comprises the VH or VL domain of the murine monoclonal antibody STC810, as depicted in Table 2. In one embodiment, a conjugated or fusion protein provided herein comprises both the VH and VL domain of the murine monoclonal antibody STC810, as depicted in Table 2. In another embodiment, a conjugated or fusion protein provided herein comprises one or more VH CDRs having the amino acid sequence of any one of the VH CDRs of the murine monoclonal antibody STC810, as depicted in Table 2. In another embodiment, a conjugated or fusion protein comprises one or more VL CDRs having the amino acid sequence of any one of the VL CDRs of the murine monoclonal antibody STC810, as depicted in Table 2. In yet another embodiment, a conjugated or fusion protein provided herein comprises at least one VH CDR and at least one VL CDR of the murine monoclonal antibody STC810, as depicted in Table 2.

In some embodiments, a conjugated or fusion protein provided can include an antigen binding fragment that competitively blocks (e.g., in a dose-dependent manner) a BTN1A1 epitope described herein. The BTN1A1 epitope can be an epitope of STC810 as described herein. In some embodiments, a conjugated or fusion protein provided can include an antigen binding fragment that immunospecifically binds to an epitope of BTN1A1 as described herein. The BTN1A1 epitope can be an epitope of STC810 as described herein. In some embodiments, the BTN1A1 epitope has at least five consecutive amino acids of an amino acid sequence of SEQ ID NOS: 31-41.

5.3 Compositions

Provided herein are also compositions having molecules that have an antigen binding fragment that immunospecifically binds to BTN1A1 (including glycosylated BTN1A1). In some embodiments, the compositions have anti-BTN1A1 antibodies (including anti-glycosylated BTN1A1 antibodies). In some aspects, the antigen binding fragment immunospecifically binds to BTN1A1 glycosylated at positions N55, N215, and/or N449. In some aspects, the antigen binding fragment immunospecifically binds to BTN1A1 glycosylated at position N55. In some aspects, the antigen binding fragment immunospecifically binds to BTN1A1 glycosylated at position N215. In some aspects, the antigen binding fragment immunospecifically binds to BTN1A1 glycosylated at position N449. In some aspects, the antigen binding fragment immunospecifically binds to one or more glycosylation motifs. In some aspects, the antigen binding fragment immunospecifically binds to BTN1A1 glycosylated at positions N55 and N215. In some aspects, the antigen binding fragments immunospecifically binds to BTN1A1 glycosylated at positions N215 and N449. In some aspects, the antigen binding fragments immunospecifically binds to BTN1A1 glycosylated at positions N55 and N449. In some aspects, the antigen binding fragments immunospecifically binds to BTN1A1 glycosylated at positions N55, N215 and N449.

In some embodiments, provided herein are compositions having molecules that have an antigen binding fragment that immunospecifically binds to BTN1A1, wherein the antigen binding fragment preferentially binds to glycosylated BTN1A1 over non-glycosylated BTN1A1. In some aspects, the antigen binding fragments preferentially bind to BTN1A1 glycosylated at positions N55, N215, and/or N449 over non-glycosylated BTN1A1. In some aspects, the antigen binding fragments preferentially bind to BTN1A1 glycosylated at position N55 over non-glycosylated BTN1A1. In some aspects, the antigen binding fragments preferentially bind to BTN1A1 glycosylated at position N215 over non-glycosylated BTN1A1. In some aspects, the antigen binding fragments preferentially bind to BTN1A1 glycosylated at position N449 over non-glycosylated BTN1A1. In some aspects, the antigen binding fragments preferentially bind to one or more glycosylation motifs. In some aspects, the antigen binding fragments preferentially binds to BTN1A1 glycosylated at positions N55 and N215 over non-glycosylated BTN1A1. In some aspects, the antigen binding fragments preferentially bind to BTN1A1 glycosylated at positions N215 and N449 over non-glycosylated BTN1A1. In some aspects, the antigen binding fragments preferentially bind to BTN1A1 glycosylated at positions N55 and N449 over non-glycosylated BTN1A1. In some aspects, the antigen binding fragments preferentially binds to BTN1A1 glycosylated at positions N55, N215 and N449 over non-glycosylated BTN1A1.

In some embodiments, the antigen binding fragment binds to glycosylated BTN1A1 with Kd less than half of the Kd exhibited relative to unglycosylated BTN1A1. In some embodiments, the antigen binding fragment binds to glycosylated BTN1A1 with Kd at least 10 times less than the Kd exhibited relative to unglycosylated BTN1A1.

In some embodiments, the antigen binding fragment binds to glycosylated BTN1A1 with an MFI that is at least twice as high as the MFI as exhibited relative to unglycosylated BTN1A1. In some embodiments, the antigen binding fragment binds to glycosylated BTN1A1 with an MFI that is at least five times as high as the MFI as exhibited relative to unglycosylated BTN1A1.

In some aspects, provided herein are compositions having molecules that have an antigen binding fragment that immunospecifically masks BTN1A1 glycosylation at positions N55, N215, and/or N449. In some aspects, the antigen binding fragments immunospecifically mask BTN1A1 glycosylation at position N55. In some aspects, the antigen binding fragments immunospecifically mask BTN1A1 glycosylation at position N215. In some aspects, the antigen binding fragments immunospecifically mask BTN1A1 glycosylation at position N449. In some aspects, the antigen binding fragments immunospecifically mask one or more glycosylation motifs of BTN1A1. In some aspects, the antigen binding fragments immunospecifically mask BTN1A1 glycosylation at positions N55 and N215. In some aspects, the antigen binding fragments immunospecifically mask BTN1A1 glycosylation at positions N215 and N449. In some aspects, the antigen binding fragments immunospecifically mask BTN1A1 glycosylation at positions N55 and N449. In some aspects, the antigen binding fragments immunospecifically mask BTN1A1 glycosylation at positions N55, N215 and N449.

In some embodiments, the compositions can have a molecule having antigen binding fragment that comprises the VH or VL domain of the murine monoclonal antibody STC810, as depicted in Table 2. In one embodiment, the compositions can have a molecule having antigen binding fragment that comprises both the VH and VL domain of the murine monoclonal antibody STC810, as depicted in Table 2. In another embodiment, the compositions can have a molecule having antigen binding fragment that comprises one or more VH CDRs having the amino acid sequence of any one of the VH CDRs of the murine monoclonal antibody STC810, as depicted in Table 2. In another embodiment, the compositions can have a molecule having antigen binding fragment that comprises one or more VL CDRs having the amino acid sequence of any one of the VL CDRs of the murine monoclonal antibody STC810, as depicted in Table 2. In yet another embodiment, the compositions can have a molecule having antigen binding fragment that comprises at least one VH CDR and at least one VL CDR of the murine monoclonal antibody STC810, as depicted in Table 2.

In some embodiments, the compositions can have a molecule having antigen binding fragment that competitively blocks (e.g., in a dose-dependent manner) a BTN1A1 epitope described herein. The BTN1A1 epitope can be an epitope of STC810 as described herein. In some embodiments, the compositions can have a molecule having antigen binding fragment that immunospecifically binds to an epitope of BTN1A1 as described herein. The BTN1A1 epitope can be an epitope of STC810 as described herein. In some embodiments, the BTN1A1 epitope has at least five consecutive amino acids of an amino acid sequence of SEQ ID NOS: 31-41.

In some embodiments, the composition can have at least 0.1% by weight the antibodies or other molecules as described herein. In some embodiments, the composition can have at least 0.5%, 1%, 2%, 3%, 4%, 5%, 6%, 7% 8%, 9%, 10%, 15%, 20%, 25%, 30%, 35%, 40%, 45%, 50%, 55%, 60%, 65%, 70%, 75%, 80%, 85%, 90%, or more by weight of the anti-BTN1A1 antibodies or other molecules having an antigen binding fragment that immunospecifically binds to BTN1A1. In other embodiments, for example, the anti-BTN1A1 antibodies or other molecules having an antigen binding fragment that immunospecifically binds to BTN1A1 can constitute between about 2% to about 75% of the weight of the composition, between about 25% to about 60%, between about 30% to about 50%, or any range therein.

The composition can be a pharmaceutical composition having anti-BTN1A1 antibodies or other molecules having an antigen binding fragment that immunospecifically binds to BTN1A1 as the active ingredient as well as a pharmaceutically acceptable carrier. The pharmaceutical composition can further include one or more additional active ingredient. A pharmaceutically acceptable carrier can be a carrier approved by a regulatory agency of the Federal or a state government, or listed in the U.S. Pharmacopeia, European Pharmacopeia or other generally recognized Pharmacopeia for use in animals, and more particularly in humans.

The preparation of a pharmaceutical composition having the antibodies or other molecules as described herein as active ingredient are known to those of skill in the art in light of the present disclosure, as exemplified by Remington's Pharmaceutical Sciences, 18th Ed., 1990, incorporated herein by reference. Moreover, for animal (including human) administration, it is understood that preparations should meet sterility, pyrogenicity, general safety, and purity standards as required by FDA Office of Biological Standards.

The pharmaceutically acceptable carriers include liquid, semi-solid, i.e., pastes, or solid carriers. Examples of carriers or diluents include fats, oils, water, saline solutions, lipids, liposomes, resins, binders, fillers, and the like, or combinations thereof. The pharmaceutically acceptable carrier can include aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings (e.g., lecithin), surfactants, antioxidants, preservatives (e.g., antibacterial or antifungal agents, anti-oxidants, chelating agents, inert gases, parabens (e.g., methylparabens, propylparabens), chlorobutanol, phenol, sorbic acid, thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc), gels, binders, excipients, disintegration agents, lubricants, sweetening agents, flavoring agents, dyes, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in administrable composition for use in practicing the methods is appropriate. The pH and exact concentration of the various components in a pharmaceutical composition are adjusted according to well-known parameters. In accordance with certain aspects of the present disclosure, the composition can be combined with the carrier in any convenient and practical manner, i.e., by solution, suspension, emulsification, admixture, encapsulation, absorption, grinding, and the like. Such procedures are routine for those skilled in the art.

In some embodiments, a pharmaceutically acceptable carrier can be an aqueous pH buffered solution. Examples include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

In some embodiments, pharmaceutically acceptable carriers can be sterile liquids, such as water and oils, including those of petroleum, animal, vegetable or synthetic origin, such as peanut oil, soybean oil, mineral oil, sesame oil and the like. Water can be a carrier, particularly when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, polysorbate-80 and the like. The composition can also contain minor amounts of wetting or emulsifying agents, or pH buffering agents. These compositions can take the form of solutions, suspensions, emulsion, tablets, pills, capsules, powders, sustained-release formulations and the like.

Certain embodiments of the present disclosure can have different types of carriers depending on whether it is to be administered in solid, liquid, or aerosol form, and whether it needs to be sterile for the route of administration, such as injection. The compositions can be formulated for administration intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference). Typically, such compositions can be prepared as either liquid solutions or suspensions; solid forms suitable for use to prepare solutions or suspensions upon the addition of a liquid prior to injection can also be prepared; and, the preparations can also be emulsified.

The anti-BTN1A1 antibodies or other molecules having an antigen binding fragment that immunospecifically binds to BTN1A1 can be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, 2-ethylamino ethanol, histidine, or procaine.

In further embodiments, provided herein are pharmaceutical compositions having a lipid. A lipid can broadly include a class of substances that are characteristically insoluble in water and extractable with an organic solvent. Examples include compounds that contain long-chain aliphatic hydrocarbons and their derivatives. A lipid can be naturally occurring or synthetic (i.e., designed or produced by man). A lipid can be a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Compounds other than those specifically described herein that are understood by one of skill in the art as lipids can also be used.

One of ordinary skill in the art would be familiar with the range of techniques that can be employed for dispersing a composition in a lipid vehicle. For example, antibodies can be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of active ingredient in each therapeutically useful composition can be prepared in such a way that a suitable dosage will be obtained in any given unit dose of the compound. Factors, such as solubility, bioavailability, biological half-life, route of administration, product shelf life, as well as other pharmacological considerations, can be contemplated by one skilled in the art of preparing such pharmaceutical formulations, and as such, a variety of dosages and treatment regimens may be desirable.

A unit dose or dosage refers to physically discrete units suitable for use in a subject, each unit containing a predetermined quantity of the pharmaceutical composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose can have from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/ body weight, about 100 milligram/kg/body weight, about 200 milligram/kg/body weight, about 350 milligram/kg/ body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/ kg/body weight, about 5 microgram/kg/body weight to about 500 milligram/kg/body weight, etc., can be administered, based on the numbers described above. The practitioner responsible for administration will, in any event, determine the concentration of active ingredient(s) in a composition and appropriate dose(s) for the individual subject.

As a person of ordinary skill in the art would understand, the compositions described herein are not limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy varies according to the type of use and mode of administration, as well as the particularized requirements of individual subjects. The actual dosage amount of a composition administered to an animal patient, including a human patient, can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount can vary according to the response of the subject. The practitioner responsible for administration will, in any event, determine the concentration of active ingredient(s) in a composition and appropriate dose(s) for the individual subject.

5.4 Therapeutic Uses and Methods of Treatments

BTN1A1 is specifically and highly expressed in cancer cells. In some embodiments, provided herein are therapeutic uses of molecules having an antigen binding fragment that immunospecifically binds to BTN1A1 or glycosylated BTN1A1 in cancer treatments. In some embodiments, these molecules bind to BTN1A1-expressing cancer cells and induce an immune response resulting in destruction these cancer cells. The molecules provided herein, including anti-BTN1A1 antibodies (e.g. STC810 or its humanized variant) can enhance T-cell dependent apoptisis of cancer cells, inhibit proliferation of cancer cells.

The molecules provided herein having an antigen binding fragment that immunospecifically binds to BTN1A1, including anti-BTN1A1 antibodies (e.g. STC810 or its humanized variant) can cause the internalization of BTN1A1 into lysosomes. Thus, also provided herein are methods of using molecules provided herein to deliver a compound to a cell expressing BTN1A1 by contacting the cell with molecules provided herein conjugated with the compound. The compound can be an imaging agent, a therapeutic agent, a toxin or a radionuclide as described herein. The compound can be conjugated with anti-BTN1A1 antibody. The conjugate can be any conjugate as described herein, such as an ADC. The cell can be a cancer cell. The cell can also be a population of cells that include both cancer cells and normal cells. Because cancer cells specifically and highly express BTN1A1, the molecules described herein can be used to achieve specific drug delivery to cancer cells but not normal cells.

The molecules provided herein having an antigen binding fragment that immunospecifically binds to BTN1A1, including anti-BTN1A1 antibodies (e.g. STC810 or its humanized variant) can modulating an immune response in a subject. The molecules provided herein can promote T cell activation. The molecules provided herein can promote T cell proliferation. The molecules provided herein can increase cytokine production. The molecules provided herein can also enhance T-cell dependent apoptosis of a cell expressing BTN1A1 or inhibit the proliferation of cells expressing BTN1A1.

Accordingly, provided herein are methods of modulating an immune response in a subject by administering an effective amount of the molecules described herein that have an antigen binding fragment that immunospecifically binds to BTN1A1, including anti-BTN1A1 antibodies (e.g. STC810 or its humanized variant). Modulating an immune response can include (a) increasing T cell activation; (b) increasing T cell proliferation; and/or (c) increasing cytokine production.

Also provided herein are methods of enhancing T-cell dependent apoptosis of a cell expressing BTN1A1 by contacting the cell with an effective amount of molecules described herein that have an antigen binding fragment that immunospecifically binds to BTN1A1, including anti-BTN1A1 antibodies (e.g. STC810 or its humanized variant). Provided herein are also methods of inhibiting the proliferation of cells expressing BTN1A1 by contacting the cell with an effective amount of molecules described herein that have an antigen binding fragment that immunospecifically binds to BTN1A1, including anti-BTN1A1 antibodies (e.g. STC810 or its humanized variant). The cells can be cancer cells.

In some embodiments, these molecules can be used to treat cancer by inhibiting the suppressive activity of BTN1A1 in T cell activation or proliferation. Accordingly, provided herein are uses of these molecules in up-modulating the immune system of a subject by inhibiting or blocking the BTN1A1 signaling. In some embodiments, provided herein are uses of these molecules to block BTN1A1 from binding T cells.

In some embodiments, these molecules result in the destruction of cancer cells through ADCC or CDC mechanism. In some embodiments, these molecules are engineered to have enhanced ADCC activity. In some embodiments, these molecules are engineered to have enhanced CDC activity. For example, these molecules can be engineered to have enhanced interaction with killer cells bearing Fc receptors. Methods to produce such engineered molecules, including engineered antibodies or Fc-fusion proteins, are described herein and also known in the art.

In some embodiments, provided herein are uses of molecules having an antigen binding fragment that immunospecifically binds to BTN1A1 or glycosylated BTN1A1, including anti-BTN1A1 antibodies and anti-glycosylated BTN1A1 antibodies, to treat a disease or disorder in a subject who overexpresses of BTN1A1. In some embodiments, the expression level of BTN1A1 in the subject is higher than a reference level. The reference level can be the average or medium expression level of BTN1A1 in a population of healthy individuals. The reference level can also be determined by statistic analysis of the expression level of a sample population.

Also provided herein are therapeutic uses of molecules having an antigen binding fragment that immunospecifically binds to BTN1A1 or glycosylated BTN1A1, which include anti-BTN1A1 antibodies and anti-glycosylated BTN1A1 antibodies. In some embodiments, the molecules have an antigen binding fragment that immunospecifically binds to glycosylated BTN1A1. In some aspects, the antigen binding fragment immunospecifically binds to BTN1A1 glycosylated at positions N55, N215, and/or N449. In some aspects, the antigen binding fragment immunospecifically binds to BTN1A1 glycosylated at position N55. In some aspects, the antigen binding fragment immunospecifically binds to BTN1A1 glycosylated at position N215. In some aspects, the antigen binding fragment immunospecifically binds to BTN1A1 glycosylated at position N449. In some aspects, the antigen binding fragment immunospecifically binds to one or more glycosylation motifs. In some aspects, the antigen binding fragment immunospecifically binds to BTN1A1 glycosylated at positions N55 and N215. In some aspects, the antigen binding fragments immunospecifically binds to BTN1A1 glycosylated at positions N215 and N449. In some aspects, the antigen binding fragments immunospecifically binds to BTN1A1 glycosylated at positions N55 and N449. In some aspects, the antigen binding fragments immunospecifically binds to BTN1A1 glycosylated at positions N55, N215 and N449.

In some embodiments, provided herein are therapeutic uses of molecules having an antigen binding fragment that preferentially binds to glycosylated BTN1A1 over non-glycosylated BTN1A1. In some aspects, the antigen binding fragments preferentially bind to BTN1A1 glycosylated at positions N55, N215, and/or N449 over non-glycosylated BTN1A1. In some aspects, the antigen binding fragments preferentially bind to BTN1A1 glycosylated at position N55 over non-glycosylated BTN1A1. In some aspects, the antigen binding fragments preferentially bind to BTN1A1 glycosylated at position N215 over non-glycosylated BTN1A1. In some aspects, the antigen binding fragments preferentially bind to BTN1A1 glycosylated at position N449 over non-glycosylated BTN1A1. In some aspects, the antigen binding fragments preferentially bind to one or more glycosylation motifs. In some aspects, the antigen binding fragments preferentially binds to BTN1A1 glycosylated at positions N55 and N215 over non-glycosylated BTN1A1. In some aspects, the antigen binding fragments preferentially bind to BTN1A1 glycosylated at positions N215 and N449 over non-glycosylated BTN1A1. In some aspects, the antigen binding fragments preferentially bind to BTN1A1 glycosylated at positions N55 and N449 over non-glycosylated BTN1A1. In some aspects, the antigen binding fragments preferentially binds to BTN1A1 glycosylated at positions N55, N215 and N449 over non-glycosylated BTN1A1.

In some embodiments, the antigen binding fragment binds to glycosylated BTN1A1 with Kd less than half of the Kd exhibited relative to unglycosylated BTN1A1. In some embodiments, the antigen binding fragment binds to glycosylated BTN1A1 with Kd at least 10 times less than the Kd exhibited relative to unglycosylated BTN1A1.

In some embodiments, the antigen binding fragment binds to glycosylated BTN1A1 with an MFI that is at least twice as high as the MFI as exhibited relative to unglycosylated BTN1A1. In some embodiments, the antigen binding fragment binds to glycosylated BTN1A1 with an MFI that is at least five times as high as the MFI as exhibited relative to unglycosylated BTN1A1.

In some aspects, provided herein are therapeutic uses of molecules having an antigen binding fragment that immunospecifically masks BTN1A1 glycosylation at positions N55, N215, and/or N449. In some aspects, the antigen binding fragments immunospecifically mask BTN1A1 glycosylation at position N55. In some aspects, the antigen binding fragments immunospecifically mask BTN1A1 glycosylation at position N215. In some aspects, the antigen binding fragments immunospecifically mask BTN1A1 glycosylation at position N449. In some aspects, the antigen binding fragments immunospecifically mask one or more glycosylation motifs of BTN1A1. In some aspects, the antigen binding fragments immunospecifically mask BTN1A1 glycosylation at positions N55 and N215. In some aspects, the antigen binding fragments immunospecifically mask BTN1A1 glycosylation at positions N215 and N449. In some aspects, the antigen binding fragments immunospecifically mask BTN1A1 glycosylation at positions N55 and N449. In some aspects, the antigen binding fragments immunospecifically mask BTN1A1 glycosylation at positions N55, N215 and N449.

In some embodiments, provided herein are therapeutic uses of molecules having antigen binding fragment that comprises the VH or VL domain of the murine monoclonal antibody STC810, as depicted in Table 2. In one embodiment, the molecules can have an antigen binding fragment that comprises both the VH and VL domain of the murine monoclonal antibody STC810, as depicted in Table 2. In another embodiment, provided herein are therapeutic uses of molecules having antigen binding fragment that comprises one or more VH CDRs having the amino acid sequence of any one of the VH CDRs of the murine monoclonal antibody STC810, as depicted in Table 2. In another embodiment, the molecules can have antigen binding fragment that comprises one or more VL CDRs having the amino acid sequence of any one of the VL CDRs of the murine monoclonal antibody STC810, as depicted in Table 2. In yet another embodiment, the molecules can have antigen binding fragment that comprises at least one VH CDR and at least one VL CDR of the murine monoclonal antibody STC810, as depicted in Table 2.

In some embodiments, provided herein are therapeutic uses of molecules having antigen binding fragment that competitively blocks (e.g., in a dose-dependent manner) a BTN1A1 epitope described herein. The BTN1A1 epitope can be an epitope of STC810 as described herein. In some embodiments, provided herein are therapeutic uses of molecules having antigen binding fragment that immunospecifically binds to an epitope of BTN1A1 as described herein. The BTN1A1 epitope can be an epitope of STC810 as described herein. In some embodiments, the BTN1A1 epitope has at least five consecutive amino acids of an amino acid sequence of SEQ ID NOS: 31-41.

5.4.1. Diseases and Disorders

In some embodiments, provided herein are uses of the antibodies or other molecules to mediate increased production of cytokines, such as IFN-γ. Thus, provided herein are uses of such antibodies or other molecules in the treatment of diseases and conditions that can be treated with cytokines, such as ovarian and other forms of cancer. In some embodiments, provided herein are uses of the antibodies and other molecules in mediating increased T cell activity or proliferation. Thus, provided in some embodiments are the use of such antibodies and other molecules in the treatment of diseases and conditions that are treatable by increasing T cell activity or proliferation, such as cancer. In some embodiments, provided herein are uses of the antibodies or other molecules as described herein to mediate both increased T cell activity and increased T cell proliferation.

Up-modulation of the immune system is particularly desirable in the treatment of cancers. Additionally, BTN1A1 is specifically and highly expressed in cancer cells. Molecules described herein can also bind to cancer cells and cause their destruction by either direct cytotoxicity, or through ADCC or CDC mechanism. Thus, provided herein are methods of cancer treatment. A cancer refers to a neoplasm or tumor resulting from abnormal uncontrolled growth of cells. A cancer can be a primary cancer or a metastatic cancer.

In some embodiments, provided herein are methods to treat a cancer in a subject by administering a molecule having an antigen binding fragment that immunospecifically binds to BTN1A1 or glycosylated BTN1A1. Cancers for which the treatment methods can be useful include any malignant cell type, such as those found in a solid tumor or a hematological cancer. Exemplary solid tumors include, but are not limited to, a tumor of an organ selected from the group consisting of pancreas, colon, cecum, esophagus, stomach, brain, head, neck, thyroid, thymus, ovary, kidney, larynx, sarcoma, lung, bladder, melanoma, prostate, and breast. Exemplary hematological cancers include, but not limited to, tumors of the bone marrow, T or B cell malignancies, leukemias, lymphomas, blastomas, myelomas, and the like.

Further examples of cancers that can be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung, mesothelioma), cancer of the peritoneum, hepatocellular cancer, gastric or stomach cancer (including gastrointestinal cancer and gastrointestinal stromal cancer), esophageal cancer, pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulvar cancer, thyroid cancer, various types of head and neck cancer, melanoma, superficial spreading melanoma, lentigo malignant melanoma, acral lentiginous melanomas, nodular melanomas, uveal melanomas, germ cell tumors (yolk sac tumors, testicular cancer, choriocarcinoma), as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer can also be of any of the following histological types: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, provided herein are methods to treat a cancer in a subject by administering the molecule described herein having an antigen binding fragment that immunospecifically binds to BTN1A1 or glycosylated BTN1A1, wherein the cancer is lung cancer, prostate cancer, pancreas cancer, ovarian cancer, liver cancer, head & neck cancer, breast cancer, or stomach cancer. In some embodiments, provided herein are methods to treat a cancer in a subject by administering the molecule described herein having an antigen binding fragment that immunospecifically binds to BTN1A1 or glycosylated BTN1A1, wherein the cancer can be lung cancer. The lung cancer can be non-small cell lung cancer (NSCLC). The lung cancer can be small cell lung cancer (SCLC). The NSCLC can be squamous NSCLC. The molecules used for treating lung cancer can be any molecules described herein having an antigen binding fragment that immunospecifically binds to BTN1A1 or glycosylated BTN1A1. In some embodiments, the antigen binding fragment preferentially binds to glycosylated BTN1A1 over non-glycosylated BTN1A1. In some aspects, the antigen binding fragments immunospecifically mask BTN1A1 glycosylation at positions N55, N215, N449, or any combination thereof. In some aspects, the molecules used for treating lung cancer is STC810. In some aspects, the molecules used for treating NSCLC is STC810. In some aspects, the molecules used for treating squamous NSCLC is STC810.

In some embodiments, provided herein are methods to treat a cancer in a subject by administering the molecule described herein having an antigen binding fragment that immunospecifically binds to BTN1A1 or glycosylated BTN1A1, wherein the cancer can be prostate cancer. The molecules used for treating prostate cancer can be any molecules described herein having an antigen binding fragment that immunospecifically binds to BTN1A1 or glycosylated BTN1A1. In some embodiments, the antigen binding fragment preferentially binds to glycosylated BTN1A1 over non-glycosylated BTN1A1. In some aspects, the antigen binding fragments immunospecifically mask BTN1A1 glycosylation at positions N55, N215, N449, or any combination thereof. In some aspects, the molecules used for treating prostate cancer is STC810.

In some embodiments, provided herein are methods to treat a cancer in a subject by administering the molecule described herein having an antigen binding fragment that immunospecifically binds to BTN1A1 or glycosylated BTN1A1, wherein the cancer can be pancreas cancer. The molecules used for treating pancreas cancer can be any molecules described herein having an antigen binding fragment that immunospecifically binds to BTN1A1 or glycosylated BTN1A1. In some embodiments, the antigen binding fragment preferentially binds to glycosylated BTN1A1 over non-glycosylated BTN1A1. In some aspects, the antigen binding fragments immunospecifically mask BTN1A1 glycosylation at positions N55, N215, N449, or any combination thereof. In some aspects, the molecules used for treating pancreas cancer is STC810.

In some embodiments, provided herein are methods to treat a cancer in a subject by administering the molecule described herein having an antigen binding fragment that immunospecifically binds to BTN1A1 or glycosylated BTN1A1, wherein the cancer can be ovarian cancer. The molecules used for treating ovarian cancer can be any molecules described herein having an antigen binding fragment that immunospecifically binds to BTN1A1 or glycosylated BTN1A1. In some embodiments, the antigen binding fragment preferentially binds to glycosylated BTN1A1 over non-glycosylated BTN1A1. In some aspects, the antigen binding fragments immunospecifically mask BTN1A1 glycosylation at positions N55, N215, N449, or any combination thereof. In some aspects, the molecules used for treating ovarian cancer is STC810.

In some embodiments, provided herein are methods to treat a cancer in a subject by administering the molecule described herein having an antigen binding fragment that immunospecifically binds to BTN1A1 or glycosylated BTN1A1, wherein the cancer can be liver cancer. The molecules used for treating liver cancer can be any molecules described herein having an antigen binding fragment that immunospecifically binds to BTN1A1 or glycosylated BTN1A1. In some embodiments, the antigen binding fragment preferentially binds to glycosylated BTN1A1 over non-glycosylated BTN1A1. In some aspects, the antigen binding fragments immunospecifically mask BTN1A1 glycosylation at positions N55, N215, N449, or any combination thereof. In some aspects, the molecules used for treating liver cancer is STC810.

In some embodiments, provided herein are methods to treat a cancer in a subject by administering the molecule described herein having an antigen binding fragment that immunospecifically binds to BTN1A1 or glycosylated BTN1A1, wherein the cancer can be head & neck cancer. The molecules used for treating head & neck cancer can be any molecules described herein having an antigen binding fragment that immunospecifically binds to BTN1A1 or glycosylated BTN1A1. In some embodiments, the antigen binding fragment preferentially binds to glycosylated BTN1A1 over non-glycosylated BTN1A1. In some aspects, the antigen binding fragments immunospecifically mask BTN1A1 glycosylation at positions N55, N215, N449, or any combination thereof. In some aspects, the molecules used for treating head & neck cancer is STC810.

In some embodiments, provided herein are methods to treat a cancer in a subject by administering the molecule described herein having an antigen binding fragment that immunospecifically binds to BTN1A1 or glycosylated BTN1A1, wherein the cancer can be breast cancer. The molecules used for treating breast cancer can be any molecules described herein having an antigen binding fragment that immunospecifically binds to BTN1A1 or glycosylated BTN1A1. In some embodiments, the antigen binding fragment preferentially binds to glycosylated BTN1A1 over non-glycosylated BTN1A1. In some aspects, the antigen binding fragments immunospecifically mask BTN1A1 glycosylation at positions N55, N215, N449, or any combination thereof. In some aspects, the molecules used for treating breast cancer is STC810.

In some embodiments, provided herein are methods to treat a cancer in a subject by administering the molecule described herein having an antigen binding fragment that immunospecifically binds to BTN1A1 or glycosylated BTN1A1, wherein the cancer can be stomach cancer. The molecules used for treating stomach cancer can be any molecules described herein having an antigen binding fragment that immunospecifically binds to BTN1A1 or glycosylated BTN1A1. In some embodiments, the antigen binding fragment preferentially binds to glycosylated BTN1A1 over non-glycosylated BTN1A1. In some aspects, the antigen binding fragments immunospecifically mask BTN1A1 glycosylation at positions N55, N215, N449, or any combination thereof. In some aspects, the molecules used for treating stomach cancer is STC810.

The molecules used for treating cancer can be any molecules described herein having an antigen binding fragment that immunospecifically binds to BTN1A1 or glycosylated BTN1A1. In some embodiments, the antigen binding fragment preferentially bind glycosylated BTN1A1 over non-glycosylated BTN1A1. In some embodiments, the antigen binding fragment binds to glycosylated BTN1A1 with Kd less than half of the Kd exhibited relative to unglycosylated BTN1A1. In some embodiments, the antigen binding fragment binds to glycosylated BTN1A1 with Kd at least 10 times less than the Kd exhibited relative to unglycosylated BTN1A1. In some embodiments, the antigen binding fragment binds to glycosylated BTN1A1 with an MFI that is at least twice as high as the MFI as exhibited relative to unglycosylated BTN1A1. In some embodiments, the antigen binding fragment binds to glycosylated BTN1A1 with an MFI that is at least five times as high as the MFI as exhibited relative to unglycosylated BTN1A1.

In some aspects, the antigen binding fragments immunospecifically mask BTN1A1 glycosylation at positions N55, N215, N449, or any combination thereof.

In some aspects, the molecule useful for cancer treatment is STC810.

5.4.2. Methods of Administration

Provided herein are also methods of using the anti-BTN1A1 antibodies or other molecules having an antigen binding fragment that immunospecifically binds to BTN1A1 or glycosylated BTN1A1 as an antitumor agent by administering a therapeutically effective amount of the antibodies or molecules provided herein to a patient in need thereof. In some embodiments, the patient is a cancer patient.

Various delivery systems are also known and can be used to administer the anti-BTN1A1 antibodies or other molecules having an antigen binding fragment that immunospecifically binds to BTN1A1 or glycosylated BTN1A1, or related pharmaceutical compositions, such as encapsulation in liposomes, microparticles, microcapsules, recombinant cells capable of expressing the antibody or fusion protein, receptor-mediated endocytosis (see, e.g., Wu and Wu, 1987, J. Biol. Chem. 262:4429-4432), construction of a nucleic acid as part of a retroviral or other vector, etc.

The methods of administration as provided herein include, but are not limited to, injection, as by parenteral administration (e.g., intradermal, intramuscular, intraperitoneal, intravenous and subcutaneous), epidural, and mucosal (e.g., intranasal and oral routes). In some embodiments, the antibodies, other molecules, or pharmaceutical compositions provided herein are administered intramuscularly, intravenously, subcutaneously, intravenously, intraperitoneally, orally, intramuscularly, subcutaneously, intracavity, transdermally, or dermally. The compositions can be administered by any convenient route, for example, by infusion or bolus injection, by absorption through epithelial or mucocutaneous linings (e.g., oral mucosa, rectal and intestinal mucosa, etc.) and can be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903; all of which are hereby incorporated by reference in their entireties. In some embodiments, the antibodies, other molecules, or pharmaceutical compositions provided herein are administered locally to the area in need of treatment, which can be achieved by, for example, local infusion, by injection, or by means of an implant, said implant being of a porous, non-porous, or gelatinous material, including membranes, such as sialastic membranes, or fibers. In some embodiments, when administering antibodies or other molecules as described herein, care is taken to use materials to which the antibodies or other molecules do not absorb.

In some embodiments, the humanized or chimeric antibodies provided herein are formulated in liposomes for targeted delivery. Liposomes are vesicles comprised of concentrically ordered phospholipid bilayers which encapsulate an aqueous phase. Liposomes typically have various types of lipids, phospholipids, and/or surfactants. The components of liposomes are arranged in a bilayer configuration, similar to the lipid arrangement of biological membranes. Liposomes can be useful delivery vehicles due, in part, to their biocompatibility, low immunogenicity, and low toxicity. Methods for preparation of liposomes are known in the art and are provided herein, see, e.g., Epstein et al., 1985, Proc. Natl. Acad. Sci. USA, 82: 3688; Hwang et al., 1980 Proc. Natl. Acad. Sci. USA, 77: 4030-4; U.S. Pat. Nos. 4,485,045 and 4,544,545; all of which are hereby incorporated by reference in their entireties.

Provided herein are also methods of preparing liposomes with a prolonged serum half-life, i.e., enhanced circulation time, such as those disclosed in U.S. Pat. No. 5,013,556. In some embodiments, liposomes used in the methods provided herein are not rapidly cleared from circulation, i.e., are not taken up into the mononuclear phagocyte system (MPS). Provided herein are also sterically stabilized liposomes which are prepared using common methods known to one skilled in the art. Sterically stabilized liposomes can contain lipid components with bulky and highly flexible hydrophilic moieties, which reduces the unwanted reaction of liposomes with serum proteins, reduces oposonization with serum components and reduces recognition by MPS. Sterically stabilized liposomes can be prepared using polyethylene glycol. For preparation of liposomes and sterically stabilized liposome, see, e.g., Bendas et al., 2001 BioDrugs, 15(4): 215-224; Allen et al., 1987 FEBS Lett. 223: 42-6; Klibanov et al., 1990 FEBS Lett., 268: 235-7; Blum et al., 1990, Biochim. Biophys. Acta., 1029: 91-7; Torchilin et al., 1996, 1 Liposome Res. 6: 99-116; Litzinger et al., 1994, Biochim. Biophys. Acta, 1190: 99-107; Maruyama et al., 1991, Chem. Pharm. Bull., 39: 1620-2; Klibanov et al., 1991, Biochim Biophys Acta, 1062; 142-8; Allen et al., 1994, Adv. Drug Deliv. Rev, 13: 285-309, which are hereby incorporated by reference in their entireties.

Provided herein are also liposomes that are adapted for specific organ targeting, see, e.g., U.S. Pat. No. 4,544,545, or specific cell targeting, see, e.g., U.S. Patent Application Publication No. 2005/0074403, which are hereby incorporated by reference in their entireties. Particularly useful liposomes for use in the compositions and methods provided herein can be generated by reverse phase evaporation method with a lipid composition comprising phosphatidylcholine, cholesterol, and PEG derivatized phosphatidylethanolamine (PEG-PE). Liposomes can be extruded through filters of defined pore size to yield liposomes with the desired diameter. In some embodiments, a molecule having an antigen binding fragment, e.g., F(ab'), can be conjugated to the liposomes using previously described methods, see, e.g., Martin et al., 1982, J. Biol. Chem. 257: 286-288, which is hereby incorporated by reference in its entirety.

The humanized or chimeric antibodies as described herein can also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is known in the art, see, e.g., U.S. Pat. No. 6,787,153; Allen et al., 1995, Stealth Liposomes, Boca Rotan: CRC Press, 233-44; Hansen et al., 1995, Biochim. Biophys. Acta, 1239: 133-144, which are hereby incorporated by reference in their entireties. In some embodiments, immunoliposomes for use in the methods and compositions provided herein are further sterically stabilized. In some embodiments, the humanized antibodies as described herein are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phospahtidylinositol (PI). To achieve a covalent linkage between an antibody and a hydrophobic anchor, any of the known biochemical strategies in the art can be used, see, e.g., J. Thomas August ed., 1997, *Gene Therapy: Advances in Pharmacology*, Volume 40, Academic Press, San Diego, Calif., p. 399-435, which are hereby incorporated by reference in their entireties. For example, a functional group on an antibody molecule can react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, *Biochemistry*, 35: 1100-1105; Loughrey et al., 1987, *Biochim. Biophys. Acta*, 901: 157-160; Martin et al., 1982, *J. Biol. Chem.* 257: 286-288; Martin et al., 1981, *Biochemistry*, 20: 4429-38, which are hereby incorporated by reference in their entireties. The immunoliposomal formulations having the anti-BTN1A1 antibodies or other molecules having an antigen binding fragment that immunospecifically binds to BTN1A1 or glycosylated BTN1A1 can be particularly effective as therapeutic agents, since they deliver the active ingredient to the cytoplasm of the target cell, i.e., the cell comprising the receptor to which the antibody binds. In some embodiments, the immunoliposomes can have an increased half-life in blood, specifically target cells, and can be internalized into the cytoplasm of the target cells thereby avoiding loss of the therapeutic agent or degradation by the endolysosomal pathway.

The immunoliposomal compositions provided herein can have one or more vesicle forming lipids, an antibody or other molecule of the invention or a fragment or derivative thereof, and, optionally, a hydrophilic polymer. A vesicle forming lipid can be a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations provided herein are known to one skilled in the art and encompassed within the description. In some embodiments, the immunoliposomal compositions further include a hydrophilic polymer, e.g., polyethylene glycol, and ganglioside GM1, which increases the serum half-life of the liposome. Methods of conjugating hydrophilic polymers to liposomes are well known in the art and encompassed within the description. Additional exemplary immunoliposomes and methods of preparing them can be find in, e.g., U.S. Patent Application Publication No. 2003/0044407; PCT International Publication No. WO 97/38731, Vingerhoeads et al., 1994, *Immunomethods*, 4: 259-72; Maruyama, 2000, *Biol. Pharm. Bull.* 23(7): 791-799; Abra et al., 2002, *Journal of Liposome Research*, 12(1&2): 1-3; Park, 2002, *Bioscience Reports*, 22(2): 267-281; Bendas et al., 2001 *BioDrugs*, 14(4): 215-224, J. Thomas August ed., 1997, *Gene Therapy: Advances in Pharmacology*, Volume 40, Academic Press, San Diego, Calif., p. 399-435; all of which are hereby incorporated by reference in their entireties.

Provided herein are also methods of treating a cancer patient by administering a unit dose to the patient the anti-BTN1A1 antibodies or other molecules having an antigen binding fragment that immunospecifically binds to BTN1A or specifically glycosylated BTN1A1. A unit dose refers to physically discrete units suitable as unitary dosage for the subject, each unit containing a predetermined quantity of active material calculated to produce the desired therapeutic effect in association with the required diluent, i.e., carrier, or vehicle.

The antibodies, molecules, or compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual subject. However, suitable dosage ranges for systemic application are disclosed herein and depend on the route of administration. Suitable regimes for initial and booster administration are also contemplated and typically include by an initial administration followed by repeated doses at one or more hour intervals by a subsequent injection or other administration. Exemplary multiple administrations are described herein and are useful to maintain continuously high serum and tissue levels of polypeptide or antibody. Alternatively, continuous intravenous infusion sufficient to maintain concentrations in the blood in the ranges specified for in vivo therapies are contemplated.

A therapeutically effective amount is a predetermined amount calculated to achieve the desired effect. Generally, the dosage will vary with age of, condition of, sex of, and extent of the disease in the patient and can be determined by one of skill in the art. The dosage can be adjusted by the individual physician in the event of any complication.

In some embodiments, the antibodies, molecules, or pharmaceutical compositions provided herein are packaged in a hermetically sealed container, such as an ampoule or sachette. In one embodiment, the antibodies, molecules, or pharmaceutical compositions provided herein are supplied as a dry sterilized lyophilized powder or water free concentrate in a hermetically sealed container and can be reconstituted, e.g., with water or saline to the appropriate concentration for administration to a subject. In some embodiments, the antibodies, molecules, or pharmaceutical compositions provided herein are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies, molecules, or pharmaceutical compositions provided herein should be stored at between 2 and 8° C. in their original container and should be administered within 12 hours, preferably within 6 hours, within 5 hours, within 3 hours, or within 1 hour after being reconstituted. In an alternative embodiment, the antibodies, molecules, or pharmaceutical compositions provided herein are supplied in liquid form in a hermetically sealed container indicating the quantity and concentration of the antibodies, molecules, or pharmaceutical compositions. In some embodiments, the liquid form of the antibodies, molecules, or pharmaceutical compositions provided herein are supplied in a hermetically sealed container at least 1 mg/ml, more preferably at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml.

The precise dose to be employed in the formulation will also depend on the route of administration, and the seriousness of the condition, and should be decided according to the judgment of the practitioner and each patient's circumstances. Effective doses can be extrapolated from dose-response curves derived from in vitro or animal model test systems. For the anti-BTN1A1 antibodies or other molecules having an antigen binding fragment that immunospecifically binds to BTN1A1 or glycosylated BTN1A1, the dosage administered to a patient is typically 0.01 mg/kg to 100 mg/kg of the patient's body weight. In some embodiments, the dosage administered to a patient is between 0.01 mg/kg and 20 mg/kg, 0.01 mg/kg and 10 mg/kg, 0.01 mg/kg and 5 mg/kg, 0.01 and 2 mg/kg, 0.01 and 1 mg/kg, 0.01 mg/kg and 0.75 mg/kg, 0.01 mg/kg and 0.5 mg/kg, 0.01 mg/kg to 0.25 mg/kg, 0.01 to 0.15 mg/kg, 0.01 to 0.10 mg/kg, 0.01 to 0.05 mg/kg, or 0.01 to 0.025 mg/kg of the patient's body weight. In particular, the dosage administered to a patient can be 0.2 mg/kg, 0.3 mg/kg, 1 mg/kg, 3 mg/kg, 6 mg/kg or 10 mg/kg. A dose as low as 0.01 mg/kg is predicted to show appreciable pharmacodynamic effects. Dose levels of 0.10-1 mg/kg are predicted to be most appropriate. Higher doses (e.g., 1-30 mg/kg) can also be expected to be active. Generally, human antibodies have a longer half-life within the human body than antibodies from other species due to the immune response to the foreign polypeptides. Thus, lower dosages of human antibodies and less frequent administration can be practiced. Further, the dosage and frequency of administration of antibodies or other molecules provided herein can be reduced by enhancing uptake and tissue penetration of the antibodies by modifications such as, for example, lipidation.

In yet another embodiment, the compositions can be delivered in a controlled release or sustained release system. Any technique known to one of skill in the art can be used to produce sustained release formulations having one or more antibodies, molecules, or pharmaceutical compositions provided herein. See, e.g., U.S. Pat. No. 4,526,938; PCT publication WO 91/05548; PCT publication WO 96/20698; Ning et al., *Radiotherapy & Oncology* 39:179-189 (1996), Song et al., *PDA Journal of Pharmaceutical Science & Technology* 50:372-397 (1995); Cleek et al., *Pro. Int'l. Symp. Control. Rel. Bioact. Mater.* 24:853-854 (1997); and Lam et al., *Proc. Int'l. Symp. Control Rel. Bioact. Mater.* 24:759-760(1997); all of which are hereby incorporated by reference in their entireties. In one embodiment, a pump can be used in a controlled release system (See Langer, supra; Sefton, 1987, *CRC Crit. Ref Biomed. Eng.* 14:20; Buchwald et al., 1980, *Surgery* 88:507; and Saudek et al., 1989, *N. Engl. J. Med.* 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912,015; 5,989,463; 5,128,326; PCT Publication No. WO 99/15154; and PCT Publication No. WO 99/20253); all of which are hereby incorporated by references in their entireties.

Examples of polymers that can be used in sustained release formulations include, but are not limited to, poly(-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (see U.S. Pat. No. 5,945,155), which is hereby incorporated by references in its entirety. Based upon the therapeutic effect of the in situ controlled release of the bioactive material from the polymer system, the implantation can generally occur anywhere within the body of the patient in need of therapeutic treatment.

In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (see U.S. Pat. No. 5,888,533). Controlled release systems are also discussed in the review by Langer (1990, *Science* 249:1527-1533). Any technique known to one of skill in the art can be used to produce sustained release formulations comprising one or more therapeutic agents provided herein. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760; all of which are hereby incorporated by references in their entireties.

Provided herein are also embodiment wherein the composition has nucleic acids encoding antibodies or other molecules as provided herein, wherein the nucleic acid can be administered in vivo to promote expression of its encoded antibody or other molecule, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

Treatment of a subject with a therapeutically effective amount of antibodies, other molecules or pharmaceutical composition provided herein can include a single treatment or a series of treatments. It is contemplated that the antibodies, molecules, or pharmaceutical compositions provided herein can be administered systemically or locally to treat disease, such as to inhibit tumor cell growth or to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive. In some embodiments, they can be administered after the regression of primary cancer to prevent metastasis.

5.5 Combination Therapies

Also provided herein are compositions and methods that include administration of the anti-BTN1A1 antibodies (including anti-glycosylated BTN1A1 antibodies) or other molecules having an antigen binding fragment that immunospecifically binds to BTN1A1 or glycosylated BTN1A1 to a subject in need thereof, in combination with a second therapy. In some embodiments, the subject is a cancer patient and the second therapy is an anti-cancer or anti-hyperproliferative therapy.

In some embodiments, the compositions and methods that include administration of the antibodies or other molecules provided herein, when used in combination with another anti-cancer or anti-hyperproliferative therapy, can enhance the therapeutic potency of the other anti-cancer or anti-hyperproliferative therapy. Accordingly, methods and compositions described herein can be provided in combination with a second therapy to achieve the desired effect, such as killing of a cancer cell, inhibition of cellular hyperproliferation, and/or inhibition of cancer metastasis.

In some embodiments, the second therapy has a direct cytotoxic effect, such as a chemotherapy, a targeted therapy, a cryotherapy, a hyperthermia therapy, a photodynamic therapy, a high intensity focused ultrasound (HIFU) therapy, a radiotherapy, or a surgical therapy. The targeted therapy can be a biological targeted therapy or a small molecule targeted therapy. In other embodiments, the second therapy does not have a direct cytotoxic effect. For example, the second therapy may be an agent that upregulates the immune system without having a direct cytotoxic effect.

Provided herein are methods that include administration of the anti-BTN1A1 antibodies or other molecules having an antigen binding fragment that immunospecifically binds to BTN1A1 or glycosylated BTN1A1 to a subject in need thereof, in combination with a second or additional therapy. The antibodies, other molecules, or pharmaceutical compositions provided herein can be administered before, during, after, or in various combinations relative to the second anti-cancer therapy. The administrations can be in intervals ranging from concurrently to minutes to days to weeks. In some embodiments where the antibodies or other molecules described herein are provided to a patient separately from a second anti-cancer agent, one would generally ensure that a significant period of time did not expire between the time of each delivery, such that the two compounds would still be able to exert an advantageously combined effect on the patient. In such instances, it is contemplated that one can provide a patient with the antibodies or other molecules provided herein, and the second anti-cancer therapy within about 12 to 24 or 72 h of each other and, more particularly, within about 6-12 h of each other. In some situations the time period for treatment can be extended significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent can be given on any day of day 1 to day 90 (this such range includes intervening days) or any combination thereof, and another agent is given on any day of day 1 to day 90 (this such range includes intervening days) or any combination thereof. Within a single day (24-hour period), the patient can be given one or multiple administrations of the agent(s). Moreover, after a course of treatment, it is contemplated that there is a period of time at which no anti-cancer treatment is administered. This time period can last 1-7 days, and/or 1-5 weeks, and/or 1-12 months or more (this such range includes intervening days), depending on the condition of the patient, such as their prognosis, strength, health, etc. The treatment cycles can be repeated as necessary.

Various combinations can be employed. Listed below are some examples with the treatment with the anti-BTN1A1 antibody or other molecules described herein as "A" and a second anti-cancer therapy as "B":

A/B/A B/A/B B/B/A A/A/B A/B/B B/A/A A/BBB B/A/B/B B/B/B/A B/B/A/B
A/A/B/B A/B/A/B A/B/B/A B/B/A/A B/A/B/A B/A/A/B A/A/A/B B/A/A/A
A/B/A/A A/A/B/A

Administration of any antibodies, molecules, or pharmaceutical compositions provided herein, in combination of a second therapy to a patient will follow general protocols for the administration of such second therapy, taking into account the toxicity, if any, of the second therapy. Therefore, in some embodiments there is a step of monitoring toxicity that is attributable to combination therapy.

Chemotherapy

A wide variety of chemotherapeutic agents can be used in accordance with the present embodiments as the second therapy. A chemotherapeutic can be a compound or composition that is administered in the treatment of cancer. These agents or drugs can be categorized by their mode of activity within a cell, for example, whether and at what stage they affect the cell cycle. Alternatively, an agent can be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

Radiotherapy

Another conventional anticancer therapy that can be used in combination with the methods and compositions described herein is radiotherapy, or radiation therapy. Radiotherapy include using γ-rays, X-rays, and/or the directed delivery of radioisotopes to tumor cells. Other forms of DNA damaging factors are also contemplated, such as microwaves, proton beam irradiation (U.S. Pat. Nos. 5,760, 395 and 4,870,287; all of which are hereby incorporated by references in their entireties), and UV-irradiation. It is most likely that all of these factors affect a broad range of damage on DNA, on the precursors of DNA, on the replication and repair of DNA, and on the assembly and maintenance of chromosomes.

Tumor microenvironment is intrinsically inhibitory due to the presence of myeloid-derived suppressor cells and regulatory T cells that infiltrate the tumor and function to suppress immune responses. In addition, the expression of certain inhibitory molecules on T cells and antigen presenting cells (APCs) can limit effective immune responses. Radiation mediates anti-tumor effects through the induction of tumor cell apoptosis, senescence, autophagy, and in some situations, can stimulate more effective immune responses.

Radiation can be a means to place tumor cells under a stressed condition so that the tumor cells can activate mechanisms to survive the stress. Molecules activated under such stressed conditions can be served as targets for therapies used in combination of radiation. BTN1A1 was identified as a potential target that overexpresses under such conditions.

The molecules as described herein that have an antigen binding fragment that immunospecifically binds BTN1A1 or glycosylated BTN1A1 can stimulate local and systemic immune response. In some embodiments, a therapeutically effective amount of the antibodies, other molecules, or pharmaceutical compositions as described herein are administered before, at the same time with, or after a radiotherapy to achieve a synergistic effect.

In some embodiments, a therapeutically effective amount of the antibodies, other molecules, or pharmaceutical compositions described herein are administered that effectively sensitizes a tumor in a host to irradiation. Irradiation can be ionizing radiation and in particular gamma radiation. In some embodiments, the gamma radiation is emitted by linear accelerators or by radionuclides. The irradiation of the tumor by radionuclides can be external or internal.

In some embodiments, the administration of the antibodies, other molecules, or pharmaceutical compositions described herein commences up to one month, in particular up to 10 days or a week, before the irradiation of the tumor. Additionally, irradiation of the tumor is fractionated the administration of the antibodies, other molecules, or pharmaceutical compositions described herein is maintained in the interval between the first and the last irradiation session.

Irradiation can also be X-ray radiation, gamma ray radiation, or charged particle radiation (proton beam, carbon beam, helium beam) (or "radiation" in general). Dosage ranges for radiation range from daily doses of 50 to 600 roentgens for some interval periods of time (2 or more days to several weeks), to single doses of 800 to 6000 roentgens. Radiation can be administered once daily, twice daily, three times daily, or four times daily. Dosage ranges for radioisotopes vary widely, and depend on the half-life of the isotope, the strength and type of radiation emitted, and the uptake by the neoplastic cells.

Targeted Therapy

Targeted cancer therapies are drugs or other substances that block the growth and spread of cancer by interfering with specific molecules ("molecular targets") that are involved in the growth, progression, and spread of cancer. Targeted cancer therapies are also referred to as "molecularly targeted drugs," "molecularly targeted therapies," "precision medicines," or similar names. Differing from standard chemotherapy, targeted therapies act on specific molecular targets that are associated with cancer, whereas standard chemotherapies usually act on all rapidly dividing normal and cancerous cells.

Targeted therapies include both small molecules targeted therapies and biologic targeted therapies, such as monoclonal antibodies. Small-molecule compounds are typically developed for targets that are located inside the cell because such agents are able to enter cells relatively easily. Biologic targeted therapies such as monoclonal antibodies are commonly used for targets that are outside cells or on the cell surface.

A number of different targeted therapies have been approved for use in cancer treatment. These therapies include hormone therapies, signal transduction inhibitors, gene expression modulator, apoptosis inducer, angiogenesis inhibitor, immunotherapies, and toxin delivery molecules.

Hormone therapies slow or stop the growth of hormone-sensitive tumors, which require certain hormones to grow. Hormone therapies act by preventing the body from producing the hormones or by interfering with the action of the hormones. Hormone therapies have been approved for both breast cancer and prostate cancer.

Signal transduction inhibitors block the activities of molecules that participate in signal transduction, the process by which a cell responds to signals from its environment. During this process, once a cell has received a specific signal, the signal is relayed within the cell through a series of biochemical reactions that ultimately produce the appropriate response(s). In some cancers, the malignant cells are stimulated to divide continuously without being prompted to do so by external growth factors. Signal transduction inhibitors interfere with this inappropriate signaling.

Gene expression modulators modify the function of proteins that play a role in controlling gene expression. Apoptosis inducers cause cancer cells to undergo a process of controlled cell death called apoptosis. Apoptosis is one method the body uses to get rid of unneeded or abnormal cells, but cancer cells have strategies to avoid apoptosis. Apoptosis inducers can get around these strategies to cause the death of cancer cells.

Angiogenesis inhibitors block the growth of new blood vessels to tumors (a process called tumor angiogenesis). A blood supply is necessary for tumors to grow beyond a certain size because blood provides the oxygen and nutrients that tumors need for continued growth. Treatments that interfere with angiogenesis can block tumor growth. Some targeted therapies that inhibit angiogenesis interfere with the action of vascular endothelial growth factor (VEGF), a substance that stimulates new blood vessel formation. Other angiogenesis inhibitors target other molecules that stimulate new blood vessel growth.

Immunotherapies trigger the immune system to destroy cancer cells. Some immunotherapies are monoclonal antibodies that recognize specific molecules on the surface of cancer cells. Binding of the monoclonal antibody to the target molecule results in the immune destruction of cells that express that target molecule. Other monoclonal antibodies bind to certain immune cells to help these cells better kill cancer cells.

Monoclonal antibodies that deliver toxic molecules can cause the death of cancer cells specifically. Once the antibody has bound to its target cell, the toxic molecule that is linked to the antibody—such as a radioactive substance or a poisonous chemical—is taken up by the cell, ultimately killing that cell. The toxin will not affect cells that lack the target for the antibody—i.e., the vast majority of cells in the body.

Cancer vaccines and gene therapy are also considered targeted therapies because they interfere with the growth of specific cancer cells.

For illustration, provided below is a list of FDA approved targeted therapies that can be used in accordance with the present embodiments as the second therapy.

Adenocarcinoma of the stomach or gastroesophageal junction: Trastuzumab (Herceptin®), ramucirumab (Cyramza®)

Basal cell carcinoma: Vismodegib (Erivedge™), sonidegib (Odomzo®)

Brain cancer: Bevacizumab (Avastin®), everolimus (Afinitor®)

Breast cancer: Everolimus (Afinitor®), tamoxifen, toremifene (Fareston®), Trastuzumab (Herceptin®), fulvestrant (Faslodex®), anastrozole (Arimidex®), exemestane (Aromasin®), lapatinib (Tykerb®), letrozole (Femara®), pertuzumab (Perjeta®), ado-trastuzumab emtansine (Kadcyla™), palbociclib (Ibrance®)

Cervical cancer: Bevacizumab (Avastin®)

Colorectal cancer: Cetuximab (Erbitux®), panitumumab (Vectibix®), bevacizumab (Avastin®), ziv-aflibercept (Zaltrap®), regorafenib (Stivarga®), ramucirumab (Cyramza®)

Dermatofibrosarcoma protuberans: Imatinib mesylate (Gleevec®)

Endocrine/neuroendocrine tumors: Lanreotide acetate (Somatuline® Depot)

Head and neck cancer: Cetuximab (Erbitux®)

Gastrointestinal stromal tumor: Imatinib mesylate (Gleevec®), sunitinib (Sutent®), regorafenib (Stivarga®)

Giant cell tumor of the bone: Denosumab (Xgeva®)

Kaposi sarcoma: Alitretinoin (Panretin®)

Kidney cancer: Bevacizumab (Avastin®), sorafenib (Nexavar®), sunitinib (Sutent®), pazopanib (Votrient®), temsirolimus (Torisel®), everolimus (Afinitor®), axitinib (Inlyta®)

Leukemia: Tretinoin (Vesanoid®), imatinib mesylate (Gleevec®), dasatinib (Sprycel®), nilotinib (Tasigna®), bosutinib (Bosulif®), rituximab (Rituxan®), alemtuzumab (Campath®), ofatumumab (Arzerra®), obinutuzumab (Gazyva™) ibrutinib (Imbruvica™), idelalisib (Zydelig®), blinatumomab (Blincyto™)

Liver cancer: Sorafenib (Nexavar®)

Lung cancer: Bevacizumab (Avastin®), crizotinib (Xalkori®), erlotinib (Tarceva®), gefitinib (Iressa®), afatinib dimaleate (Gilotrif®), ceritinib (LDK378/Zykadia), ramucirumab (Cyramza®), nivolumab (Opdivo®), pembrolizumab (Keytruda®)

Lymphoma: Ibritumomab tiuxetan (Zevalin®), denileukin diftitox (Ontak®), brentuximab vedotin (Adcetris®), rituximab (Rituxan®), vorinostat (Zolinza®), romidepsin (Istodax®), bexarotene (Targretin®), bortezomib (Velcade®), pralatrexate (Folotyn®), lenalidomide (Revlimid®), ibrutinib (Imbruvica™) siltuximab (Sylvant™), idelalisib (Zydelig®), belinostat (Beleodag™)

Melanoma: Ipilimumab (Yervoy®), vemurafenib (Zelboraf®), trametinib (Mekinist®), dabrafenib (Tafinlar®), pembrolizumab (Keytruda®), nivolumab (Opdivo®)

Multiple myeloma: Bortezomib (Velcade®), carfilzomib (Kyprolis®), lenaliomide (Revlimid®), pomalidomide (Pomalyst®), panobinostat (Farydak®)

Myelodysplastic/myeloproliferative disorders: Imatinib mesylate (Gleevec®), ruxolitinib phosphate (Jakafi™)

Neuroblastoma: Dinutuximab (Unituxin™)

Ovarian epithelial/fallopian tube/primary peritoneal cancers: Bevacizumab (Avastin®), olaparib (Lynparza™)

Pancreatic cancer: Erlotinib (Tarceva®), everolimus (Afinitor®), sunitinib (Sutent®)

Prostate cancer: Cabazitaxel (Jevtana®), enzalutamide (Xtandi®), abiraterone acetate (Zytiga®), radium 223 chloride (Xofigo®)

Soft tissue sarcoma: Pazopanib (Votrient®)

Systemic mastocytosis: Imatinib mesylate (Gleevec®)

Thyroid cancer: Cabozantinib (Cometriq™), vandetanib (Caprelsa®), sorafenib (Nexavar®), lenvatinib mesylate (Lenvima™)

Immunotherapy

The skilled artisan will understand that immunotherapies can be used in combination or in conjunction with methods of the embodiments. In the context of cancer treatment, immunotherapeutics generally rely on the use of immune effector cells and molecules to target and destroy cancer cells. Rituximab (RITUXAN®) is such an example. Checkpoint inhibitors, such as, for example, ipilumimab, are another such example. The immune effector can be, for example, an antibody specific for some marker on the surface of a tumor cell. The antibody alone can serve as an effector of therapy or it can recruit other cells to actually affect cell killing. The antibody also can be conjugated to a drug or toxin (e.g., chemotherapeutic, radionuclide, ricin A chain, cholera toxin, pertussis toxin) and serve merely as a targeting agent. Alternatively, the effector can be a lymphocyte carrying a surface molecule that interacts, either directly or indirectly, with a tumor cell target. Various effector cells include cytotoxic T cells and NK cells.

In one aspect of immunotherapy, the tumor cell bear some marker that is amenable to targeting, i.e., is not present on the majority of other cells. Many tumor markers exist and any of these can be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, *Infect Immun.*, 66(11):5329-36 (1998); Christodoulides et al., *Microbiology*, 66(11):5329-36(1998)); cytokine therapy, e.g., interferons α, β, and γ, IL-1, GM-CSF, and TNF (Bukowski et al., *Clin Cancer Res.*, 4(10):2337-47 (1998); Davidson et al., *J Immunother.*, 21(5):389-98(1998); Hellstrand et al., *Acta Oncol.* 37(4): 347-53(1998)); gene therapy, e.g., TNF, IL-1, IL-2, and p53 (Qin et al., *Proc Natl Acad Sci USA*, 95(24):14411-6(1998); Austin-Ward and Villaseca, *Rev Med Chil*, 126(7):838-45 (1998); U.S. Pat. Nos. 5,830,880 and 5,846,945); and monoclonal antibodies, e.g., anti-PD1, anti-PDL1, anti-CD20, anti-ganglioside GM2, and anti-p185 (Topalian et al., *The New England journal of medicine*, 366:2443-2454 (2012); Brahmer et al., *The New England journal of medicine* 366:2455-2465 (2012); Hollander, *Front Immunol* (2012): 3:3. doi: 10.3389/fimmu.2012.00003; Hanibuchi et al., *Int J Cancer*, 78(4):480-5(1998); U.S. Pat. No. 5,824,311); all of which are hereby incorporated by reference in their entireties. It is contemplated that one or more anti-cancer therapies can be employed with the therapies described herein that involve the use the molecules having an antigen binding fragment that immunospecifically binds to BTN1A1 or glycosylated BTN1A1.

Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment can be accomplished by perfusion, direct injection, or local application of the area with an additional anti-cancer therapy. Such treatment can be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments can be of varying dosages as well.

Additional Types of Therapies

Additional types of cancer therapies known in the art can be used in combination or in conjunction with methods and compositions provided herein, including but not limited to a cryotherapy, a hyperthermia therapy, a photodynamic therapy, and a high intensity focused ultrasound (HIFU) therapy.

Cryotherapy (also called cryosurgery) is the use of extreme cold produced by liquid nitrogen (or argon gas) to destroy abnormal tissue. Cryosurgery is used to treat external tumors, such as those on the skin. For external tumors, liquid nitrogen is applied directly to the cancer cells with a cotton swab or spraying device. Cryosurgery can also be used to treat tumors inside the body (internal tumors and tumors in the bone). For internal tumors, liquid nitrogen or argon gas is circulated through a hollow instrument called a cryoprobe, which is placed in contact with the tumor. The probes can be put into the tumor during surgery or through the skin (percutaneously). After cryosurgery, the frozen tissue thaws and is either naturally absorbed by the body (for internal tumors), or it dissolves and forms a scab (for external tumors).

A hyperthermia therapy (also called thermal therapy or thermotherapy) is a type of cancer treatment in which body tissue is exposed to high temperatures (up to 113° F.). There are several methods of hyperthermia, including local, regional, and whole-body hyperthermia.

In local hyperthermia, heat is applied to a small area, such as a tumor, using various techniques that deliver energy to heat the tumor. Different types of energy can be used to apply heat, including microwave, radiofrequency, and ultrasound. Depending on the tumor location, there are several approaches to local hyperthermia, including external approaches, intraluminal or endocavitary methods, and interstitial techniques.

In regional hyperthermia, various approaches can be used to heat large areas of tissue, such as a body cavity, organ, or limb, including deep tissue approaches, regional perfusion techniques, and continuous hyperthermic peritoneal perfusion (CHPP).

Whole-body hyperthermia can be used to treat metastatic cancer that has spread throughout the body, which can be accomplished by several techniques that raise the body temperature to 107-108° F., including the use of thermal chambers (similar to large incubators) or hot water blankets.

A photodynamic therapy (PDT) is a treatment that uses a drug, called a photosensitizer or photosensitizing agent, and a particular type of light. When photosensitizers are exposed to a specific wavelength of light, they produce a form of oxygen that kills nearby cells. In the first step of PDT for cancer treatment, a photosensitizing agent is injected into the bloodstream. The agent is absorbed by cells all over the body but stays in cancer cells longer than it does in normal cells. Approximately 24 to 72 hours after injection, when most of the agent has left normal cells but remains in cancer cells, the tumor is exposed to light. The photosensitizer in the tumor absorbs the light and produces an active form of oxygen that destroys nearby cancer cells.

The light used for PDT can come from a laser or other sources. Laser light can be directed through fiber optic cables (thin fibers that transmit light) to deliver light to areas inside the body. Other light sources include light-emitting diodes (LEDs), which can be used for surface tumors, such as skin cancer. Extracorporeal photopheresis (ECP) is a type of PDT in which a machine is used to collect the patient's blood cells, treat them outside the body with a photosensitizing agent, expose them to light, and then return them to the patient.

A high intensity focused ultrasound therapy (or HIFU) is a type of cancer treatment. Doctors give the HIFU treatment using a machine that gives off high frequency sound waves that deliver a strong beam to a specific part of a cancer and kill the cancer cells.

Other Agents

It is contemplated that other agents can be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions can increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, can be used in combination with certain aspects of the present embodiments to improve the treatment efficacy.

5.6 Companion Diagnostics

BTN1A1 is highly and specifically expressed in cancer cells. Provided herein are also methods for detecting expression of BTN1A1 in a sample from a subject using molecules described herein that have an antigen binding fragment that immunospecifically binds to BTN1A1. Accordingly, provided herein are also uses of the molecules described herein as a cancer diagnostic. In some embodiments, provided herein are methods to detect BTN1A1 in a sample from a subject by contacting the sample with molecules described herein to form a complex between the molecule and BTN1A1, and detecting the complex in the sample. In some embodiments, provided herein are methods to provide or aid cancer diagnosis of a subject, comprising contacting a sample from the subject with molecules described herein to form a complex between the molecule and BTN1A1, detecting the complex, and diagnosing the subject as likely having cancer if the complex is detected in the sample. In some embodiments, the methods include detecting the presence of glycosylated BTN1A1 in the sample using an molecules described herein having an antigen binding fragment that immunospecifically binds to glycosylated BTN1A1.

In some embodiments, the molecules have an antigen binding fragment that immunospecifically binds to glycosylated BTN1A1 In some aspects, the molecules have an antigen binding fragment that immunospecifically binds to BTN1A1 glycosylated at positions N55, N215, and/or N449. In some aspects, the antigen binding fragment immunospecifically binds to BTN1A1 glycosylated at position N55. In some aspects, the antigen binding fragment immunospecifically binds to BTN1A1 glycosylated at position N215. In some aspects, the antigen binding fragment immunospecifically binds to BTN1A1 glycosylated at position N449. In some aspects, the antigen binding fragment immunospecifically binds to one or more glycosylation motifs. In some aspects, the antigen binding fragment immunospecifically binds to BTN1A1 glycosylated at positions N55 and N215. In some aspects, the antigen binding fragments immunospecifically binds to BTN1A1 glycosylated at positions N215 and N449. In some aspects, the antigen binding fragments immunospecifically binds to BTN1A1 glycosylated at positions N55 and N449. In some aspects, the antigen binding fragments immunospecifically binds to BTN1A1 glycosylated at positions N55, N215 and N449.

In some embodiments, the molecules are anti-BTN1A1 antibodies. In some embodiments, the molecules are anti-glycosylated BTN1A1 antibodies.

In some embodiments, provided herein are also methods for detecting expression of BTN1A1 in a sample from a subject using molecules described herein that have an antigen binding fragment that comprises the VH or VL domain of the murine monoclonal antibody STC810, as depicted in Table 2. In one embodiment, the molecules can have an antigen binding fragment that comprises both the VH and VL domain of the murine monoclonal antibody STC810, as depicted in Table 2. In another embodiment, provided herein are methods for detecting expression of BTN1A1 in a sample from a subject using molecules described herein that have an antigen binding fragment that comprises one or more VH CDRs having the amino acid sequence of any one of the VH CDRs of the murine monoclonal antibody STC810, as depicted in Table 2. In another embodiment, the molecules can have antigen binding fragment that comprises one or more VL CDRs having the amino acid sequence of any one of the VL CDRs of the murine monoclonal antibody STC810, as depicted in Table 2. In yet another embodiment, the molecules can have antigen binding fragment that comprises at least one VH CDR and at least one VL CDR of the murine monoclonal antibody STC810, as depicted in Table 2.

In some embodiments, provided herein are methods for detecting expression of BTN1A1 in a sample from a subject using molecules described herein that have an antigen binding fragment that competitively blocks (e.g., in a dose-dependent manner) a BTN1A1 epitope described herein. The BTN1A1 epitope can be an epitope of STC810 as described herein. In some embodiments, provided herein are methods for detecting expression of BTN1A1 in a sample from a subject using molecules described herein that have an antigen binding fragment that immunospecifically binds to an epitope of BTN1A1 as described herein. The BTN1A1 epitope can be an epitope of STC810 as described herein. In some embodiments, the BTN1A1 epitope has at least five consecutive amino acids of an amino acid sequence of SEQ ID NOS: 31-41.

In some embodiments, detecting BTN1A1 in a sample includes measuring the expression level of BTN1A1 in the sample using molecules described herein. In other embodiments, detecting BTN1A1 further includes comparing the expression level of BTN1A1 in the sample from the subject to a reference level. In some embodiments, the methods include measuring the expression level of the BTN1A1 in a sample using the molecules described herein, comparing the expression level of the BTN1A1 in the sample with a reference level, and diagnosing the subject as likely having cancer if the expression level of BTN1A1 in the sample is higher than the reference level.

In some embodiments, measuring the BTN1A1 level includes measuring the level of glycosylated BTN1A1 using molecules having an antigen binding fragment that immunospecifically binds to glycosylated BTN1A1, such as anti-glycosylated BTN1A1 antibodies. In some embodiments, measuring the level of glycosylated BTN1A1 in a sample further includes comparing the level of glycosylated BTN1A1 in the sample with a reference level, and diagnosing the subject as likely having cancer if the level of glycosylated BTN1A1 in the sample is higher than the reference level.

In some embodiments, the reference level can be the expression level of BTN1A1 in a sample from a healthy individual. In some embodiments, the reference level can be the average or medium expression level of BTN1A1 in samples from a population of healthy individuals. The reference level can also be a cutoff value determined by statistic analysis of the expression levels of BTN1A1 from samples of a population. Statistic methods that can be used to determine such cutoff value are well known in the art. For example, Receiver Operator Characteristic (ROC) analysis can be utilized to determine the reference expression ratio. A review of the ROC analysis can be found in Soreide, *J Clin Pathol*, 10: 1136 (2008), which is herby incorporated by reference in its entirety.

In some embodiments, the subject can be a healthy subject undergoing a routine medical checkup. In some embodiments, the healthy subject is at risk of having cancer, as determined by the presence of certain risk factors that are well known in the art. Such risk factors include, without limitation, a genetic predisposition, a personal disease history, a familial disease history, a lifestyle factor, an environmental factor, a diagnostic indicator, and the like. In some embodiments, the subject is asymptomatic. An asymptomatic subject further includes a cancer patient who display mild early diagnostic indicators of cancer, but is otherwise symptom or complaint free. In some embodiments, the subject has cancer.

In some embodiments, the subject is suspected of having cancer. In some embodiments, the subject has a genetic predisposition for developing cancer or a family history of cancer. In some embodiments, the subject is exposed to certain lifestyle factors promoting the development of cancer or the subject shows clinical disease manifestations of cancer. In some embodiments, the subject is a patient who is receiving a clinical workup to diagnose cancer or to assess the risk of developing cancer.

The cancer can be a metastatic cancer. The cancer can be a hematological cancer or a solid tumor. In some embodiments, the cancer is a hematological cancer selected from the group consisting of leukemia, lymphoma, and myeloma. In some embodiments, the cancer is a solid tumor selected from the group consisting of breast cancer, lung cancer, thymic cancer, thyroid cancer, head & neck cancer, prostate cancer, esophageal cancer, tracheal cancer, brain cancer, liver cancer, bladder cancer, kidney cancer, stomach cancer, pancreatic cancer, ovarian cancer, uterine cancer, cervical cancer, testicular cancer, colon cancer, rectal cancer or skin cancer, both melanomatous and non-melanomatous skin cancers. The cancer can also be any other type of cancer as described herein.

In some embodiments, the subject is treatment naïve. In some embodiments, the subject is undergoing treatments for cancer (e.g., chemotherapy). In some embodiments, the subject is in remission. In some embodiments, the remission is drug-induced. In some embodiments, the remission is drug-free.

In some embodiments, the methods of detecting BTN1A1 or glycosylated BTN1A1 include obtaining a sample from a subject. The subject can be a human. The subject can be a cancer patient. The sample can be a whole blood sample, a bone marrow sample, a partially purified blood sample, PBMCs, tissue biopsy, circulating tumor cells, circulating elements such as protein complexes or exosomes. In some embodiments, the sample is a blood sample. In some embodiments, the sample is tissue biopsy.

In some embodiments, the methods provided herein include detecting BTN1A1 in a sample using a variety of immunohistochemistry (IHC) approaches or other immunoassay methods using molecules described herein, including anti-BTN1A1 antibodies and anti-glycosylated BTN1A1 antibodies.

IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, preferably polyclonal antisera, and most preferably monoclonal antibodies specific for BTN1A1 can be used. As discussed in greater detail below, the antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available. Automated systems for slide preparation and IHC processing are available commercially. The Ventana® BenchMark XT system is an example of such an automated system.

Standard immunological and immunoassay procedures can be found in *Basic and Clinical Immunology* (Stites & Terr eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Ten, eds., 7th ed. 1991).

Commonly used assays to detect BTN1A1 or glycosylated BTN1A1 include an enzyme-linked immunosorbent assay (ELISA), a fluorescent immunosorbent assay (FIA), a chemiluminescent immunosorbent assay (CLIA), a radioimmunoassay (RIA), an enzyme multiplied immunoassay (EMI), a solid phase radioimmunoassay (SPROA), a fluorescence polarization (FP) assay, a fluorescence resonance energy transfer (FRET) assay, a time-resolved fluorescence resonance energy transfer (TR-FRET) assay and a surface plasmon resonance (SPR) assay.

In some embodiments, the ELISA is a sandwich ELISA. In some embodiments, the ELISA is a direct ELISA. In some embodiments, the ELISA includes the initial step of immobilizing the molecules described herein on a solid support (e.g., on the wall of a microtiter plate well or of a cuvette).

The assays to detect BTN1A1 or glycosylated BTN1A1 include noncompetitive assays, e.g., sandwich assays, and competitive assays. Typically, an assay such as an ELISA assay can be used. ELISA assays are known in the art, e.g., for assaying a wide variety of tissues and samples, including blood, plasma, serum or bone marrow.

A wide range of immunoassay techniques using such an assay format are available, see, e.g., U.S. Pat. Nos. 4,016,043, 4,424,279, and 4,018,653, which are hereby incorporated by reference in their entireties. These include both single-site and two-site or "sandwich" assays of the non-competitive types, as well as in the traditional competitive binding assays. These assays also include direct binding of a labeled antibody to a target antigen. Sandwich assays are commonly used assays. A number of variations of the sandwich assay technique exist. For example, in a typical forward assay, an unlabelled anti-BTN1A1 antibody is immobilized on a solid substrate, and the sample to be tested brought into contact with the bound antibody. After a suitable period of incubation, for a period of time sufficient to allow formation of an antibody-antigen complex, a second anti-BTN1A1 antibody, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative by simple observation of the visible signal, or can be quantitated by comparing with a control sample containing standard amounts of the antigen.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, for example, a first anti-BTN1A1 antibody is either covalently or passively bound to a solid surface. The solid surface can be glass or a polymer, the most commonly used polymers being cellulose, polyacrylamide, nylon, polystyrene, polyvinyl chloride, or polypropylene. The solid supports can be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the antigen. The second anti-BTN1A1 antibody is linked to a reporter molecule which is used to indicate the binding of the second antibody to the molecular marker.

In some embodiments, flow cytometry (FACS) can be used to detect the level of BTN1A1 or glycosylated BTN1A1 in a sample. The flow cytometer detects and reports the intensity of the fluorichrome-tagged antibody, which indicates the level of BTN1A1 or glycosylated BTN1A1. Non-fluorescent cytoplasmic proteins can also be observed by staining permeablized cells. The stain can either be a fluorescence compound able to bind to certain molecules, or a fluorichrome-tagged antibody to bind the molecule of choice.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, and other are discussed herein. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which can be further quantitated, usually spectrophotometrically, to give an indication of the amount of BTN1A1 or glycosylated BTN1A1 present in the sample. Alternately, fluorescent compounds, such as fluorescein and rhodamine, can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of BTN1A1 or glycosylated BTN1A1. Immunofluorescence and EIA techniques are both well established in the art and are discussed herein.

As such, provided herein are methods of cancer diagnosis include detecting the presence or expression levels of BTN1A1 in a sample from a subject using the molecules described therein having an antigen binding fragment that immunospecifically binds to BTN1A1. In some embodiments, the methods further include administering a cancer treatment to the subject diagnosed to have cancer. The cancer treatment can be any cancer therapy as described herein or otherwise known in the art. In some embodiments, the cancer treatment includes administering a therapeutically effective amount of anti-BTN1A1 antibodies to the subject.

5.7 Evaluating Efficacy of Treatment

The expression level of BTN1A1 in a subject can correlate with cancer development. An increase in BTN1A1 level can indicate cancer progression, and a decrease in BTN1A1 level can indicate cancer regression. Accordingly, provided herein are also methods to evaluate the efficacy of a particular cancer treatment in a subject by monitoring the BTN1A1 level in samples of the subject over a course of the treatment using molecules described herein having an antigen binding fragment that immunospecifically binds to BTN1A1. In some embodiments, the methods include detecting the expression levels of BTN1A1. In some embodiments, the methods include detecting the levels of glycosylated BTN1A1.

In some embodiments, the molecules have an antigen binding fragment that immunospecifically binds to glycosylated BTN1A1 In some aspects, the molecules have an antigen binding fragment that immunospecifically binds to BTN1A1 glycosylated at positions N55, N215, and/or N449. In some aspects, the antigen binding fragment immunospecifically binds to BTN1A1 glycosylated at position N55. In some aspects, the antigen binding fragment immunospecifically binds to BTN1A1 glycosylated at position N215. In some aspects, the antigen binding fragment immunospecifically binds to BTN1A1 glycosylated at position N449. In some aspects, the antigen binding fragment immunospecifically binds to one or more glycosylation motifs. In some aspects, the antigen binding fragment immunospecifically binds to BTN1A1 glycosylated at positions N55 and N215. In some embodiments, the molecules are anti-BTN1A1 antibodies. In some embodiments, the molecules are anti-glycosylated BTN1A1 antibodies.

In some embodiments, provided herein are also methods to evaluate the efficacy of a particular cancer treatment in a subject by monitoring the BTN1A1 level in samples of the subject over a course of the treatment using molecules described herein having an antigen binding fragment that immunospecifically binds to BTN1A1. In one embodiment, the molecules can have an antigen binding fragment that comprises the VH or VL domain of the murine monoclonal antibody STC810, as depicted in Table 2. In one embodiment, the molecules can have an antigen binding fragment that comprises both the VH and VL domain of the murine monoclonal antibody STC810, as depicted in Table 2. In another embodiment, the molecules can have an antigen binding fragment that comprises one or more VH CDRs having the amino acid sequence of any one of the VH CDRs of the murine monoclonal antibody STC810, as depicted in Table 2. In another embodiment, the molecules can have antigen binding fragment that comprises one or more VL CDRs having the amino acid sequence of any one of the VL CDRs of the murine monoclonal antibody STC810, as depicted in Table 2. In yet another embodiment, the molecules can have antigen binding fragment that comprises at least one VH CDR and at least one VL CDR of the murine monoclonal antibody STC810, as depicted in Table 2.

In some embodiments, provided herein are also methods to evaluate the efficacy of a particular cancer treatment in a subject by monitoring the BTN1A1 level in samples of the subject over a course of the treatment using molecules described herein having an antigen binding fragment. In some embodiments, the molecules can have an antigen binding fragment that competitively blocks (e.g., in a dose-dependent manner) a BTN1A1 epitope described herein. The BTN1A1 epitope can be an epitope of STC810 as described herein. In some embodiments, the molecules can have an antigen binding fragment that immunospecifically binds to an epitope of BTN1A1 as described herein. The BTN1A1 epitope can be an epitope of STC810 as described herein. In some embodiments, the BTN1A1 epitope has at least five consecutive amino acids of an amino acid sequence of SEQ ID NOS: 31-41.

In some embodiment, provided herein are methods of evaluating the efficacy of a particular cancer treatment in a patient, including: a) contacting two or more samples obtained from the patient at a first and at least one subsequent time point throughout the course of the treatment with a molecule described herein; b) measuring the levels of BTN1A1 in the two or more samples, and c) comparing the levels of BTN1A1 in the two or more samples, where a decreased level of BTN1A1 in a sample obtained at a subsequent time point relative to the level of BTN1A1 in the sample obtained at the first time point indicate that the cancer treatment is efficacious. The molecule can be an anti-BTN1A1 antibody. In some embodiments, the BTN1A1 level can be the level of glycosylated BTN1A1. The molecule can also be an anti-glycosylated BTN1A1 antibody.

In some embodiments, the methods include contacting two or more samples obtained from the patient at a first and at least one subsequent time point throughout the course of the treatment with a molecule described herein to form complexes between the molecule and BTN1A1 in the samples and measuring the levels of BTN1A1 in the two or more samples by measuring the complexes in the sample.

In some embodiments, the levels of BTN1A1 or glycosylated BTN1A1 from two or more samples are measured in one assay. In other embodiments, the levels the levels of BTN1A1 or glycosylated BTN1A1 from two or more samples are measured in multiple assays. In some embodiments, the level of BTN1A1 or glycosylated BTN1A1 is measured the same day as the sample is obtained from the subject. In some embodiments, the level of BTN1A1 or glycosylated BTN1A1 is measured without storage of the sample obtained from the subject.

The sample from a cancer patient can be a whole blood sample, a bone marrow sample, a partially purified blood sample, PBMCs, tissue biopsy, circulating tumor cells, circulating elements such as protein complexes or exosomes. In some embodiments, the sample is a blood sample. In some embodiments, the sample is tissue biopsy. As a person of ordinary skill in the art would understand, any methods of determining the expression level of a protein in a sample as described herein or otherwise known in the art can be used to determine the level of BTN1A1 in a sample from a cancer patient. In some embodiments, the methods include an immunoassay. The immunoassay can be an immunohistochemistry approach, including using molecules described herein to probe and visualize BTN1A1. The immunoassay can include FIA, CLIA, RIA, EMI, SPROA, FP assay, FRET assay, TR-FRET assay or SPR assay.

The cancer treatment or cancer therapy can be any therapy described herein or otherwise known in the art, including but not limited to: a surgical therapy, chemotherapy, biological targeted therapy, small molecular targeted therapy, radiation therapy, cryotherapy, hormonal therapy, immunotherapy and cytokine therapy. In some embodiments, the cancer treatment include a FDA-approved cancer treatment, including an experimental cancer treatment in clinical development. In some embodiments, the cancer treatment includes treatments with a combination of two or more drugs, or two or more types of therapies.

In some embodiments, the cancer treatment includes administering an anti-BTN1A1 antibody to the cancer patient.

In some embodiments, one or more samples were obtained at the beginning of the course of the cancer treatment and one or more samples were obtained at later time points throughout the course of the treatment. In some embodiments, the subsequent time points are 2 or more, 3 or more, 4 or more, 5 or more, 6 or more, 7 or more, 8 or more, 9 or more, 10 or more, 15 or more, 20 or more, 25 or more or 30 or more time points.

In some embodiments, the method further includes adjusting the treatment if the treatment is determined to be not efficacious. Adjusting the treatment can include, for example, adjusting the dose of a drug treatment, increasing the frequency of a drug treatment, treating with a different drug or combination of drugs, or ending the treatment.

In some embodiments, the method further includes repeating a treatment if the treatment is determined to be efficacious.

In some embodiments, the level of BTN1A1 or glycosylated BTN1A1 in the samples obtained at the first time point is decreased by more than 10%, more than 20%, more than 30%, more than 40%, more than 50%, more than 60%, more than 70%, more than 80%, more than 90%, more than 95%, or more than 99% in a subsequence time point.

5.8 Patient Selection

Provided herein are uses of molecules having an antigen binding fragment that immunospecifically binds to BTN1A1 to predict responsiveness of a cancer patient to a cancer treatment by determining the presence or expression level of BTN1A1 in a sample from the patient. In some embodiments, the methods include detecting BTN1A1 in a sample from a cancer patient by contacting the sample with a molecule described herein to form a complex between the molecule and BTN1A1, and predicting that the subject will likely be responsive to a cancer treatment if the complex is detected. In some embodiments, the methods include detecting the presence of glycosylated BTN1A1 in the sample using molecules having antigen binding fragment that immunospecifically binds to glycosylated BTN1A1.

In some embodiments, the molecules have an antigen binding fragment that immunospecifically binds to glycosylated BTN1A1. In some aspects, the molecules have an antigen binding fragment that immunospecifically binds to BTN1A1 glycosylated at positions N55, N215, and/or N449. In some aspects, the antigen binding fragment immunospecifically binds to BTN1A1 glycosylated at position N55. In some aspects, the antigen binding fragment immunospecifically binds to BTN1A1 glycosylated at position N215. In some aspects, the antigen binding fragment immunospecifically binds to BTN1A1 glycosylated at position N449. In some aspects, the antigen binding fragment immunospecifically binds to one or more glycosylation motifs. In some aspects, the antigen binding fragment immunospecifically binds to BTN1A1 glycosylated at positions N55 and N215. In some aspects, the antigen binding fragments immunospecifically binds to BTN1A1 glycosylated at positions N215 and N449. In some aspects, the antigen binding fragments immunospecifically binds to BTN1A1 glycosylated at positions N55 and N449. In some aspects, the antigen binding fragments immunospecifically binds to BTN1A1 glycosylated at positions N55, N215 and N449.

In some embodiments, the molecules are anti-BTN1A1 antibodies. In some embodiments, the molecules are anti-glycosylated BTN1A1 antibodies.

In one embodiment, the molecules provided herein that can be used for patient selection can have an antigen binding fragment that comprises the VH or VL domain of the murine monoclonal antibody STC810, as depicted in Table 2. In one embodiment, the molecules can have an antigen binding fragment that comprises both the VH and VL domain of the murine monoclonal antibody STC810, as depicted in Table 2. In another embodiment, the molecules can have an antigen binding fragment that comprises one or more VH CDRs having the amino acid sequence of any one of the VH CDRs of the murine monoclonal antibody STC810, as depicted in Table 2. In another embodiment, the molecules can have antigen binding fragment that comprises one or more VL CDRs having the amino acid sequence of any one of the VL CDRs of the murine monoclonal antibody STC810, as depicted in Table 2. In yet another embodiment, the molecules can have antigen binding fragment that comprises at least one VH CDR and at least one VL CDR of the murine monoclonal antibody STC810, as depicted in Table 2.

In some embodiments, the molecules provided herein that can be used for patient selection can have an antigen binding fragment that competitively blocks (e.g., in a dose-dependent manner) a BTN1A1 epitope described herein. The BTN1A1 epitope can be an epitope of STC810 as described herein. In some embodiments, the molecules can have an antigen binding fragment that immunospecifically binds to an epitope of BTN1A1 as described herein. The BTN1A1 epitope can be an epitope of STC810 as described herein. In some embodiments, the BTN1A1 epitope has at least five consecutive amino acids of an amino acid sequence of SEQ ID NOS: 31-41.

In other embodiments, detecting BTN1A1 in a sample includes measuring the expression level of BTN1A1 in the sample using molecules described herein. In some embodiments, detecting BTN1A1 further includes comparing the expression level of BTN1A1 in the sample from the subject to a reference level. In some embodiments, the methods include measuring the expression level of the BTN1A1 in a sample using an anti-BTN1A1 antibody, comparing the expression level the BTN1A1 in the sample with a reference level, and predicting that the subject will likely be responsive to a cancer treatment if the expression level of BTN1A1 in the sample is higher than the reference level.

In some embodiments, measuring the BTN1A1 level includes measuring the level of glycosylated BTN1A1 using an anti-glycosylated BTN1A1 antibody. In some embodiments, measuring the level of glycosylated BTN1A1 in a sample further includes comparing the level of glycosylated BTN1A1 in the sample with a reference level, and predicting that the subject will likely be responsive to a cancer treatment if the level of glycosylated BTN1A1 in the sample is higher than the reference level.

The sample from a cancer patient can be a whole blood sample, a bone marrow sample, a partially purified blood sample, PBMCs, tissue biopsy, circulating tumor cells, circulating elements such as protein complexes or exosomes. In some embodiments, the sample is a blood sample. Methods to detect the presence of BTN1A1 or measure the expression level of BTN1A1 are described herein or otherwise known in the art.

The cancer treatment or cancer therapy can be any therapy described herein or otherwise known in the art, including but not limited to: a surgical therapy, chemotherapy, biological targeted therapy, small molecular targeted therapy, radiation therapy, cryotherapy, hormonal therapy, immunotherapy and cytokine therapy. In some embodiments, the cancer treatment include a FDA-approved cancer treatment, including an experimental cancer treatment in clinical development. In some embodiments, the cancer treatment includes treatments with a combination of two or more drugs, or two or more types of therapies.

In some embodiments, the cancer treatment includes administering an anti-BTN1A1 antibody to the cancer patient.

5.9 Kit

Provided herein are kits containing a molecule described herein and one or more ancillary agents. In some embodiments, provided herein is a kit for preparing and/or administering a therapy provided herein. The kit can have one or more sealed vials containing any of the pharmaceutical compositions described herein. The kit can include, for example, a molecule having an antigen binding fragment that immunospecifically binds to BTN1A1 or glycosylated BTN1A1, as well as reagents to prepare, formulate, and/or administer the molecule or perform one or more steps of the methods disclosed herein.

In some embodiments, the antigen binding fragment immunospecifically binds to glycosylated BTN1A1. In some aspects, the antigen binding fragment immunospecifically binds to BTN1A1 glycosylated at positions N55, N215, and/or N449. In some aspects, the antigen binding fragment immunospecifically binds to BTN1A1 glycosylated at position N55. In some aspects, the antigen binding fragment immunospecifically binds to BTN1A1 glycosylated at position N215. In some aspects, the antigen binding fragment immunospecifically binds to BTN1A1 glycosylated at position N449. In some aspects, the antigen binding fragment immunospecifically binds to one or more glycosylation motifs. In some aspects, the antigen binding fragment immunospecifically binds to BTN1A1 glycosylated at positions N55 and N215.

In some embodiments, the molecule is an anti-BTN1A1 antibody. In some embodiments, the anti-BTN1A1 antibody is anti-glycosylated BTN1A1 antibody. In some embodiments, the anti-BTN1A1 antibody is humanized antibody or human antibody.

In one embodiment, the kits provided herein can include molecules having an antigen binding fragment that comprises the VH or VL domain of the murine monoclonal antibody STC810, as depicted in Table 2. In one embodiment, kits provided herein can include molecules having an antigen binding fragment that comprises both the VH and VL domain of the murine monoclonal antibody STC810, as depicted in Table 2. In another embodiment, kits provided herein can include molecules having an antigen binding fragment that comprises one or more VH CDRs having the amino acid sequence of any one of the VH CDRs of the murine monoclonal antibody STC810, as depicted in Table 2. In another embodiment, the molecules can have antigen binding fragment that comprises one or more VL CDRs having the amino acid sequence of any one of the VL CDRs of the murine monoclonal antibody STC810, as depicted in Table 2. In yet another embodiment, the molecules can have antigen binding fragment that comprises at least one VH CDR and at least one VL CDR of the murine monoclonal antibody STC810, as depicted in Table 2.

In some embodiments, kits provided herein can include molecules having an antigen binding fragment that competitively blocks (e.g., in a dose-dependent manner) a BTN1A1 epitope described herein. The BTN1A1 epitope can be an epitope of STC810 as described herein. In some embodiments, kits provided herein can include molecules having an antigen binding fragment that immunospecifically binds to an epitope of BTN1A1 as described herein. The BTN1A1 epitope can be an epitope of STC810 as described herein. In some embodiments, the BTN1A1 epitope has at least five consecutive amino acids of an amino acid sequence of SEQ ID NOS: 31-41.

In some embodiments, the kit further includes a second anticancer agent. The second anticancer agent can be a chemotherapeutic agent, a immunotherapeutic agent, a hormonal therapeutic agent, or a cytokine.

Provided herein are also kits that can be used as a companion diagnostic for cancer. In some embodiments, the kits can be used to provide or aid cancer diagnosis. In some embodiments, the kits can be used to evaluate the efficacy of a cancer treatment. In some embodiments, the kits can be used to predict the responsiveness of a patient to a cancer treatment. In some embodiments, the kits can be used to select patients for a particular cancer treatment. The kit can include, for example, reagents for detecting BTN1A1 in a sample.

The reagent can be a molecule having an antigen binding fragment that immunospecifically binds to BTN1A1 or glycosylated BTN1A1. In some embodiments, the molecules have an antigen binding fragment that immunospecifically binds to glycosylated BTN1A1 In some aspects, the molecules have an antigen binding fragment that immunospecifically binds to BTN1A1 glycosylated at positions N55, N215, and/or N449. In some aspects, the antigen binding fragment immunospecifically binds to BTN1A1 glycosylated at position N55. In some aspects, the antigen binding fragment immunospecifically binds to BTN1A1 glycosylated at position N215. In some aspects, the antigen binding fragment immunospecifically binds to BTN1A1 glycosylated at position N449. In some aspects, the antigen binding fragment immunospecifically binds to one or more glycosylation motifs. In some aspects, the antigen binding fragment immunospecifically binds to BTN1A1 glycosylated at positions N55 and N215. In some embodiments, the molecules are anti-BTN1A1 antibodies. In some embodiments, the molecules are anti-glycosylated BTN1A1 antibodies.

The cancer therapies can be any therapy described herein or otherwise known in the art, including but not limited to: a surgical therapy, chemotherapy, biological targeted therapy, small molecular targeted therapy, radiation therapy, cryotherapy, hormonal therapy, immunotherapy and cytokine therapy. In some embodiments, the cancer therapy includes administering to a cancer patient molecules described herein that have an antigen binding fragment that immunospecifically binds to BTN1A1, such as anti-BTN1A1 antibodies, including anti-glycosylated BTN1A1 antibodies.

In some embodiments, the ancillary reagent for the diagnostic kit can be a secondary antibody, a detection reagent, an immobilization buffer, a blocking buffer, a washing buffer, a detection buffer, or any combination thereof.

Secondary antibodies can include, for example, an anti-human IgA antibody, an anti-human IgD antibody, an anti-human IgE antibody, an anti-human IgG antibody, or an anti-human IgM antibody. In some embodiments, the secondary antibodies are anti-bovine antibodies. Secondary detection antibodies can be monoclonal or polyclonal antibodies. Secondary antibodies can be derived from any mammalian organism, including mice, rats, hamsters, goats, camels, chicken, rabbit, and others. Secondary antibodies can be conjugated to enzymes (e.g., horseradish peroxidase (HRP), alkaline phosphatase (AP), luciferase, and the like) or dyes (e.g., colorimetric dyes, fluorescent dyes, fluorescence resonance energy transfer (FRET)-dyes, time-resolved (TR)-FRET dyes, and the like). In some embodiments, the secondary antibody is a polyclonal rabbit-anti-human IgG antibody, which is HRP-conjugated.

In some aspects, the detection reagent contains a fluorescent detection reagent or a luminescent detection reagent. In some other aspects, the luminescent detection reagent contains luminol or luciferin.

A large selection of washing buffers are known in the art, such as tris(hydroxymethyl)aminomethane (Tris)-based buffers (e.g., Tris-buffered saline, TBS) or phosphate buffers (e.g., phosphate-buffered saline, PBS). Washing buffers can include detergents, such as ionic or non-ionic detergents. In some embodiments, the washing buffer is a PBS buffer (e.g., about pH 7.4) including Tween®20 (e.g., about 0.05% Tween®20).

Any dilution buffer known in the art can be included in a kit of this disclosure. Dilution buffers can include a carrier protein (e.g., bovine serum albumin, BSA) and a detergent (e.g., Tween®20). In some embodiments, the dilution buffer is PBS (e.g., about pH 7.4) including BSA (e.g., about 1% BSA) and Tween®20 (e.g., about 0.05% Tween®20).

In some embodiments, the detection reagent is a colorimetric detection reagent, a fluorescent detection reagent, or a chemiluminescent detection reagent. In some embodiments, the colorimetric detection reagent includes PNPP (p-nitrophenyl phosphate), ABTS (2,2'-azino-bis(3-ethyl-benzothiazoline-6-sulphonic acid)) or OPD (o-phenylenediamine). In some embodiments, the fluorescent detection reagent includes QuantaBlu™ or QuantaRed™ (Thermo Scientific, Waltham, MA). In some embodiments, the luminescent detection reagent includes luminol or luciferin. In some embodiments, the detection reagent includes a trigger (e.g., H2O2) and a tracer (e.g., isoluminol-conjugate).

Any detection buffer known in the art can be included in a kit of this disclosure. In some embodiments the detection buffer is a citrate-phosphate buffer (e.g., about pH 4.2).

Any stop solution known in the art can be included in a kit of this disclosure. The stop solutions of this disclosure terminate or delay the further development of the detection reagent and corresponding assay signals. Stop solutions can include, for example, low-pH buffers (e.g., glycine-buffer, pH 2.0), chaotrophic agents (e.g., guanidinium chloride, sodium-dodecylsulfate (SDS)) or reducing agents (e.g., dithiothreitol, mecaptoethanol), or the like.

In some embodiments, the kits provided herein include a cleaning reagent for an automated assay system. An automated assay system can include systems by any manufacturer. In some embodiments, the automated assay systems include, for example, the BIO-FLASH™, the BEST 2000™, the DS2™, the ELx50 WASHER, the ELx800 WASHER, the ELx800 READER, and the Autoblot S20™. A cleaning reagent can include any cleaning reagent known in the art. In some embodiments, the cleaning reagent is the cleaning reagent recommended by the manufacturer of the automated assay system.

In some embodiments, the kits can also include a suitable container means, which is a container that does not react with components of the kit, such as an eppendorf tube, an assay plate, a syringe, a bottle, or a tube. The container can be made from sterilizable materials, such as plastic or glass.

In some embodiments, the kits further include a solid support. The solid support can include any support known in the art on which a protein of this disclosure can be immobilized. In some embodiments, solid the solid substrates are microtiter well plates, slides (e.g., glass slides), chips (e.g., protein chips, biosensor chips, such as Biacore chips), microfluidic cartridges, cuvettes, beads (e.g., magnetic beads) or resins.

In some other embodiments, the kits provided herein include instruction for using the subunits of the kit for detecting BTN1A1 or glycosylated BTN1A1 in the sample from the subject.

The kits provided herein can be tailored to specific assay technologies. In some embodiments, the kit is an ELISA kit, Dot Blot kit, chemiluminescence immunoassay (CIA) kit or multiplex kit. In some embodiments, the ELSA kit can include a washing buffer, a sample diluents, a secondary antibody-enzyme conjugate, a detection reagent and a stop solution. In some embodiments, the Dot Blot kit includes a washing buffer, a sample diluents, a secondary antibody-enzyme conjugate, a detection reagent, and a stop solution. In some embodiments, the CIA kit includes a washing buffer, a sample diluent, a tracer (e.g., isoluminol-conjugate) and a trigger (e.g., H2O2). In some embodiments, the multiplex kit includes a washing buffer, a sample diluents and a secondary antibody-enzyme conjugate.

In some embodiments, the kit of the present invention has a packaging that includes a label indicating the kit is used for diagnosis, prognosis or monitoring of a cancer. In some embodiments, the kit is used as companion diagnostics for cancer treatments. In some other embodiments, the packaging has a label indicates that the kit is used with a cancer drug. In some embodiments, the kit is used to select a patient for a specific cancer treatment.

In some embodiments, the packaging of the kit includes an FDA-approved label. FDA approved labels can include notification of an FDA-approved use and instructions. In some embodiments, the kit is labeled for Research Use Only (RUO) or for Investigational Use Only (IUO). In some embodiments, the kit is labeled for In Vitro Diagnostic Use (IVD). In some embodiments, the kit is labeled in accordance with Title 21, Code of Federal Regulations, Section 809, Subpart B (21 CFR 89, Subpart B).

6. EXAMPLES

It is understood that modifications which do not substantially change the nature and spirit of the various embodiments described herein are also contemplated. Accordingly, the following examples are intended to illustrate but not in any way limiting.

6.1 Example 1: Identification of BTN1A1 as a Target for Cancer Therapy

Radiation can place tumor cells under a stressed condition such that the tumor cells can activate mechanisms to survive the stress, and the molecules activated under such conditions can serve as a target for either independent therapy or combination therapy with radiation. BTN1A1 was identified as a target that overexpresses under such conditions. Naïve T cells were isolated from a non-tumor bearing mouse and placed into a 96 well plate. The naïve T cells were engineered to contain a knocked-down particular gene of interest by infecting T cells using lentivirus vectors that contain a shRNA of interest. The knock-down of a particular candidate gene was done one well at a time.

After acquiring a stable phenotype, the shRNA treated T cells were incubated with the suppressor cells in the presence of antigen or anti-CD3+anti-CD28, using two sets of suppressor cells: (1) suppressor cells isolated from an irradiated animal; and (2) suppressor cells isolated from a unirradiated animal. Then T-cell proliferation was assessed in individual wells by monitoring 3[H]-thymidine incorporation using the procedures substantially similar to those described in Dolcetti et al., *Current Protocols in Immunology*, 14.17.1-14.17.25 (2010), which is hereby incorporated by reference in its entirety.

The responses of T cells isolated from irradiated vs. unirradiated animals were compared in the same in vitro suppression assay. Proliferation was suppressed in T cells treated with non-target control shRNAs whereas inactivation of target genes that negatively regulate (inhibit) the immune response resulted in an enhanced response (reduced suppression). Significantly better T cell proliferation (i.e., reduced T cell suppression) was observed in samples that contained knock-down of BTN1A1, supporting that BTN1A1 is involved in inhibition of T cell responses, when combined with suppressor cells isolated from an irradiated animal. Accordingly, BTN1A1 was identified as targets for cancer therapy, in particular, as a target whose inhibition can activate patient's own immune system by releasing the immunesuppressive effect by the stressed cancer cells. Furthermore, inhibition of BTN1A1 is expected to sensitive a tumor to additional therapies such as radiotherapy.

6.2 Example 2: Analysis of Glycosylation of Human BTN1A1

The N-glycosylation is a post-translational modification first catalyzed by a membrane-associated oligosaccharyl transferase (OST) complex that transfers a preformed glycan composed of oligosaccharides to an asparagine (Asn) side-chain acceptor located within the NXT motif (-Asn-X-Ser/Thr-) (Cheung and Reithmeier, 2007; Helenius and Aebi, 2001). As shown in FIG. 4, the N-glycosylation of human BTN1A1 was confirmed by the down shift of the protein on a coomassie stained PAGE gel after treatment by PNGase F.

The full length sequence of human BTN1A1 was entered into a N-linked glycosylation sites (Nx[ST]) pattern predicting software (hiv.lanl.gov/content/sequence/GLYCOSITE/glycosite.html). Three potential glycosylation sites were identified by the software, which were N55, N215, and/or N449. As shown in FIGS. 5, N55 and N215 are in extracellular domain of BTN1A1, and N449 is in the intracellular domain.

To pinpoint the glycosylation sites, a sequence alignment of the BTN1A1 amino acid sequences from different species was performed to search for evolutionarily conserved NXT motifs, a consensus N-glycosylation recognition sequence. As shown in FIG. 6, high degree of homology in the glycosylation sites of the extracellular domains of BTN1A1 was observed. As such, the glycosylations sites are evolutionarily conserved across species.

The anti-BTN1A1 antibody described herein can be used to study the glycosylation pattern of BTN1A1. To further confirm if the potential glycosylation sites identified by sequence alignments are indeed glycosylated, the tryptic peptides of a purified human BTN1A1 is analyzed by nano LC-MS/MS. Glycopeptides carrying complex type N-glycans can be identified for N-glycosylation sites.

6.3 EXAMPLE 3: Production of Humanized Anti-BTN1A1 Antibodies

A panel of monoclonal antibodies are produced against a recombinant BTN1A1 polypeptide using standard techniques (e.g., by injecting polypeptide comprising BTN1A1 epitopes as immunogens in rats (Aurrand-Lions et al., *Immunity*, 5(5):391-405(1996)). The BTN1A1 polypeptide can be the full length human BTN1A1, or a fragment thereof having a BTN1A1 epitope. Briefly, human BTN1A1 polypeptides coupled to 100 μg KLH carrier protein (keyhole limpet hemocyanin, Pierce) and mixed with adjuvant 56322 (Sigma), are used to immunize female Wister rats. In total, three injections are performed every 9 days. Two days after a final s.c. injection of human BTN1A1 polypeptides, blasts from draining lymph nodes are fused to Sp2/0 cells, and hybridomas are selected. Growing clones are screened by ELISA for the production of monoclonal antibodies specifically recognizing human BTN1A1. Positive clones are subcloned, rescreened, and further tested. Antibodies are purified on protein G-Sepharose columns (GE HealthCare) according to the manufacturer instructions. The VH and VL chains of the antibodies can be sequenced and the CDRs determined by the IMGT numbering system (Lefranc et al., *Nucleic Acids Res.*, 27(1):209-12 (1999)).

As indicated above, for certain purposes, including for example, use in the in vivo treatment of human disease, it is preferred to employ a humanized derivative of the mouse monoclonal antibody.

To form such humanized antibodies, the framework sequences of the mouse monoclonal antibodies (the "Parental" sequences) are first aligned with framework sequences of a set of "Acceptor" human antibodies in order to identify differences in the framework sequences. Humanization are accomplished by substituting non-matching framework residues between the Parental and the Acceptor. Substitutions at potentially important positions such as those in the Vernier zone, the VH/VL inter-chain interface or CDR canonical class determining positions were analyzed for prospective back mutations (see, Foote, J. et al., *J. Molec. Biol.* 224: 487-499 (1992)).

The Conserved Domain Database (COD) (Marchler-Bauer, et al. (2011) *Nucleic Acids Res.* 39:D225-D229) can be used to determine the domain content of each amino-acid chain and the approximate boundaries of each domain. Variable domain boundaries can be exactly determined along with the boundaries of the CDRs according to several commonly used definitions (Kabat, E. A. et al. (1991) "*Sequences of Proteins of Immunological Interest,*" Fifth Edition. NIH Publication No. 91-3242; Chothia, C. et al., *J. Mol. Biol.* 196:901-917 (1987); Honegger, A. et al., *J. Molec. Biol.* 309(3):657-670 (2001))

Multiple alignments of the Parental sequence to the mouse and human germline sequences are generated using MAFFT (Katoh, K. et al., *Nucleic Acids Res.* 30: 3059-3066 (2002)) and entries in each alignment are ordered according to the sequence identity to the Parental sequence. Reference sets are reduced to a unique set of sequences by clustering at 100% sequence identity and excluding redundant entries.

The optimal Acceptor framework selection is based on the overall Parental antibodies sequence identity to the Acceptor across the framework of both chains; however the positions that compose the VH/VL inter-chain interface are of particular interest. Additionally, the CDR-loops lengths and CDR positions responsible for the discrete set of canonical structures that has been defined for 5 of the CDRs (Chothia, C. et al., *J. Mol. Biol.* 196:901-917 (1987); Martin, A. C. et al., *J. Molec. Biol* 263:800-815 (1996); Al-Laziniki, B. et al., *J. Molec. Biol.* 273:927-948(1997)) are compared to the germlines, in order to determine which germline frameworks have both the same interface residues and are known to support similar CDR-loop conformations.

Based on the parent antibody's sequence alignment to the human germlines the closest matching entries are identified. The choice of the preferred human germline is based on the ordered criteria: (1) Sequence identity across the framework; (2) Identical or compatible inter-chain interface residues; (3) Support loops with the Parental CDRs canonical conformations; (4) The combination of heavy and light germlines are found in expressed antibodies; and (5) Presence of N-glycosylation sites that have to be removed.

A structural model of Fv-region of the humanized antibody is generated. Candidate structural template fragments for the FR and CDRs as well as the full Fv are scored, ranked and selected from an antibody database based on their sequence identity to the target, as well as qualitative crystallographic measures of the template structure such as the resolution, in Angstroms (Å).

In order to structurally align the CDRs to the FR templates, 5 residues on either side of the CDR are included in the CDR template. An alignment of the fragments is generated based on overlapping segments and a structural sequence alignment generated. The template fragments along with the alignment were processed by MODELLER (Sall, A. et al.; *J. Molec. Biol.* 234:779-815(1993)). This protocol creates conformational restraints derived from the set of aligned structural templates. An ensemble of structures which satisfied the constraints are created by conjugate gradient and simulated annealing optimization procedures. Model structures are selected from this ensemble on the basis of an energy score, derived from the score of the proteins structure and the satisfaction of the conformational constraints. The models are inspected and the side chains of the positions which differed between the target and template are optimized using a side chain optimization algorithm and energy minimized. A suite of visualization and computational tools are used to assess the CDRs conformational variability, local packing and surface analysis to select one or more preferred models.

A structural model of the Parental antibody is constructed and inspected for imperfections such as poor atomic packing, strain in bond lengths, bond angles or dihedral angles. These imperfections may indicate potential issues with the structural stability of the antibody. The modeling protocol seeks to minimize such imperfections. The initial structural model of the Humanized Fv contains all safe substitutions (i.e., substitutions that should not affect binding affinity or stability) and cautious substitutions (i.e., the position substitution is made but the position may be important for binding affinity). Substitutions at positions that are considered to be associated with a risk a decreased binding affinity or reduced stability are not altered. The template search and selection is performed separately to the Parental template search in order to create a good stand-alone model rather than a closely matching variant model of the Parental. As the assessment of potential substitutions is performed the model is updated to reflect the preferred substitutions and the effect of back mutations.

6.4 Example 4: Functional Analysis of Glycosylation of BTN1A1

Mutagenesis analysis was performed to confirm the glycosylation sites. A series of asparagine (N) to glutamine (Q) substitutions were generated to determine the specific glycosylation site(s) of BTN1A1, and the glycosylation site were confirmed if the N to Q mutants exhibit reduction in glycosylation compared to wildtype. Using site directed mutagenesis, human BTN1A1 mutations were made that included mutations on glycosylation sites in the extracellular domain (N55Q, N215Q and the compound N55Q and N215Q). These glycosylation specific mutants along with the wildtype BTN1A1 were expressed in 293T cells using standard molecular biology techniques. Cells were lysed and the expression of glycosylation specific mutants along with the wildtype BTN1A1 were detected by western blot. As shown in FIG. 3, N55Q and N215Q each caused a down shift of the protein on the blot, indicating the loss of glycosylation on these mutant forms. Additionally, the BTN1A1 mutation with compound N55Q and N215Q mutations failed to express in 293T cells, demonstrating that glycosylation of BTN1A1 on at least one of these two sites is critical for its expression.

6.5 Example 5: Induction of Cell Surface BTN1A1 in Murine T Cells by Anti CD3/CD28 Stimulation Naïve murine T cells were either mock stimulated (left) or stimulated with anti CD3 (5 ug/ml) and anti CD28 (5 ug/ml) for 2 days and subjected to flow cytometric analysis. As shown in both FIG. 7A and FIG. 7B, high induction of cell surface BTN1A1 in the CD3/CD28 stimulated cells was observed compared to the mock treated cells, demonstrating that the activation of T cells as stimulated by CD3/CD28 can result in the increased expression of BTN1A1.

6.6 Example 6: Induction of BTN1A1 Expression in B16-Ova Melanoma Cells

Extracellular BTN1A1 in B16-Ova cells was detected by staining with antibody only control or FITC-BTN1A1 antibody, and BTN1A1 expression level was examined using flow cytometry. As shown in FIG. 8, bone marrow cells induced the expression of extracellular BTN1A1 in B16-ova melanoma cells.

6.7 EXAMPLE 7: Production and Characterization of Mouse Anti-Human BTN1A1 Antibodies Antibody-producing hybridomas against BTN1A1 were obtained by the fusion of SP2/0 murine myeloma cells with spleen cells isolated from BTN1A1-immunized BALB/c mice according to standardized protocol. Before fusion, sera from mice were validated for binding to immunogen using FACS. A total of 68 monoclonal antibody-producing hybridomas (mAb) were generated.

The isotypes of the monoclonal antibodies were determined by ELISA and provided in Table 5 below. Isotypes of MAbs in hybridoma culture supernatants were determined according to the ELISA technique (Sigma-Aldrich ISO2 SIGMA Mouse Monoclonal Antibody Isotyping Reagents).

TABLE 5

Isotypes of mouse anti-human BTN1A1 monoclonal antibodies

| STC# | Isotype | STC# | Isotype | STC# | Isotype |
|---|---|---|---|---|---|
| 801 | G1/M | 823 | G1 | 701 | G2a |
| 802 | G1/M | 824 | G1 | 704 | G2a |
| 803 | M | 825 | G1 | 705 | M |
| 804 | G1 | 826 | G1 | 706 | G2a |
| 805 | G1 | 827 | G1 | 707 | G2a |
| 806 | G1 | 828 | G1 | 708 | G2a |
| 807 | G1 | 829 | G1 | 711 | G2a |
| 808 | G1 | 830 | G1 | 712 | G2a |
| 809 | G1 | 831 | G1 | 716 | G2a |
| 810 | G2a | 832 | G1 | 719 | G2a |
| 811 | G1 | 833 | G1 | 720 | G2a |
| 812 | G1 | 834 | G1 | 721 | G2a |
| 813 | G1 | 835 | G1 | 722 | G2a |
| 814 | G1 | 837 | G1 | 723 | G2a |
| 815 | G1 | 839 | G1 | 727 | G2a |
| 816 | G1 | 840 | G1 | 729 | G2a |
| 817 | G1 | 848 | G1 | 730 | G2a |
| 818 | G1 | 852 | G1 | 732 | G2a |
| 819 | G1 | 858 | G1 | 733 | G2a/A |
| 820 | G1 | 860 | G1 | 734 | G2a |
| 821 | G1 | 861 | G1 | 735 | G2a |
| 822 | G1 | 862 | G1 | 736 | G2a |
|  |  | 863 | G1 |  |  |
|  |  | 866 | G1 |  |  |

The glyco-specificity of monoclonal anti-BTN1A1 antibodies was characterized by dot blot analysis. Each anti- BTN1A1 mAb (0.5 ug/well loaded) was tested for binding to glycosylated BTN1A1 (PNGaseF "−") or deglycosylated BTN1A1 (PNGaseF "+"). Non-specific antibody controls ("IgG," 0.25 ug/well loaded) was also included in the assay. As shown in FIGS. 9A-9B, both glycosylated BTN1A1 protein and non-glycosylated BTN1A1 (BTN1A1 protein treated with PNGase F) were coated on the solid phase and tested for mAbs and antigens binding affinity. All 13 tested mAbs (STC703, STC709, STC710, STC713, STC715, STC717, STC725, STC738, STC810, STC819, STC820, STC822, and STC838) showed a higher affinity with glycosylated BTN1A1 protein compared to non-glycosylated BTN1A1 protein (PNGase F treated protein), as indicated by a higher band intensity. The glyco-specificity of monoclonal anti-BTN1A1 antibodies was also characterized by FACS analysis. 293T cells overexpressing BTN1A1 WT (fully glycosylated) and 2NQ (fully unglycosylated) were incubated with primary antibodies against BTN1A1, and further washed with secondary antibodies conjugated with FITC. After washing, fluorescence intensity (MFI) was measured to assess relative binding of antibodies to membrane bound glycosylated or unglycosylated BTN1A1. Antibodies that exhibited significantly higher MFI on glycosylated BTN1A1 over unglycosylated BTN1A1 were identified as glyco-specific antibodies. For example, STC810 (same antibody as STC838) exhibited an at least 5 fold higher MFI on glycosylated BTN1A1 over unglycosylated BTN1A1. Eight monoclonal anti-BTN1A1 antibodies (STC702, STC810, STC819, STC820, STC821, STC822, STC838 and STC839) were further tested in FACS (FIG. 10) with their ability to bind BTN1A1 and glycosylation specificity verified.

6.8 Example 8: $K_D$ Analysis of STC810 by Biacore and Octet

In a Biacore assay, the binding affinity between BTN1A1 and monoclonal anti-BTN1A1 antibody STC810 was measured by Surface Plasmon Resonance. Sensorgram and saturation curve of the titration of antibody by BTN1A1-ECD tagged with 6×His or human IgG1 Fc. The protein A chip (BIAcore) was coated with antibody with 600 response units (RU) and the BTN1A1 ECD was injected in the microfluidic channel. The $K_D$ values were obtained using the fitting tool of the BIAevaluation software (BIAcore). FIG. 11 provides sensorgrams showing real-time binding of soluble BTN1A1-Fc protein (2-64 nM with 2-fold dilution; FIG. 11A) or soluble BTN1A1-His protein (2-64 nM with 4-fold dilution; FIG. 11B) to STC810 immobilized on a Protein A-CM5 chip. Flow cells without any immobilized protein were used as the controls for non-specific binding and were subtracted from the presented data.

The $K_D$ value of STC810 was also determined in an octet assay. For high-throughput $K_D$ screening, antibody ligand was loaded to the sensor via 20 nM solution. Baseline was established in PBS containing 1 mg/ml bovine serum albumin (assay buffer), the association step was performed by submerging the sensors in a single concentration of analyte in assay buffer. Dissociation was performed and monitored in fresh assay buffer. All experiments were performed with sensor shaking at 1,000 rpm. ForteBio's data analysis software was used to fit the data to a 1:1 binding model to extract an association rate and dissociation rate. The $K_D$ value was calculated using the ratio kd/ka. In a typical epitope binning assay, antigen BTN1A1-Fc (10 nM) was preincubated with the second antibody (10 nM) for 1 h at room temperature. Control antibody (20 nM) was loaded onto AMC sensors (ForteBio) and remaining Fc-binding sites on the sensor were blocked with a whole mouse IgG antibody (Jackson ImmunoResearch). The sensors were exposed to preincubated antigen-second antibody mixture. Raw data was processed using ForteBio's Data Analysis Software 7.0 and the antibody pairs were assessed for competitive binding. Additional binding by the second antibody indicates an unoccupied epitope (non-competitor), while no binding indicates epitope blocking (competitor).

The $K_D$ value of STC810 as measured by both the Biacore assay and Octet assay is provided in Table 6 below.

TABLE 6

$K_D$ of STC810 Determined by Biacore and Octet

| Antibody | Antigen | $K_D$ (M) | kd (1/Ms) | ka (1/s) | Measured by |
|---|---|---|---|---|---|
| STC810 | hBTN1A1-His | 1.49E−08 | 2.69E+05 | 4.02E−03 | Biacore |
| STC810 | hBTN1A1-Fc | 1.81E−09 | 9.89E+04 | 1.80E−04 | Biacore |
| STC810 | hBTN1A1-Fc | 2.12E−09 | 1.45E+05 | 3.09E−04 | Octet |

6.9 Example 9: Epitope Mapping of STC810

Epitope mapping for the mouse anti-human BTN1A1 monoclonal antibody STC810 was performed by high-mass MALDI analysis with Ag-Ab cross-linking. Table 3 summarizes the cross-linked peptides of BTN1A1-Fc and STC810 analyzed by nLC-orbitrap MS/MS. After protease digestion of the antibody/antigen cross-linked complex with deuterated d0 d12, the nLC-orbitrap MS/MS analysis allowed to detect three cross-linked peptides between BTN1A1(ECD)-Fc antigen and STC810 antibody. These cross-linked peptides have been detected with both Xquest and Stavrox software. FIG. 12 shows the epitope of BTN1A1(ECD)-Fc antigen for STC810:

```
                                    (SEQ ID NO: 34)
        LELRWFRKKVSPA (SEQ ID NO: 35)
        EEGLFTVAASVIIRDTSAKNV
```

As shown in FIG. 12, amino acid residues of BTN1A1 (ECD)-Fc that were cross-linked to STC810, including R41, K42, K43, T185 and K188.

Table 4 summarizes the cross-linked peptides of BTN1A1-His and STC810 analyzed by nLC-orbitrap MS/MS. After protease digestion of the antibody/antigen cross-linked complex with deuterated d0 d12, the nLC-orbitrap MS/MS analysis allowed to detect three cross-linked peptides between BTN1A1(ECD)-His antigen and STC810 antibody. These cross-linked peptides have been detected with both Xquest and Stavrox software. FIG. 13 shows the epitope of BTN1A1(ECD)-His antigen for STC810

```
                                    (SEQ ID NO: 40)
        GRATLVQDGIAKGRV (SEQ ID NO: 41)
        EEGLFTVAASVIIRDTSAKNV
```

As shown in FIG. 13, amino acid residues of BTN1A1 (ECD)-His that were cross-linked to STC810, including R68, K78, T175, 5179 and T185.

The peptides of BTN1A1 that were crosslinked with STC810 as indicated in FIGS. 12-13 and Tables 3 and 4 above were thus identified as binding sites on BTN1A1 for the monoclonal antibody STC810.

6.10 Example 10: Characterization of STC810

The immunospecific binding of STC810 and BTN1A1 WT and its non-glycosylated BTN1A1 variants was tested by western blot and also confocal microscopy. HEK293T cells were transiently transfected with expression vectors for wild-type BTN1A1 and mutant BTN1A1, including N55Q, N215Q, and 2NQ (i.e. N55Q and N215Q). In the Western Blot analysis, at 48 h after transfection, whole-cell lysates were prepared and proteins were separated in native SDS-PAGE. The gel was subjected to immunoblot analysis with antibody for STC810. The expression of the wild-type BTN1A1 and mutant BTN1A1 as detected by STC810 is provided in FIG. 14. As shown in FIG. 14 (upper panel), the expression of BTN1A1 N55Q mutant and mutant N215Q detectable by STC810 was reduced compared to BTN1A1, and expression of BTN1A1 2NQ mutant was further significantly reduced.

The expression of wild-type BTN1A1 (BTN1A1 WT) and mutant BTN1A1 (BTN1A1-2NQ (i.e. N55Q and N215Q)) in HEK293T cells was also observed with Confocal Microscope by staining with STC810. As shown in FIG. 15, BTN1A1 WT was positively stained by STC810 in HEK293T cells, mostly on cell surface; and BTN1A1 2NQ was also stained, but the expression detectable by STC810 was much weaker compared to BTN1A1 WT.

6.11 Example 11: Protein Expression Analysis of BTN1A1 Using STC810

The expression of BTN1A1 in human prostate cancer samples was examined and confirmed by both immunohistochemical (IHC) staining and OPAL staining. To perform IHC staining, formalin-fixed paraffin-embedded sections of prostate tissues from cancer patient were subjected to immunostaining of BTN1A1 using STC810, and visualized by 3,3'-diaminobenzidine (DAB) with hematoxylin counterstain. Positive staining by STC810, but not mouse IgG, was observed as shown in FIG. 16 (Panel A, 3 µg/ml mouse IgG; Panel C, 5 µg/ml mouse IgG; Panel B, 3 µg/ml STC810; Panel D, 5 µg/ml STC810).

The BTN1A1 expression in prostate tumor samples was also detected by OPAL staining using STC810. Stained together with BTN1A1 were also antigens CD8 and cytokeratin as indicated in FIG. 17.

6.12 Example 12: Apoptosis Activation and Proliferation Inhibition of Cancer Cells by Anti-BTN1A1 Antibodies The function of anti-BTN1A1 antibody STC810 was analyzed with apoptosis assay and cell proliferation assay. As shown in FIGS. 18A-B, STC810 resulted in apoptosis in hBTN1A1 overexpressing prostate cancer cells (PC3 cells) treated with activated T cells. FIG. 18A shows apoptotic cells that were stained with green caspase 3/7 fluorescent PC3 cells. FIG. 18B shows the calculation of relative apoptosis of PC3 cells at 120 h post treatment with antibody. As shown, the STC810 significantly increased the T cell dependent apoptosis of PC3 cells in a dose dependent manner. The relative apoptosis of the PC3 cells increased when treated with 5 µg/ml STC810; and at least doubled when cells were treated with 50 pg/ml STC810.

As shown in FIGS. 18C-D, STC810 also inhibited cell proliferation of in hBTN1A1 overexpressing prostate cancer cells (PC3 cells) treated with activated T cells. FIG. 18C shows proliferation of prostate cancer cell as monitored by confluency of PC3 cells on the plate. FIG. 18D shows the calculation of relative proliferation of PC3 cells at 120 h post treatment with antibody. As shown, the STC810 significantly inhibited the proliferation of PC3 cells in a dose dependent manner. The rate of proliferation of the PC3 cells was reduced by about 50% when the cells were treated with 50 pg/ml STC810. These data demonstrated that anti-BTN1A1 antibody can enhance apoptosis and reduce proliferation of cancer cells, such as prostate cancer cells.

6.13 Example 13: Lysosomal Internalization of BTN1A1 by Anti-BTN1A1 Antibodies As provided in FIG. 19, single protein-protein interaction can be detected by duolink, which usually includes the following steps: 1. Incubate with a target primary antibodies; 2. Add PLA probes "PLUS" and "MINUS"; 3. hybridize connector oligos; 4. Ligation to form a complete DNA circle; 5. Rolling circle amplification; and 6. Add fluorescent probes to reveal interaction.

The two targets of interest are marked using primary antibodies raised in different species; and special secondary antibodies tagged with two halves of a DNA circle are used. If the two protein targets are in close proximity, reaction with DNA ligase will complete the DNA circle. DNA polymerase reaction then creates a long strand, to which fluorescently-labeled probes can hybridize, which achieves both specificity and substantial amplification of signal, and allows detection of single protein-protein interactions can be detected.

The Duolink technology was used to detect the binding between BTN1A1 and the lysosozomal marker LAMP1, which indicates the internalization of BTN1A1 to lysozome. HEK293T cells stably overexpressing WT or 2NQ BTN1A1 were plated onto Poly-L-Lysine-coated coverslips and allowed to adhere overnight at 37° C. 5% $CO_2$. Cells were treated 1 h with 10 pg/mL mIgG1 or STC810, fixed for 20' with 10% NBF, then stained with mouse STC810 at 5 pg/mL and rabbit anti-LAMP1 (ab24170, Abcam, Cambridge, UK) at 1 pg/mL and Duolink secondary PLA antibodies (DUO92001, Sigma, St. Louis, MO, US) and green detection according to the manufacturer's specifications. Coverslips were mounted using Vectashield with DAPI (Vector, Burlingame, CA, US) and imaged on a Nikon A1 confocal microscope.

As shown on FIGS. 20A and 20B, antibody STC810 internalized BTN1A1 (wild type, glycosylated version), but not BTN1A1 2NQ (N55Q and N215Q). Upon treatment with STC810, cells stably overexpressing BTN1A1 WT but not BTN1A1 2NQ reflected an increase in the number of green fluorescent spots per nucleus, indicating an increase in the colocalization between BTN1A1 and LAMP1. LAMP1 is a lysosozomal marker, and green spots were localized within the cytosolic compartment of the cell, indicating that BTN1A1 was actively internalized to the lysosomal compartment after interaction with STC810. Lysosomal localization of 2NQ BTN1A1 did not increase after STC810 treatment, demonstrating that the specificity of STC810 to the glycosylated moieties conserved on WT BTN1A1. The detected binding was quantified, with the statistic analysis provided below in Table 7. The qualified results are provided in FIG. 20A.

Table 7: Statistic Analysis of Duolink Results.

TABLE 7(a)

| Anova: Single factor. Summary | | | | | | |
|---|---|---|---|---|---|---|
| Column | Groups | Count | Sum | Average | Variance | |
| 1 | BTN1A1 WT/Control | 3 | 10.45894 | 3.486314 | 9.837783 | |
| 2 | BTN1A1 WT/STC801 | 3 | 106.7864 | 35.59547 | 252.3242 | |
| 3 | BTN1A1 2NQ/Control | 3 | 7.213255 | 2.404418 | 0.648216 | |
| 4 | BTN1A1 2NQ/STC801 | 3 | 11.78599 | 3.928663 | 5.793434 | |

| Source of Variation | SS | df | MS | F | P-value | F crit |
|---|---|---|---|---|---|---|
| Between Groups | 2354.339381 | 3 | 784.7798 | 11.68681 | 0.002705 | 4.066181 |
| Within Groups | 537.2072009 | 8 | 67.1509 | | | |
| Total | 2891.546582 | 11 | | | | |

TABLE 7(b)

| t-Test: Paired Two Sample for Means | | |
|---|---|---|
| | Variable 1 | Variable 2 |
| Mean | 3.486314139 | 35.59546576 |
| Variance | 9.837783416 | 252.3241663 |
| Observations | 3 | 3 |
| Pearson Correlation | −0.213256329 | |
| Hypothesized Mean Difference | 0 | |
| df | 2 | |
| t Stat | −3.303545862 | |
| P(T <= t) one-tail | 0.040347331 | |
| t Critical one-tail | 2.91998558 | |
| P(T <= t) two-tail | 0.080694662 | |
| t Critical two-tail | 4.30265273 | |

The expression of the BTN1A1 WT and BTN1A1 2NQ in HEK293T cells was detected and confirmed by FACS analysis (FIG. 21), and the expression of both BTN1A1 WT and BTN1A1 2NQ demonstrated that the specific internalization of BTN1A1 WT, but not BTN1A1 2NQ to lysosomes by STC810 was not due to the lack of expression of BTN1A1 2NQ.

6.14 Example 14

The molecule provided herein having an antigen binding fragment that immunospecifically binds to BTN1A1 can be conjugated to an imaging agent, a therapeutic agent, a toxin or a radionuclide. The therapeutic agent is a chemotherapeutic agent. The therapeutic agent is a cytotoxin. The molecule provided herein can be conjugated to an imaging agent.

Provided herein are compositions having molecules provided herein that have an antigen binding fragment that immunospecifically binds to BTN1A1, as well as a pharmaceutically acceptable carrier. Provided herein are compositions having molecules provided herein that have an antigen binding fragment that immunospecifically binds to BTN1A1, as well as an ancillary agent.

Provided herein are isolated nucleic acids encoding the VH region or VL region of molecules provided herein that have an antigen binding fragment that immunospecifically binds to BTN1A1. The molecule can be STC810. The isolated nucleic acid can have a sequence of SEQ ID NO: 4. The isolated nucleic acid can have a sequence of SEQ ID NO: 6.

Provided herein are also vectors having the nucleic acid molecules described herein. Provided herein are also host cells having the vector described herein.

Provided herein are also methods of delivering a compound to a cell expressing BTN1A1, comprising contacting said cell with the molecules described herein that have an antigen binding fragment that immunospecifically binds to BTN1A1, wherein the molecule is conjugated with the compound. The cell can be a cancer cell. The compound can be an imaging agent, a therapeutic agent, a toxin or a radionuclide.

Provided herein are also methods of modulating an immune response in a subject comprising administering an effective amount of the molecules described herein to the subject, wherein the molecules have an antigen binding fragment that immunospecifically binds to BTN1A1. The modulating can include: (a) increasing T cell activation; (b) increasing T cell proliferation; or (c) increasing cytokine production.

Provided herein are also methods of enhancing T-cell dependent apoptosis of a cell expressing BTN1A1 comprising contacting the cell with an effective amount of the molecules described herein that have an antigen binding fragment that immunospecifically binds to BTN1A1.

Provided herein are also methods of treating a subject having cancer comprising administering a therapeutically effective amount of the molecules described herein to the subject, wherein the molecules have an antigen binding fragment that immunospecifically binds to BTN1A1. The cancer is a hematological cancer or a solid tumor. The cancer can be a solid tumor such as a breast cancer, lung cancer, thyroid cancer, thymus cancer, head & neck cancer, prostate cancer, esophageal cancer, tracheal cancer, brain cancer, liver cancer, bladder cancer, kidney cancer, stomach cancer, pancreatic cancer, ovarian cancer, uterine cancer, cervical cancer, testicular cancer, colon cancer, rectal cancer or skin cancer. The cancer can be a hematological cancer such as leukemia, lymphoma, or myeloma. The molecule is administered systemically. The molecule can be administered intravenously, intradermally, intratumorally, intramuscularly, intraperitoneally, subcutaneously or locally.

The method can further comprise administering at least a second anticancer therapy to the subject. The second anticancer therapy can be a surgical therapy, chemotherapy, radiation therapy, cryotherapy, hyperthermal therapy, high intensity focused ultrasound therapy, hormonal therapy, immunotherapy or cytokine therapy. The second anticancer therapy is radiation therapy.

Provided herein are also methods of detecting BTN1A1 in a sample from a subject comprising contacting the sample with the molecules provided herein to form a complex between the molecule and BTN1A1, and detecting the complex in the sample, wherein the molecules have an antigen binding fragment that immunospecifically binds to BTN1A1.

The method can further comprise diagnosing the subject as likely having cancer if said complex is detected. The method can further comprise predicting that the subject will likely be responsive to a cancer treatment if said complex is detected. The method can further comprise comparing the expression level of BTN1A1 in the sample from the subject to a reference level and diagnosing the subject as likely having cancer if the expression level of BTN1A1 in the sample is higher than the reference level. The reference level can be the expression level of BTN1A1 in a sample from a healthy individual. The sample can be such as a whole blood sample, a bone marrow sample, a partially purified blood sample, PBMCs, tissue biopsy, circulating tumor cells, circulating protein complexes, or circulating exosomes. The complex can be detected by an assay such as an enzyme-linked immunosorbent assay (ELISA), a fluorescent immunosorbent assay (FIA), a chemiluminescent immunosorbent assay (CLIA), a radioimmunoassay (MA), an enzyme multiplied immunoassay, a solid phase radioimmunoassay (SPROA), a fluorescence polarization (FP) assay, a fluorescence resonance energy transfer (FRET) assay, a time-resolved fluorescence resonance energy transfer (TR-FRET) assay, a surface plasmon resonance (SPR) assay or an immunohistochemistry (IHC) approach.

Provided herein are also methods of evaluating the efficacy of a particular cancer treatment in a patient, comprising: a) contacting two or more samples obtained from the patient at a first and at least one subsequent time point throughout the course of the treatment, with the molecules described herein having an antigen binding fragment that immunospecifically binds to BTN1A1; b) measuring the levels of BTN1A1 in the two or more samples, and c) comparing the levels of BTN1A1 in the two or more samples, where a decreased level of BTN1A1 in a sample obtained at a subsequent time point relative to the level of BTN1A1 in the sample obtained at the first time point indicate that the cancer treatment is efficacious.

Provided herein are also antibody-drug conjugates of the following formulas (Ia) or (Ib):

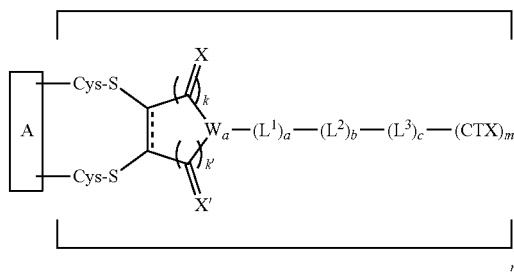

(Ia)

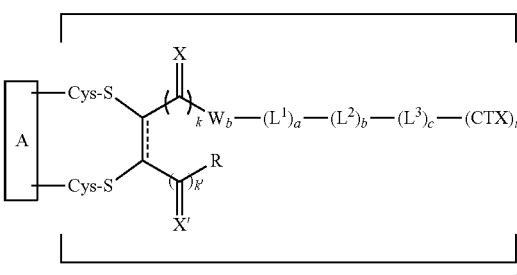

(Ib)

or a pharmaceutically acceptable salt thereof;
wherein:
A is the molecule described herein having an antigen binding fragment that immunospecifically binds to BTN1A1;
the two depicted cysteine residues are from an opened cysteine-cysteine disulfide bond in A;
each X and X' is independently O, S, NH, or $NR^1$ wherein $R^1$ is $C_{1-6}$ alkyl;
$W_a$ is =N—, =CH—, =CHCH$_2$—, =C($R^2$)—, or =CHCH($R^2$)—; $W_b$ —NH—, —N(R')—, —CH$_2$—, —CH$_2$—NH—, —CH$_2$—N(R')—, —CH$_2$CH$_2$—, —CH($R^2$)—, or —CH$_2$CH($R^2$)—; wherein $R^1$ and $R^2$ are independently C1-6 alkyl;
CTX is a cytotoxin;
R is any chemical group; or R is absent;
each $L^1$, $L^2$ and $L^3$ is independently a linker selected from the group consisting of —O—, —C(O)—, —S—, —S(O)—, —S(O)$_2$—, —NH—, —NCH$_3$—, —(CH$_2$)$_q$—, —NH(CH$_2$)$_2$NH—, —OC(O)—, —CO$_2$—, —NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)$_p$, —(CH$_2$CH$_2$O)$_p$CH$_2$CH$_2$—, —CH$_2$CH$_2$—(CH$_2$CH$_2$O)$_p$—, —OCH(CH$_2$O—)$_2$, -(AA)$_r$-, cyclopentanyl, cyclohexanyl, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$ alkyl, —C(O)CH$_3$, —CN, —NH—, —NH$_2$, —O—, —OH, —NHCH$_3$, —N(CH$_3$)$_2$, and C$_{1-3}$ alkyl;
a, b and c are each independently an integer of 0, 1, 2 or 3, provided that at least one of a, b or c is 1;
each k and k' is independently an integer of 0 or 1;
each p is independently an integer of 1 to 14;

each q is independently an integer from 1 to 12;
each AA is independently an amino acid;
each r is 1 to 12;
m is an integer of 1 to 4;
n is an integer of 1 to 4; and
the ===== bond represents a single or a double bond.

A can be an anti-BTN1A1 antibody. The CTX can be such as a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, or an anti-metabolite. The CTX can be such as Actinomycin-D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, or Vincristin. The CTX can be an auristatin, a calicheamicin, a maytansinoid, or a tubulysin. The CTX can be monomethylauristatin E, monomethylauristatin F, calicheamicin γ, mertansine, a pyrrolobenzodiazepine, tubulysin T2, tubulysin T3, or tubulysin T4.

The instant application contains a Sequence Listing which has been submitted electronically in ASCII format and is hereby incorporated by reference in its entirety. Said ASCII copy, created on Nov. 18, 2020, is named 13532-024-999_Sequence_Listing.TXT and is 23,449 bytes in size.

Throughout this application various publications have been referenced. The disclosures of these publications in their entireties are hereby incorporated by reference in this application in order to more fully describe the state of the art to which this disclosure pertains. While examples of certain particular embodiments are provided herein, it will be apparent to those skilled in the art that various changes and modifications may be made. Such modifications are also intended to fall within the scope of the appended claims.

What is claimed is:

1. A method of inhibiting the proliferation of cancer cells expressing BTN1A1 comprising contacting the cells with an effective amount of a molecule, wherein the molecule comprises an antigen binding fragment that immunospecifically binds to BTN1A1, wherein said antigen binding fragment comprises:
   (i) (a) a heavy chain variable region ($V_H$) comprising a $V_H$ complementarity-determining region (CDR) 1, a $V_H$ CDR2, and a $V_H$ CDR3 having an amino acid sequence of a $V_H$ CDR1, a $V_H$ CDR2, and a $V_H$ CDR3, respectively, of a $V_H$ having the amino acid sequence of SEQ ID NO:3; and
   (b) a light chain variable region (V) comprising a $V_L$ CDR1, a $V_L$ CDR2, and a $V_L$ CDR3 having an amino acid sequence of a $V_L$ CDR1, a $V_L$ CDR2, and a $V_L$ CDR3, respectively, of a $V_L$ having the amino acid sequence of SEQ ID NO:5; or
   (ii) (a) a $V_H$ comprising:
      (1) a $V_H$ CDR1 having the amino acid sequence of SEQ ID NO:7;
      (2) a $V_H$ CDR2 having the amino acid sequence of SEQ ID NO:8; and
      (3) a $V_H$ CDR3 having the amino acid sequence of SEQ ID NO:9; and
   (b) a $V_L$ comprising:
      (1) a $V_L$ CDR1 having the amino acid sequence of SEQ ID NO:19;
      (2) a $V_L$ CDR2 having the amino acid sequence of SEQ ID NO:20; and
      (3) a $V_L$ CDR3 having the amino acid sequence of SEQ ID NO:21;
   or
   (iii) (a) a $V_H$ comprising:
      (1) a $V_H$ CDR1 having the amino acid sequence of SEQ ID NO:10;
      (2) a $V_H$ CDR2 having the amino acid sequence of SEQ ID NO:11; and
      (3) a $V_H$ CDR3 having the amino acid sequence of SEQ ID NO:12; and
   (b) a $V_L$ comprising:
      (1) a $V_L$ CDR1 having the amino acid sequence of SEQ ID NO:22;
      (2) a $V_L$ CDR2 having the amino acid sequence of SEQ ID NO:23; and
      (3) a $V_L$ CDR3 having the amino acid sequence of SEQ ID NO:24;
   or
   (iv) (a) a $V_H$ comprising:
      (1) a $V_H$ CDR1 having the amino acid sequence of SEQ ID NO:13;
      (2) a $V_H$ CDR2 having the amino acid sequence of SEQ ID NO:14; and
      (3) a $V_H$ CDR3 having the amino acid sequence of SEQ ID NO:15; and
   (b) a $V_L$ comprising:
      (1) a $V_L$ CDR1 having the amino acid sequence of SEQ ID NO:25;
      (2) a $V_L$ CDR2 having the amino acid sequence of SEQ ID NO:26; and
      (3) a $V_L$ CDR3 having the amino acid sequence of SEQ ID NO:27;
   or
   (v) (a) a $V_H$ comprising:
      (1) a $V_H$ CDR1 having the amino acid sequence of SEQ ID NO:16;
      (2) a $V_H$ CDR2 having the amino acid sequence of SEQ ID NO:17; and
      (3) a $V_H$ CDR3 having the amino acid sequence of SEQ ID NO:18; and
   (b) a $V_L$ comprising:
      (1) a $V_L$ CDR1 having the amino acid sequence of SEQ ID NO:28;
      (2) a $V_L$ CDR2 having the amino acid sequence of SEQ ID NO:29; and
      (3) a $V_L$ CDR3 having the amino acid sequence of SEQ ID NO:30.

2. The method of claim 1, wherein said cancer cells are selected from the group consisting of lung cancer cells, prostate cancer cells, pancreas cancer cells, ovarian cancer cells, liver cancer cells, head & neck cancer cells, breast cancer cells, and stomach cancer cells.

3. The method of claim 1, wherein said cancer cells are lung cancer cells.

4. The method of claim 3, wherein said lung cancer cells are non small cell lung cancer (NSCLC) cells.

5. The method of claim 4, wherein said NSCLC cells are squamous NSCLC cells.

6. The method of claim 1, wherein the heavy chain variable ($V_H$) region comprises the amino acid sequence of SEQ ID NO: 3 and the light chain variable ($V_L$) region comprises the amino acid sequence of SEQ ID NO: 5.

7. A method of treating cancer in a subject, comprising administering to the subject a therapeutically effective amount of a molecule, wherein the molecule comprises an antigen binding fragment that immunospecifically binds to BTN1A1, wherein said antigen binding fragment comprises:
(i) (a) a heavy chain variable region ($V_H$) comprising a $V_H$ complementarity-determining region (CDR) 1, a $V_H$ CDR2, and a $V_H$ CDR3 having an amino acid sequence of a $V_H$ CDR1, a $V_H$ CDR2, and a $V_H$ CDR3, respectively, of a $V_H$ having the amino acid sequence of SEQ ID NO:3; and
  (b) a light chain variable region (V) comprising a $V_L$ CDR1, a $V_L$ CDR2, and a $V_L$ CDR3 having an amino acid sequence of a $V_L$ CDR1, a $V_L$ CDR2, and a $V_L$ CDR3, respectively, of a $V_L$ having the amino acid sequence of SEQ ID NO:5; or
(ii) (a) a $V_H$ comprising:
  (1) a $V_H$ CDR1 having the amino acid sequence of SEQ ID NO:7;
  (2) a $V_H$ CDR2 having the amino acid sequence of SEQ ID NO:8; and
  (3) a $V_H$ CDR3 having the amino acid sequence of SEQ ID NO:9; and
  (b) a $V_L$ comprising:
  (1) a $V_L$ CDR1 having the amino acid sequence of SEQ ID NO:19;
  (2) a $V_L$ CDR2 having the amino acid sequence of SEQ ID NO:20; and
  (3) a $V_L$ CDR3 having the amino acid sequence of SEQ ID NO:21;
  or
(iii) (a) a $V_H$ comprising:
  (1) a $V_H$ CDR1 having the amino acid sequence of SEQ ID NO:10;
  (2) a $V_H$ CDR2 having the amino acid sequence of SEQ ID NO:11; and
  (3) a $V_H$ CDR3 having the amino acid sequence of SEQ ID NO:12; and
  (b) a $V_L$ comprising:
  (1) a $V_L$ CDR1 having the amino acid sequence of SEQ ID NO:22;
  (2) a $V_L$ CDR2 having the amino acid sequence of SEQ ID NO:23; and
  (3) a $V_L$ CDR3 having the amino acid sequence of SEQ ID NO:24;
  or
(iv) (a) a $V_H$ comprising:
  (1) a $V_H$ CDR1 having the amino acid sequence of SEQ ID NO:13;
  (2) a $V_H$ CDR2 having the amino acid sequence of SEQ ID NO:14; and
  (3) a $V_H$ CDR3 having the amino acid sequence of SEQ ID NO:15; and
  (b) a $V_L$ comprising:
  (1) a $V_L$ CDR1 having the amino acid sequence of SEQ ID NO:25;
  (2) a $V_L$ CDR2 having the amino acid sequence of SEQ ID NO:26; and
  (3) a $V_L$ CDR3 having the amino acid sequence of SEQ ID NO:27;
  or
(v) (a) a $V_H$ comprising:
  (1) a $V_H$ CDR1 having the amino acid sequence of SEQ ID NO:16;
  (2) a $V_H$ CDR2 having the amino acid sequence of SEQ ID NO:17; and
  (3) a $V_H$ CDR3 having the amino acid sequence of SEQ ID NO:18; and
  (b) a $V_L$ comprising:
  (1) a $V_L$ CDR1 having the amino acid sequence of SEQ ID NO:28;
  (2) a $V_L$ CDR2 having the amino acid sequence of SEQ ID NO:29; and
  (3) a $V_L$ CDR3 having the amino acid sequence of SEQ ID NO:30.

8. The method of claim 7, wherein the cancer is selected from the group consisting of lung cancer, prostate cancer, pancreatic cancer, ovarian cancer, liver cancer, head & neck cancer, breast cancer, stomach cancer, carcinoma, lymphoma, blastoma, sarcoma, leukemia, squamous cell cancer, cancer of the peritoneum, hepatocellular cancer, esophageal cancer, glioblastoma, cervical cancer, bladder cancer, colon cancer, colorectal cancer, endometrial or uterine carcinoma, salivary gland carcinoma, kidney or renal cancer, vulvar cancer, thyroid cancer, melanoma, superficial spreading melanoma, lentigo malignant melanoma, acral lentiginous melanomas, nodular melanomas, uveal melanomas, germ cell tumors, as well as B-cell lymphoma, chronic lymphocytic leukemia (CLL), acute lymphoblastic leukemia (ALL), Hairy cell leukemia, multiple myeloma, acute myeloid leukemia (AML) and chronic myeloblastic leukemia.

9. The method of claim 8, wherein the lung cancer is small-cell lung cancer, non-small cell lung cancer (NSCLC), adenocarcinoma of the lung, squamous carcinoma of the lung, or mesothelioma.

10. The method of claim 8, wherein the stomach cancer is gastrointestinal cancer or gastrointestinal stromal cancer.

11. The method of claim 8, wherein the germ cell tumors are yolk sac tumors, testicular cancer, or choriocarcinoma.

12. The method of claim 8, wherein the B-cell lymphoma is low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma or Waldenstrom's macroglobulinemia.

13. The method of claim 7, wherein the heavy chain variable ($V_H$) region comprises the amino acid sequence of SEQ ID NO: 3 and the light chain variable ($V_L$) region comprises the amino acid sequence of SEQ ID NO: 5.

* * * * *